United States Patent
Luan et al.

(10) Patent No.: US 7,466,797 B2
(45) Date of Patent: Dec. 16, 2008

(54) ERROR CONTROL IN ALGORITHMIC APPROACH TO STEP-AND-SHOOT INTENSITY MODULATED RADIATION THERAPY

(75) Inventors: Shuang Luan, Albuquerque, NM (US); Danny Z. Chen, Granger, IN (US); Xiaobo S. Hu, Granger, IN (US); Chao Wang, Mishawaka, IN (US); Xiaodong Wu, Iowa City, IA (US); Cedric X. Yu, Clarksville, MD (US)

(73) Assignee: University of Notre Dame du Lac, Notre Dame, IN (US)

( * ) Notice: Subject to any disclaimer, the term of this patent is extended or adjusted under 35 U.S.C. 154(b) by 267 days.

(21) Appl. No.: 11/085,529

(22) Filed: Mar. 22, 2005

(65) Prior Publication Data
US 2008/0063141 A1    Mar. 13, 2008

Related U.S. Application Data

(60) Provisional application No. 60/554,902, filed on Mar. 22, 2004.

(51) Int. Cl.
*A61N 5/10*    (2006.01)
(52) U.S. Cl. ........................................................ 378/65
(58) Field of Classification Search .................. 378/65
See application file for complete search history.

(56) References Cited

U.S. PATENT DOCUMENTS 7,266,175 B1 *    9/2007   Romesberg ................... 378/65

FOREIGN PATENT DOCUMENTS

WO          WO 0249044 A2 *   6/2002

OTHER PUBLICATIONS

Chen, et al. "Generalized Geometric Approaches for Leaf Sequencing Problems in Radiation Therapy" International Journal of Computational Geometry & Applications, Nov. 1, 2004.
Chen et al.; "Geometric Algorithms for Static Leaf Sequencing Problems in Radiation Therapy." International Journal of Computational Geometry and Applications, 14(5):311-339, 2004.

(Continued)

*Primary Examiner*—Chih-Cheng G Kao
*Assistant Examiner*—John M Corbett
(74) *Attorney, Agent, or Firm*—Jagtiani + Guttag

(57) ABSTRACT

The present invention provides a method comprising the following steps: (a) partitioning an intensity modulated beam into a set of sub-IMBs; and (b) partitioning the sub-IMBs into segments, wherein steps (a) and (b) introduce no machine delivery error. The present invention also provides a method comprising the following steps: (a) recursively partitioning an intensity modulated beam into plateaus; and (b) partitioning the plateaus into segments, wherein step (a) comprises determining a tradeoff between machine delivery error and the number of segments into which the plateaus will be partitioned in step (b).

68 Claims, 22 Drawing Sheets

OTHER PUBLICATIONS

Chen et al.; "Optimal Terrain Construction Problems and Applications in Intensity-Modulated Radiation Therapy." Lecture Notes in Computer Science, Springer-Verlag, Proc. 10$^{th}$ Annual European Symposium on Algorithms, vol. 2461, pp. 270-283, 2002.

Luan et al., "A New MLC Segmentation Algorithm/Software for Step and Shoot IMRT." Med. Phys., 31(4):695-707, 2004.

Chen et al., "Generalized Geometric Approaches for Leaf Sequencing Problems in Radiation Therapy", International Journal of Computational Geometry and Applications Feb. 3, 2004.

Chen et al., "Mountain Reduction, Block Matching, and Medical Applicatons" (2005).

* cited by examiner

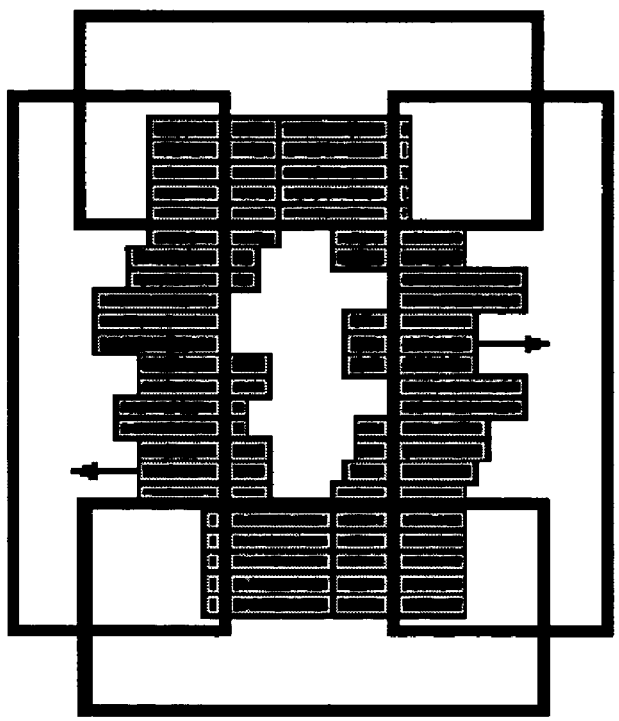

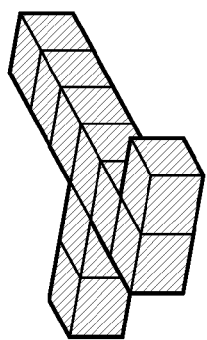
FIG.3
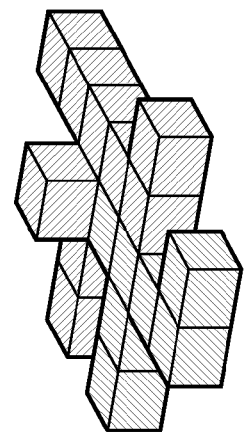
FIG.4
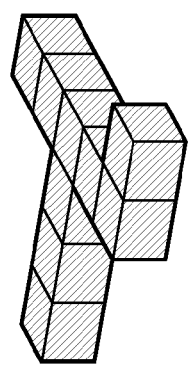
FIG.5
FIG.6

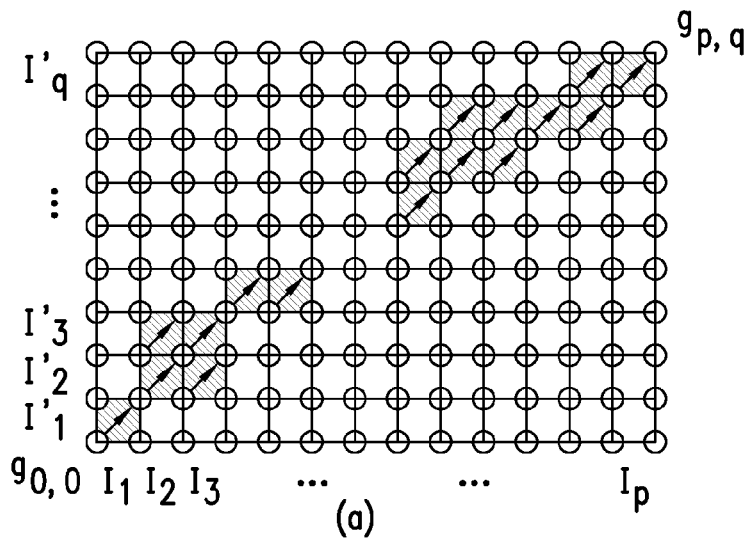
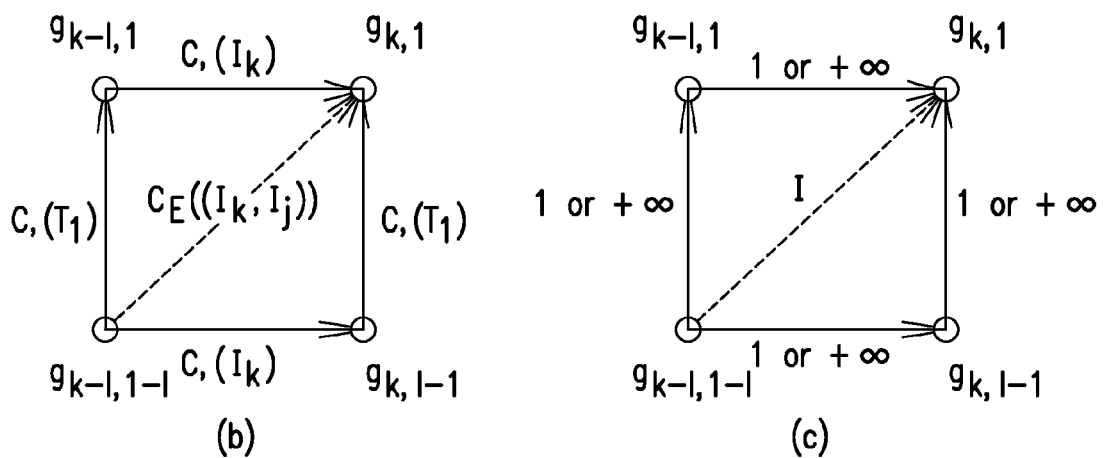
FIG.32

Table 1

| Tumor Type | IM Size (cm x cm) | Maximum Height | Execution Time (min) | Tradeoff Table | | | | | |
|---|---|---|---|---|---|---|---|---|---|
| Brain | 5 x 7 | 5 | 6 | # | 11 | 12 | 13 | 15 | 17 |
| | | | | c | 19 | 15 | 13 | 10 | 8 |
| | | | | t | 1.28 | 1.40 | 1.51 | 1.75 | 2.00 |
| Head and Neck | 11 x 12 | 5 | 15 | # | 7 | 12 | 17 | 22 | 27 |
| | | | | c | 74 | 41 | 33 | 28 | 26 |
| | | | | t | 0.81 | 1.40 | 2.00 | 2.57 | 3.15 |
| Esophagus | 8 x 17 | 5 | 36 | # | 17 | 28 | 40 | 52 | 64 |
| | | | | c | 1.29 | 97 | 84 | 72 | 64 |
| | | | | t | 2.00 | 3.27 | 4.67 | 6.06 | 7.47 |
| Pancreas | 10 x 10 | 5 | 25 | # | 7 | 10 | 14 | 20 | 25 |
| | | | | c | 72 | 52 | 38 | 31 | 28 |
| | | | | t | 0.81 | 1.16 | 1.63 | 2.33 | 2.91 |
| Prostate | 15 x 16 | 5 | 110 | # | 21 | 30 | 40 | 50 | 64 |
| | | | | c | 215 | 182 | 161 | 146 | 137 |
| | | | | t | 2.45 | 3.50 | 4.67 | 5.83 | 7.47 |

FIG. 38

Table 2

| Tumor Type | | Brain | Head and Neck | Esophagus | Pancreas | Prostate | |
|---|---|---|---|---|---|---|---|
| No. of IMs | | 5 | 7 | 7 | 7 | 5 | 7 |
| IM Size (in cm) | | 5 x 7 | 11 x 12 | 8 x 17 | 10 x 10 | 9 x 9 | 15 x 16 |
| Maximum Height | | 5 | 5 | 5 | 5 | 5 | 5 |
| No. of B-segments | X.V. | 42 | 79 | 64 | 70 | 39 | 100 |
| | SLS | 39 | 70 | 61 | 59 | 37 | 95 |

FIG. 39

Table 3

| Tumor Type | | Brain | Head and Neck | Esophagus | Pancreas | Prostate | |
|---|---|---|---|---|---|---|---|
| No. of IMs | | 5 | 7 | 7 | 7 | 5 | 7 |
| IM Size (in cm) | | 5 x 7 | 11 x 12 | 8 x 17 | 10 x 10 | 9 x 9 | 15 x 16 |
| Maximum Height | | 5 | 5 | 5 | 5 | 5 | 5 |
| No. of B-segments | X.V. | 29 | 53 | 48 | 52 | 29 | 72 |
| | SLS | 27 | 53 | 41 | 50 | 27 | 66 |

FIG. 40

Table 4

| Algorithm | $IM_1$ | $IM_2$ | $IM_3$ | $IM_4$ | $IM_5$ | $IM_6$ | $IM_7$ | Total | Execution Time | Error |
|---|---|---|---|---|---|---|---|---|---|---|
| CORVUS 5.0 | 45 | 35 | 31 | 40 | 41 | 30 | 40 | 262 | 1 second | 0 |
| XV [20] | 35 | 26 | 28 | 30 | 35 | 28 | 34 | 216 | 1 second | 5.5% |
| $SLS^1$ [9] | 20 | 15 | 15 | 17 | 24 | 18 | 22 | 131 | 1 minute | 6.2% |
| $SLS^2$ [8] | 20 | 15 | 16 | 21 | 25 | 18 | 23 | 138 | 6 hours 40 minutes | 0 |
| SLSWNE | 20 | 15 | 16 | 21 | 25 | 18 | 23 | 138 | 3 minutes 55 seconds | 0 |

FIG. 41

Table 5

| IM | $IM_1$ | $IM_2$ | $IM_3$ | $IM_4$ | $IM_5$ | $IM_6$ | $IM_7$ |
|---|---|---|---|---|---|---|---|
| Number of MLC-apertures by SLSWNE | 20 | 30 | 19 | 29 | 24 | 29 | 25 |
| Error of SLS [8] | 1.5% | 1.0% | 1.0% | 1.0% | 1.4% | 1.7% | 1.2% |

ERROR CONTROL IN ALGORITHMIC APPROACH TO STEP-AND-SHOOT INTENSITY MODULATED RADIATION THERAPY

CROSS-REFERENCE TO RELATED APPLICATIONS

This application makes reference to and claims priority to U.S. Provisional Patent Application No. 60/554,902, entitled "Method to Construct Radiation Intensity Distributions Using Uniform Fields for Radiation Therapy," filed Mar. 22, 2004, and to concurrently filed U.S. patent application Ser. No. 11/085,510, entitled "Segmentation Algorithmic Approach to Step-and-Shoot Intensity Modulated Radiation Therapy," the entire contents and disclosure of which are hereby incorporated by reference.

GOVERNMENT INTEREST STATEMENT

The United States Government has rights in this invention pursuant to Grant No. CCR-9988468 with the National Science Foundation.

BACKGROUND

1. Field of the Invention

The present invention relates generally to intensity modulated radiation therapy (IMRT), and more particularly, to a segmentation algorithmic approach to IMRT.

2. Related Art

The 3-D static leaf sequencing (SLS) problem arises in radiation therapy for cancer treatments, aiming to deliver a radiation dose prescription to a target tumor both accurately and efficiently. However, a problem with existing radiation therapy treatments is machine delivery error. Because there is an inverse relationship between machine delivery error and treatment time, there exists a need for method that can efficiently determine the tradeoff between machine delivery error and treatment time in radiation therapy treatments. Also, for radiation therapy treatments where the problem of machine delivery error is far more important than treatment time, there exists a need for a method that can eliminate machine delivery error in other radiation therapy treatments.

SUMMARY

According to a first broad aspect of the present invention, there is provided a method comprising the following steps: (a) partitioning an intensity modulated beam into a set of sub-IMBs; and (b) partitioning the sub-IMBs into segments, wherein steps (a) and (b) introduce no machine delivery error.

According to a second broad aspect of the invention, there is provided a method comprising the following steps: (a) recursively partitioning an intensity modulated beam into plateaus; and (b) partitioning the plateaus into segments, wherein step (a) comprises determining a tradeoff between machine delivery error and the number of segments into which the plateaus will be partitioned in step (b).

According to a third broad aspect of the invention, there is provided a method comprising the following steps: (a) recursively partitioning an intensity modulated beam into plateaus; (b) partitioning the plateaus into segments, wherein step (a) comprises determining a tradeoff between machine delivery error and the number of segments into which the plateaus will be partitioned in step (b); and (c) linking the segments to thereby reduce the number of segments.

According to a fourth broad aspect of the invention, there is provided a method comprising the following steps: (a) partitioning an intensity modulated beam into a set of sub-IMBs; (b) partitioning the sub-IMBs into segments, wherein steps (a) and (b) introduce no machine delivery error; and (c) linking the segments to thereby reduce the number of segments.

According to a fifth broad aspect of the invention, there is provided a method comprises the following steps: (a) generating a canonical delivery option for each set of field opening endpoints for a an intensity modulated beam; (b) for every two consecutive intensity modulated beam columns of the intensity modulated beam, determining a series of minimum cost g-matchings between the canonical delivery options of the intensity modulated beam columns; (c) determining the tradeoff curves based on the g-matchings; and (d) extracting the segments for the intensity modulated beam based on the matched field openings of the canonical delivery options from the determined g-matchings in an increasing order of consecutive intensity modulated beam columns to thereby partition the intensity modulate beam.

According to a sixth broad aspect of the invention, there is provided a method comprises the following steps: (a) generating a canonical delivery option for each set of field opening endpoints for a an intensity modulated beam; (b) for every two consecutive intensity modulated beam columns of the intensity modulated beam, determining maximum matchings with no machine delivery error between the canonical delivery options of the intensity modulated beam columns; and (c) extracting the segments for the intensity modulated beam based on the matched field openings of the canonical delivery options from the determined matchings in an increasing order of consecutive intensity modulated beam columns to thereby partition the sub-IMB.

BRIEF DESCRIPTION OF THE DRAWINGS

The invention will be described in conjunction with the accompanying drawings, in which:

FIG. 1 is an example of a intensity map;

FIG. 2 is a schematic drawing of a multileaf collimator (MLC), where the shaded rectangles represent the MLC leaves which can move up and down (as indicated by the arrows) to form an MLC-aperture, and the unshaded rectangles represent the backup diaphragms that form a bounding box of the MLC-aperture created by the MLC leaves;

FIG. 3 is an intensity map (IM);

FIGS. 4 and 5 are geometric interpretations of the two MLC-apertures (each delivering a unit radiation dose) for the delivery of the IM of FIG. 3;

FIG. 6 shows the laying of the MLC-aperture in FIG. 5 (made of dark cubes) on top of the MLC aperture in FIG. 4 (made of light cubes;

FIG. 32 is a grid graph and diagrams illustrating the edges of the grid graph;

FIG. 38 is a Table showing SLS vs. Xia and Verhey's algorithm on a Siemens™ model;

FIG. 39 is a table showing SLS vs. Xia and Verhey's algorithm on a Varian™ model;

FIG. 40 is a table providing comparison results on the number of MLC-apertures, execution time, and error for various algorithms and for an algorithm in accordance with one embodiment of the present invention; and FIG. 41 is a table providing comparison results on a head and neck cancer prescription based on an algorithm in accordance with one embodiment of the present invention.

DETAILED DESCRIPTION

Figure 9:
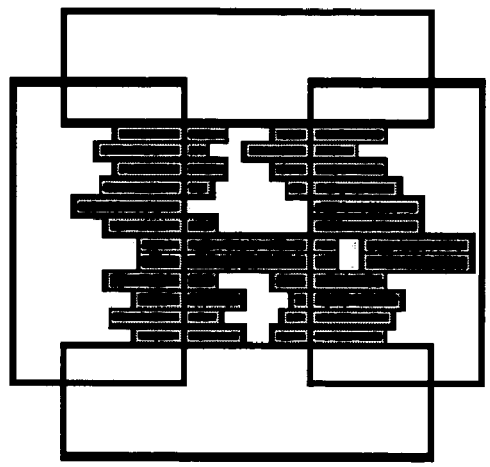
FIG. 9 is a schematic diagram showing the constraints of a Varian™ MLC.

It is advantageous to define several terms before describing the invention. It should be appreciated that the following definitions are used throughout this application.

Definitions

Where the definition of terms departs from the commonly used meaning of the term, applicant intends to utilize the definitions provided below, unless specifically indicated.

For the purposes of the present invention, a value or property is "based" on a particular value, property, the satisfaction of a condition, or other factor, if that value is derived by performing a mathematical calculation or logical decision using that value, property or other factor.

For the purpose of the present invention, a "minimum cost flow algorithm" refers to: a minimum cost flow is related to a network which is a graph that is: (1) it is directed, i.e., for any two vertex u and v, the edge (u,v) and (v,u) is different, the edge (u,v) is said to be entering v and exiting u; (2) there are two distinct vertices, the source vertex s and the sink vertex t where there is no edge entering s and there is no edge exiting t; and (3) each edge e has a capacity that is a positive number; and (4) each edge e has a cost c(e). The cost of a flow $f$ is the sum of the cost of each edge e, which is computed as the product $f(e)c(e)$. A flow $f$ with respect to a value $f_0$ is minimum if $f \leq f_0$ and the cost of $f$ is minimized. A minimum cost flow algorithm is a method for computing a minimum cost flow with respect to a given a value $f_0$.

For the purposes of the present invention the term "sub-IMB" refers to a portion of an IMB.

For the purposes of the present invention, the term "bipartite graph" refers to a graph whose vertex set consists of two disjoint set of vertices U and V, such that all of the edges only connect the vertices from U to the vertices V.

For the purposes of the present invention, the term "bipartite matching" for a bipartite graph refers to a set of edges such that no two edges share a common vertex.

For the purposes of the present invention, the term "bipartite maximum matching" refers to a bipartite matching with the most number of edges.

For the purposes of the present invention, the term "bipartite maximum matching algorithm" refers to a method for computing a bipartite maximum matching.

For the purposes of the present invention, the term "canonical delivery option" refers to: A delivery option of an intensity profile is a set of field-openings (FOs) together with an intensity level of one that created it. Mathematically, each field-opening can be viewed as a closed interval on the real line [l, r]. Hence a delivery option can be viewed as a set of intervals on the real line, e.g., $[l_1, r_1], [l_2, r_2], \ldots, [l_k, r_k]$. A delivery option is canonical if none of its intervals is strictly contained in the interior of another interval of it.

For the purposes of the present invention, the term "cost of a bipartite matching" refers to the sum of the cost of the edges that is in the matching.

For the purposes of the present invention, the term "cost of a path cover" refers to the sum of the edge costs that is in the path cover.

For the purposes of the present invention, the term "FO-endpoint" refers to a field opening endpoint. Mathematically, a field-opening can be viewed as a closed interval [l, r] on the real line. In this context, the FO-end point refers to the numbers l and r.

For the purposes of the present invention, the term "g-matching" or "g-bipartite matching" refers to a bipartite matching with g number of edges.

For the purposes of the present invention, the term "g-path over" refers to a path cover with g number of paths.

For the purposes of the present invention, the term "graph algorithm techniques" refers to techniques that use graph data structures to model and solve problems.

For the purposes of the present invention, the term "graph" refers to a discrete data structure used to model complex relationships among objects and consists of vertices and edges connecting the vertices.

For the purposes of the present invention, the term "IMB column" refers to a column of the matrix that corresponds to an IMB.

For the purposes of the present invention, the term "intensity map" refers to an intensity-modulated beam (IMB).

For the purposes of the present invention, the term "intensity modulated beams" or "IMB" refers to the prescribed discrete fluence distributions of radiation. An IMB along a given direction in 3-D is specified by a set of nonnegative integers on a 2-D grid.

For the purposes of the present invention, the term "intensity profile" refers to a row of the matrix that corresponds to an IMB.

For the purposes of the present invention, the term "leaf sequence" refers to a set of segments that creates a given set of IMBs.

For the purposes of the present invention, the term "maximum-flow algorithm" refers to: A graph is called a network if: (1) it is directed, i.e., for any two vertex u and v, the edge (u,v) and (v,u) is different, the edge (u,v) is said to be entering v and exiting u; (2) there are two distinct vertices, the source vertex s and the sink vertex t where there is no edge entering s and there is no edge exiting t; and (3) each edge has a capacity that is a positive number. A flow is a function $f$ on the edges of a network that satisfies the following two condition: (1) for any edge e, $f(e)$ is less than the capacity of e and (2) for any vertex v that is neither s nor t, the total flow entering it, i.e., the sum of the flow values on the edges directing at v, is equal to the total flow exiting v, i.e., the sum of the flow values on the edges exiting v. The value of a flow function $f$ is the total flow values on the edges exiting the source vertex s. A flow function $f$ is a maximum flow, if the value of the flow function is the maximum among all the flow functions. A maximum-flow algorithm is a method for finding a maximum flow on a network.

For the purposes of the present invention, the term "minimum cost g-matching" refers to a g-matching with the minimum amount of cost.

For the purposes of the present invention, the term "minimum cost g-path cover" refers to a path cover whose cost is the minimum among all g-path covers.

For the purposes of the present invention, the term "mixed partitioning scheme" refers to a way to partition an IMB into sub-IMBs using more than one partitioning method in a dynamic programming fashion.

For the purposes of the present invention, the term "multi-leaf collimator" or "MLC" refers to a device for delivering intensity modulated beams consisting of multiple pairs of tungsten leaves of approximately the same rectangular shape and size. Opposing MLC leaves of each pair are aligned with each other. The leaves may move up and down to form a rectilinear polygonal region that is monotone to, for example, the x-axis.

For the purposes of the present invention, the term "mutually disjoint" refers to two geometric curves that do not intersect each other.

For the purposes of the present invention, the term "path cover" of a graph refers to a set of paths such that each vertex in the graph is on one and only one path.

For the purposes of the present invention, the term "plateau" refers to sub-IMB having a height of 0 or d, where d is a positive number less than the height of the IMB of which the sub-IMB is a portion.

For the purposes of the present invention, the term "segment" refers to an MLC-aperture shape formed by MLC leaves, together with intensity levels, which are delivered by the MLC-aperture.

For the purposes of the present invention, the term "segmentation algorithm" refers generally to an algorithm that finds a minimum number of segments that creates a given intensity-modulated beam (IMB).

For the purposes of the present invention, the term "shortest-path algorithm" refers to: A path in a graph from vertex $v_1$ to $v_k$ is a sequence of vertices $v_1, v_2, \ldots, v_k$ that are connected by the edges $(v_1, v_2), (v_2, v_3), \ldots, (v_{k-1}, v_k)$. (The edges are also considered to be part of the path.) When the each edge in the graph has a cost (a real number) that is associated with it, the graph is said to be a weighted graph. The cost of a path in a weighted graph is the total sum of its edge costs. A shortest path between two vertices u and v of a weighted graph is a path between u and v with the minimum cost. A shortest path algorithm is a method for finding a shortest path between two vertices in a weighted graph.

For the purposes of the present invention, the term "Steiner point" refers to a way in which a field-opening [l, r] is split into two new field openings [l,x] and [x,r], with l<x<r.

For the purposes of the present invention, the term "step-and-shoot" refers to a static IMRT method in which the MLC leaves stay stationary during irradiation, and move to reshape the beam while the radiation is not present.

For the purposes of the present invention, the term "z-post" refers to intensity level of each grid cell of an IMB.

For the purposes of the present invention, when referring to a grid cell, the term "intensity level" refers to the number in the grid cell which correlates to the amount (in unit) of radiation to be delivered by the IMB to the body region corresponding to that cell.

For the purposes of the present invention, the term "treatment plan" for a given IM consists of a set of MLC-apertures (together with their heights) for delivering the IM.

Description

The 3-D static leaf sequencing (SLS) problem arises in radiation therapy for cancer treatments, aiming to deliver a prescribed radiation dose to a target tumor accurately and efficiently. The treatment time and machine delivery error are two crucial factors to the solution (i.e., a treatment plan) for the SLS problem. In one embodiment, the present invention provides a method for determining the tradeoff between the treatment time and machine delivery error also called the "tongue-and-groove" error in medical literature) for the 3-D SLS problem. In one embodiment, the method of the present invention employs a 3-D SLS algorithm with error control gives the users (e.g., physicians) the option of specifying a machine delivery error bound, and subject to the given error bound, the algorithm computes a treatment plan with the minimum treatment time. In one embodiment, the present invention addresses the SLS problem with error control by computing a k-weight shortest path in a directed graph and building the graph by computing g-matchings and minimum cost flows. Furthermore, the 3-D SLS algorithm used in one embodiment of the present invention may be used with various popular radiotherapy machine models.

The 3-D static leaf sequencing (SLS) problem arises in intensity-modulated radiation therapy (IMRT). IMRT is a modern cancer therapy technique which aims to deliver a highly conformal radiation dose to a target tumor while sparing the surrounding normal tissues and sensitive structures. Performing IMRT is based on the ability to accurately and efficiently deliver prescribed discrete dose distributions of radiation, called intensity maps (IMs). An IM is a dose prescription specified by a set of nonnegative integers on a uniform 2-D grid, see FIG. 1. The value in each grid cell indicates the amount (in units) of radiation to be delivered to the body region corresponding to that IM cell. One of the most advanced tools today for delivering intensity maps is the multileaf collimator (MLC). An MLC consists of up to 60 pairs of tungsten alloy leaves of the same rectangular shape and size (see FIG. 2). The opposing leaves of a pair are aligned to each other. The leaves can move up and down to form a rectilinear region, called an MLC-aperture, which is monotone to (say) the x-axis. To further reduce radiation leakage, two pairs of backup metal diaphragms (along the x and y axes) are used to form a "bounding box" of each rectilinear MLC-aperture. The cross-section of a cylindrical radiation beam (produced by a radiation machine) is shaped by an MLC-aperture to deliver a uniform dose to (a portion of) an IM. Each MLC-aperture may be assumed to be associated with an integer representing the units of radiation delivered by the aperture.

Currently, there are three popular MLC systems that are used for clinical cancer treatment. The systems are the Elekta™, Siemens™, and Varian™ MLCs. Depending on the actual MLC system in use, there are some differences among the geometric shapes of the rectilinear x-monotone regions that can be formed by the respective MLC. The details on the differences among these MLC systems will be described below. There are several techniques for delivering IMRT using an MLC, such as those described in S. Webb. *The Physics of Three-Dimensional Radiation Therapy*. Bristol, Institute of Physics Publishing, 1993 and 39. S. Webb. *The Physics of Conformal Radiotherapy Advances in Technology*. Bristol, Institute of Physics Publishing, 1997, the entire contents and disclosures of which are hereby incorporated by reference. The most popular technique may be one called the static leaf sequencing (SLS) or the "step-and-shoot" technique. In the SLS approach, an IM is delivered as follows:

(1) Form an MLC-aperture.
(2) Turn on the beam source and deliver a uniform dose of radiation to the area of the IM exposed by the MLC-aperture.
(3) Turn off the beam source.
(4) Reposition the MLC leaves to form another MLC-aperture, and repeat steps 2-4 until the entire IM is done.

FIG. 3 shows an IM used in the description of static leaf sequencing below. FIGS. 4 and 5 are geometric interpretations of the two MLC-apertures (each delivering a unit radiation dose) for the delivery of the IM of FIG. 3. FIG. 6 shows the laying of the MLC-aperture in FIG. 5 (made of dark cubes) on top of the one in FIG. 4 (made of light cubes) and shows that some of the cubes of the MLC-aperture in FIG. 5 drop to the first level as if they were pulled down by gravity.

In SLS, the boundary of each MLC-aperture does not intersect the interior of any IM cell. In delivering a beam shaped by an MLC-aperture, all the cells inside the region of the MLC-aperture receive the same integral amount of radiation dose (say, one unit), i.e., the numbers in all such cells are decreased by the same integer value. The IM is done when each cell has a value zero. Intuitively, it is possible to view the above process as playing the following game: An IM is a 3-D "mountain" made of unit cubes, (see FIG. 6), and each MLC-aperture corresponds to a special "plateau," whose uniform height is the amount of radiation it delivers; the goal is to "build" this mountain by stacking up a set of such plateaus, see for example FIGS. 4, 5 and 6). It is important to note that each plateau, like the 3-D IM mountain, is not one whole "rigid" object, i.e., it is made of unit cubes as well. Thus, when two plateaus are "stacked" together, some of the cubes may fall to lower positions as if they were pulled down by gravity. Geometrically, the 3-D SLS problem is to partition a 3-D IM "mountain" into such plateaus of uniform heights.

A treatment plan for a given IM consists of a set of MLC-apertures (together with their heights) for delivering the IM. Two key criteria are used to evaluate the quality of an IMRT treatment plan:

(1) Treatment time (the efficiency): Minimizing the treatment time is important because it not only lowers the treatment costs but also increases the patient throughput. Since the overhead associated with turning the beam source on/off and repositioning MLC leaves dominates the total treatment time, in one embodiment, the method the present invention minimizes the number of MLC-apertures used for delivering an IM.

(2) Machine delivery error (the accuracy): In one embodiment of the present invention, an IM is partitioned into a set of MLC-apertures that perfectly builds the 3-D IM mountain. However, in reality, due to the special geometric shape of the MLC leaves, an MLC-aperture may not be delivered as perfectly as its geometry. This gives rise to an error between the prescribed dose and actually delivered dose. This error, referred to herein, is the machine delivery error, also called the "tongue-and-groove" error in medical literature. The nature of the machine delivery error is discussed in more detail below. Minimizing the machine delivery error is important because according to a recent study, the maximum machine delivery error can be up to 10% in point dose, which is well beyond the allowed 3-5% limit. Although the machine delivery error cannot be entirely eliminated, carefully choosing MLC-apertures may reduce the error.

The 3-D static leaf sequencing (SLS) problem is: Given an IM and an error bound E, find a set S of MLC-apertures for delivering the IM such that the total machine delivery error incurred by S is ≦E, and the size |S| is minimized. Note one key to this 3-D SLS problem is to find a good tradeoff between the accuracy (error) and efficiency (treatment time).

The 3-D SLS problem has received a great deal of attention from several research communities. In the medical physics community, many heuristic algorithms for the SLS problem have been proposed. A method for solving the 3-D SLS problem without error control (i.e., the machine delivery error is ignored) is described by Xia and Verhey in the paper, P. Xia et al., "MLC Leaf Sequencing Algorithm for Intensity Modulated Beams with Multiple Static Segments" in *Med. Phys.,* 25:1424-1434, 1998, the entire contents and disclosure of which is hereby incorporated by reference. Xia and Verhey's algorithm has been implemented by many researchers and used as a widely accepted benchmark program for leaf sequencing software. However, none of these SLS heuristics can guarantee a good quality of their output solutions.

In computational geometry, Chen et al., "Geometric Algorithms for Static Leaf Sequencing Problems in Radiation Therapy" in *International Journal of Computational Geometry and Applications,* 14(5):311-339, 2004 (hereinafter "Chen et al. I" paper), Chen et al., "Optimal Terrain Construction Problems and Applications in Intensity-Modulated Radiation Therapy" in *Lecture Notes in Computer Science, Springer-Verlag, Proc.* 10*th Annual European Symposium on Algorithms*, volume 2461, pages 270283, 2002 (hereinafter "Chen et al. II" paper), Luan et al., "A New Leaf Sequencing Algorithm/Software for Step and Shoot IMRT. *Med. Phys.,* 30(6):1404, 2003 and Luan et al. "A New MLC Segmentation Algorithm/Software for Step and Shoot IMRT. *Med. Phys.,* 31(4):695-707, 2004, the entire contents and disclosures of which are hereby incorporated by reference herein, provided geometric algorithms for the 3-D SLS problem on the Elekta™ model without error control. The software for the algorithms is currently used in two hospitals for clinical cancer treatments and these algorithms are described below.

In the operations research community, two variations of the 3-D SLS problem, the MLC problem with minimum beam-on time and MLC problem with minimum beam-on time plus machine setup time, have been studied. Here, the beam-on time refers to the total amount of time when a patient is actually exposed to radiation, and the machine setup time refers to the time associated with turning on/off the radiation source and repositioning MLC leaves. The MLC problem with minimum beam-on time is polynomial time solvable, while the MLC problem with minimum beam-on time plus machine setup time is NP-hard. There appear to be no efficient algorithms for the MLC problem with minimum beam-on time plus machine setup time.

In some situations, the goal for the 3-D SLS problem is to minimize the number of MLC-apertures used for delivering an IM. However, the MLC problem with minimum beam-on time plus machine setup time seems more general, and the formulation of the 3-D SLS problem as addressed by one embodiment of the present invention also well captures the total treatment time. This is because the machine setup time for the MLC-apertures dominates the total treatment time and algorithms that minimize the number of MLC-apertures used are desired to reduce the treatment time.

Although it is a very important problem, much less work has been done on the 3-D SLS problem with machine delivery error control. In fact, none of the known approaches can systematically control the machine delivery error so far (i.e., determining a good tradeoff between the error and time).

In one embodiment, the present invention takes advantage of the discovery that that the 3-D SLS problem is NP-hard even for the case in which the given IM consists of only one column of cells. This implies that the versions of the 3-D SLS problem under each of the three popular MLC models, with or without machine delivery error control, are all NP-hard, as described in more detail below.

In one embodiment, the present invention takes advantage of the first ever modeling of the 3-D SLS problem with a tradeoff between the error and treatment time and an efficient algorithm for the problem on the Elekta™ model. In one solution, employed by one embodiment of the present invention, the 3-D SLS problem is formulated as a k-weight shortest path problem on a directed graph, in which each edge is defined by a minimum weight g-cardinality matching. Every such k-weight path specifies a set S of k MLC-apertures for delivering the given IM, and the cost of the path indicates the machine delivery error of the set S of MLC-apertures.

In one embodiment, the present invention provides methods that allow a 3-D SLS algorithm that to be used with various MLC models, such as Siemens™ and Varian™. These methods are based on computing a minimum g-path cover of a directed acyclic graph.

In one embodiment, the present invention provides a method for solving the 2-D case of the 3-D SLS problem in which the given IM consists of entries of only 1 or 0 (i.e., partitioning a polygonal domain into a minimum set of special x-monotone polygons). The solution used in the method is based on computing a minimum cost flow in a special graph.

Three popular MLC systems and their constraints, the machine delivery errors associated with IMRT treatments using such MLC systems, and the SLS problem and its variations will now be described.

As mentioned above, there are three popular MLC systems currently used in clinical treatments: the Elekta™, Siemens™, and Varian™ MLC systems. The mechanical structure of these MLCs, although quite flexible, is not perfect in that it still precludes certain aperture shapes from being used for treatment. One such constraint is called the minimum leaf separation (e.g., on the Elekta™ or Varian™ MLC), which requires the distance between the opposing leaves of any MLC leaf pair to be no smaller than a given value δ (e.g., δ=1 cm). Another common constraint is called the no-interleaf motion (e.g., on the Elekta™ or Siemens™ MLC), which forbids the tip of each MLC leaf to surpass those of its neighboring leaves on the opposite leaf bank. These constraints prevent opposing MLC leaves from colliding into each other and being damaged.

Figure 8:
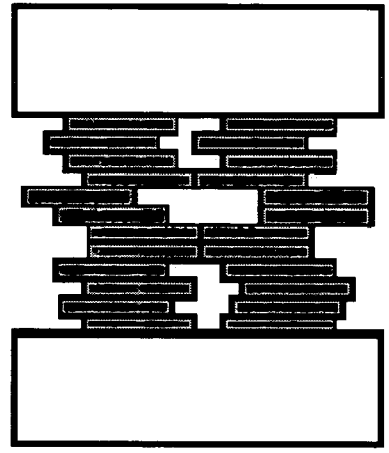
FIG. 8 is a schematic diagram showing the constraints of a Siemens™ MLC.
Figure 7:
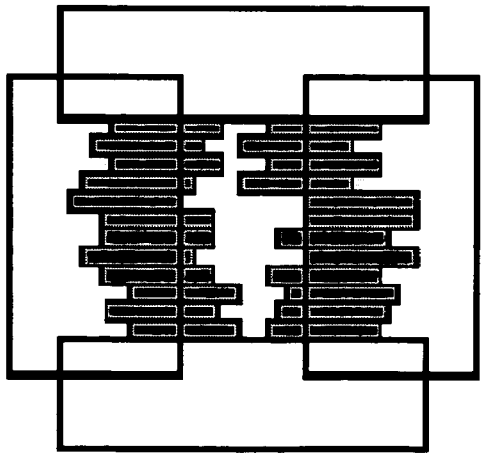
FIG. 7 shows the constraints of an Elekta™ MLC.

FIGS. 7, 8 and 9 shows the constraints of these MLC systems: the Elekta™ MLC, the Siemens™ MLC, and the Varian™ MLC, respectively. The shaded rectangles represent the MLC leaves, and the unshaded rectangles represent the backup diaphragms which form a bounding box of an MLC-aperture. Note that unlike the Elekta™ and Varian™ MLCs, the Siemens™ MLC only has a single pair of backup metal diaphragms.

The Elekta™ MLC is subject to both the minimum leaf separation and no-interleaf motion constraints (see FIG. 7). The Siemens™ MLC is subject to only the no-interleaf motion constraint (see FIG. 8). Hence, a degenerate rectilinear x-monotone polygon can be formed by the Siemens™ MLC, by closing some leaf pairs (see FIG. 8). The Varian™ MLC is subject to the minimum leaf separation constraint, but allows interleaf motion (see FIG. 9). Thus, to "close" a leaf pair in the Varian™ system, it is possible to move the leaf opening under the backup diaphragms (see FIG. 9). But, the Elekta™ MLC cannot "close" its leaf pairs in a similar manner due to its no-interleaf motion constraint. Geometrically, on the Elekta™, each MLC-aperture is a rectilinear x-monotone simple polygon whose minimum vertical "width" is no smaller than the minimum separation value A, while on the Siemens™ or Varian™, an MLC-aperture can be a degenerate x-monotone polygon (i.e., with several connected components).

Figure 12:
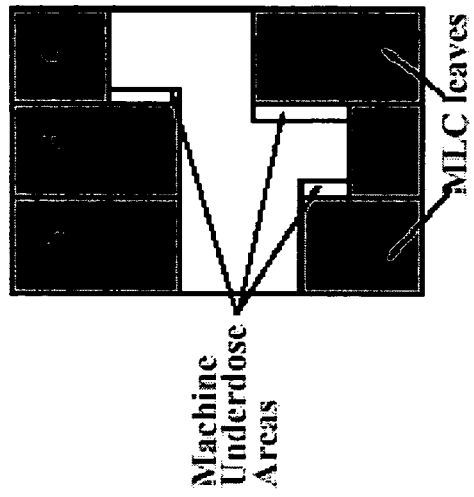
FIG. 12 is a schematic diagram showing the underdose and leakage areas of the tongue-and-groove feature on an MLC-aperture region of the MLC of FIG. 10.
Figure 11:
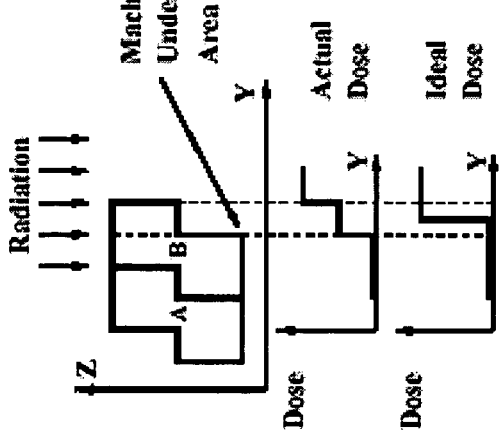
FIG. 11 is a schematic diagram showing the underdose and leakage areas
Figure 10:
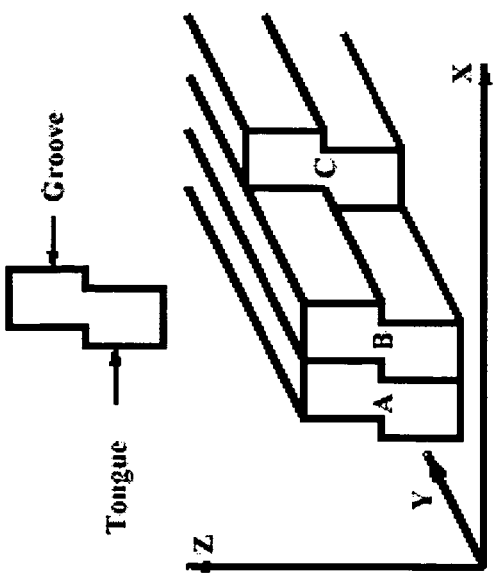
FIG. 10 is a schematic diagram illustrating the tongue-and-groove (TG) interlock feature of the MLC in 3-D, where leaf B is used for blocking radiation.

FIG. 10 illustrates the tongue-and-groove (TG) interlock feature of the MLC in 3-D, where leaf B is used for blocking radiation. As shown in FIG. 11, when leaf B is used for blocking radiation, there is an underdose and leakage in the tongue or groove area. FIG. 12 shows the underdose and leakage areas of the tongue-and-groove feature on an MLC-aperture region.

On most current MLCs, the sides of the leaves are designed to have a "tongue-and-groove" (TG) interlock feature (see FIG. 10). This design reduces the radiation leakage through the gap between two neighboring MLC leaves and minimizes the friction during leaf movement. However, it also causes an unwanted underdose and leakage situation when an MLC leaf is used for blocking radiation (see FIGS. 11 and 12). Geometrically, the underdose and leakage error caused by the tongue-and-groove feature associated with an MLC-aperture is a set of 3-D axis-parallel boxes w·$l_i$·$h_i$, where w is the (fixed) width of the tongue or groove side of an MLC leaf, $l_i$ is the length of the portion of the i-th leaf that is actually involved in blocking radiation, and h=a·r is the amount of radiation leakage with a being the (fixed) leakage ratio and r being the amount of radiation delivered by that MLC-aperture. FIG. 11 illustrates the height of the underdose and leakage error, and FIG. 12 illustrates the width and length of the underdose and leakage error.

There are at least two types of errors caused by the tongue-and-groove feature of MLC leaves:

(1) Tongue-or-groove error: The tongue-or-groove error of an MLC-aperture is defined as the amount of underdose and leakage error that occurs whenever the tongue side or groove side of an MLC leaf is used for blocking radiation. The tongue-or-groove error of an IMRT plan (i.e., a set of MLC-apertures) is the sum of the tongue-or-groove errors of all its MLC-apertures.

(2) Tongue-and-groove error: Unlike the tongue-or-groove error which is defined "dip" in the final dose distribution where a tongue-and-groove error occurs, on each individual MLC-aperture, the tongue-and-groove error is defined by the relations between different MLC-apertures. The tongue-and-groove error occurs whenever the tongue side of an MLC leaf and the corresponding groove side of its neighboring leaf are both used for blocking radiation in any two different MLC-apertures of an IMRT plan (see FIGS. 13 and 14, described below). Clearly, the tongue-and-groove error is a subset of the tongue-or-groove error. Minimizing the tongue-and-groove error is also important because it usually occurs in the middle of the delivered intensity maps, causing insufficient dose coverage to the tumor and is actually the most damaging part of the tongue-or-groove error.

Figure 16:
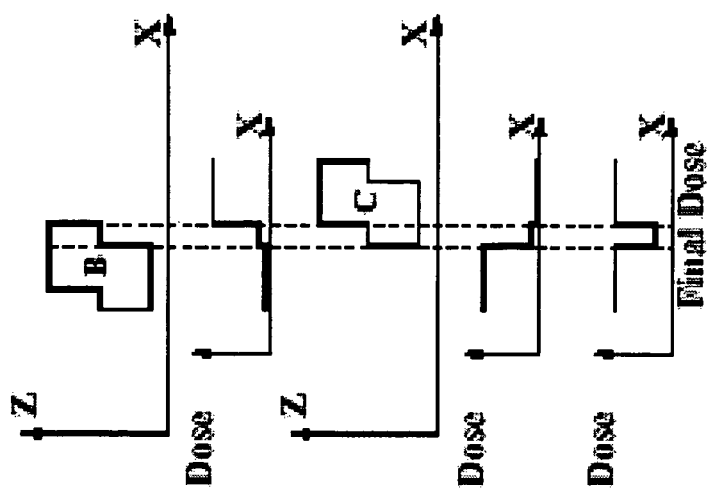
FIG. 16 is a schematic diagram illustrating a dose "dip" in the final dose distribution where a tongue-and-groove error occurs.
Figure 15:
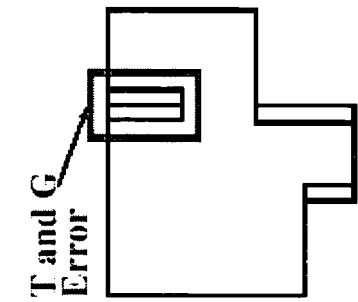
FIG. 15 is a schematic diagram illustrating the delivering of two MLC apertures in FIGS. 13 and 14, one by one.
Figure 14:
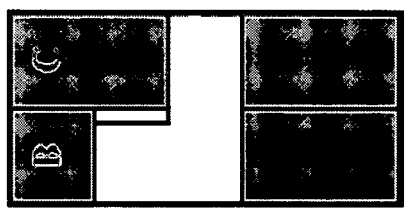
FIG. 14 is a schematic diagram illustrating a tongue-and-groove error.
Figure 13:
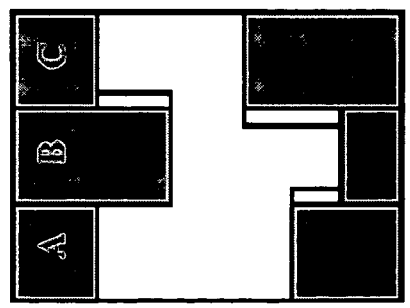
FIG. 13 is a schematic diagram illustrating a tongue-and-groove error.

FIGS. 13 and 14 illustrate examples of tongue-and-groove error. Two MLC-apertures (the shaded rectangles represent MLC leaves). When delivering the two MLC-apertures in FIGS. 13 and 14 (one by one), the groove side of leaf B and tongue side of leaf C are both used for blocking radiation, causing a tongue-and-groove error in the area between the leaves B and C, as shown in FIG. 15. FIG. 16 illustrates a dose, geometrically, for a set of MLC-apertures, the errors caused by using the tongue sides of the MLC leaves for blocking radiation are a set of 3-D axis-parallel boxes, denoted by $V_T$, possibly stacked up in the fashion as in FIG. 6. Similarly, the errors caused by using the groove sides of the leaves for blocking radiation are another set of (possibly stacked up) 3-D axis-parallel boxes, denoted by $V_G$. Then the tongue-or-groove error for the MLC-aperture set is the sum of the volume values of these two sets (i.e., $|V_T|+|V_G|$, and the tongue-and-groove error is equal to twice the volume value of the intersection between $V_T$ and $V_G$ (i.e., $2 \cdot |V_T \cap V_G|$). (Note that the existence of a non-empty intersection between $V_T$ and $V_G$ implies that the tongue side of some MLC leaf and the corresponding groove side of its neighboring leaf do block radiation in the IMRT plan.) It is also possible to view the given IM as a 3-D rectilinear terrain (mountain), denoted by V*. Then the magnitude of the tongue-or-groove (resp., tongue-and-groove) error can be quantified by the percentage $$\frac{|V_T|+|V_G|}{|V^*|}\left(resp., \frac{|V_T| \cap |V_G|}{|V^*|}\right).$$

Further, if each MLC-aperture is viewed as a rectilinear polygonal region on the xy-plane, then the tongue-or-groove error occurs along every vertical boundary edge of this region.

More precisely, the 3-D static leaf sequencing (SLS) problem is: Given an IM and an error bound E, find a set S of MLC-apertures for delivering the IM, such that the machine delivery error (i.e., either the tongue-or-groove error or the tongue-and-groove error) is E and the size |S| is minimized.

Interchangeably, such MLC-apertures are referred to as B-segments (for). Each B block-segment is of a rectilinear x-monotone polygonal shape (depending on the MLC model used) of a uniform integer height h≧1 (h is the number of dose units delivered by the B-segment). When the given IM has only 1 or 0 in its cells, the 3-D SLS problem becomes a 2-D one, (i.e., the 2-D SLS problem), and an optimal set of B-segments corresponds to a minimum set of special rectilinear x-monotone polygons.

A key special case of the 3-D SLS problem, called the basic 3-D SLS problem, is also of clinical value. This case is similar to the general 3-D SLS problem, except that the height of each of its B-segments is one. Note that in the general 3-D SLS problem, the uniform height of each B-segment can be any integer≧1.

Studying the basic case is important because the maximum heights of the majority of IMs used in the current clinical treatments are around 5, and an optimal solution for the basic case on such an IM is often very close to an optimal solution for the general case.

Figure 18:
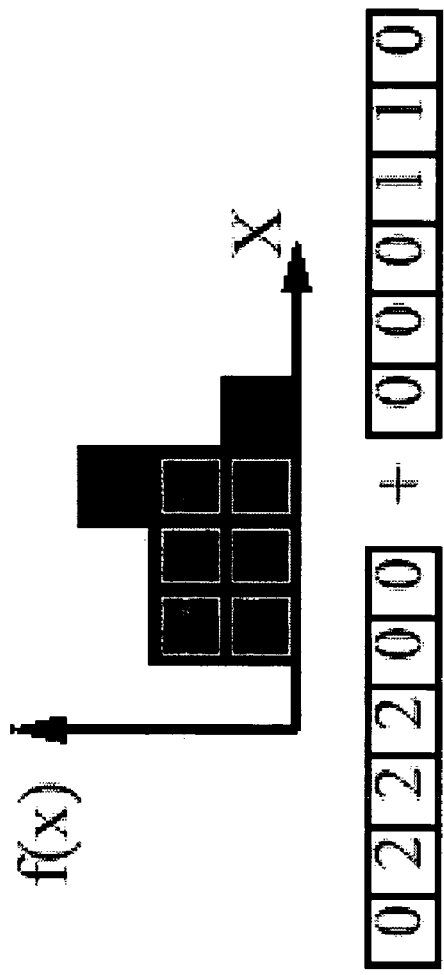
FIG. 18 is a schematic diagram illustrating illustrates that the area defined by the IM curve in FIG. 17 can be decomposed into two blocks.
Figure 17:
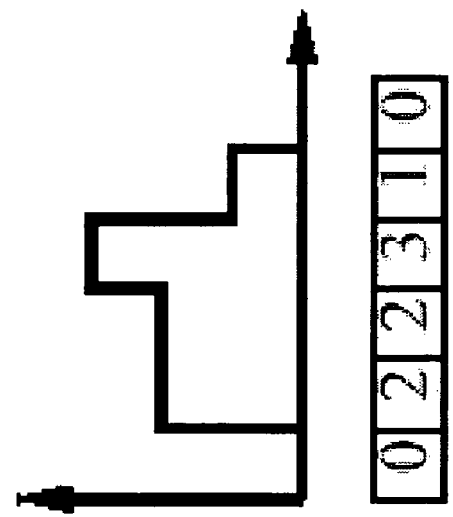
FIG. 17 is a schematic diagram illustrating the 2-D IM curve of an IM with only one column of cells.

FIGS. 17 and 18 illustrate the SLS problem in which the given IM has only one column of cells. FIG. 17 shows the 2-D IM curve of an IM with only one column of cells. (For the ease of the presentation, the IM of a single column of cells is represented by its transpose here.) FIG. 18 illustrates that the area defined by the IM curve in FIG. 17 can be decomposed into two blocks, each made of unit squares. Note that, when laying the second block (represented by the dark-shaded unit squares) on top of the first block (represented by the light-shaded unit squares), one of the unit squares of the second block falls to the lower level just as in the case of the general 3-D SLS problem.

The NP-hardness of the SLS problem may be proved for the case in which the given IM has only one column of cells, by showing a polynomial time reduction to it from the knapsack problem, which is known to be NP-complete. Since the input IM consists of only one column of cells, one may simply represent this IM by an IM curve in 2-D, which can be viewed as a rectilinear curve monotone to the x-axis (see FIG. 17).

The SLS problem seeks a decomposition of the area enclosed by the IM curve and the x-axis into a minimum set of blocks, such that each block is a rectangle made of unit squares and the IM curve can be "built" by stacking up the blocks (see FIG. 18). Note that the height of the IM curve at every x=a is an integer value, and the heights of all blocks in any decomposition of the area defined by the 2-D IM curve are also required to be integers. Given a knapsack of size K and n items of sizes $s_1, s_2, \ldots s_n$, respectively, such that K, $s_1$, $S_2, \ldots s_n$ are all integers, the knapsack problem asks whether there is a subset of these n items whose total sum of sizes is exactly K. Without loss of generality, assuming assume $s_i > 0$ for every i=1, 2, ..., n+1 (see FIG. 19), and $$0 < K, \sum_{i=1}^{n} s_i.$$

Figure 19:
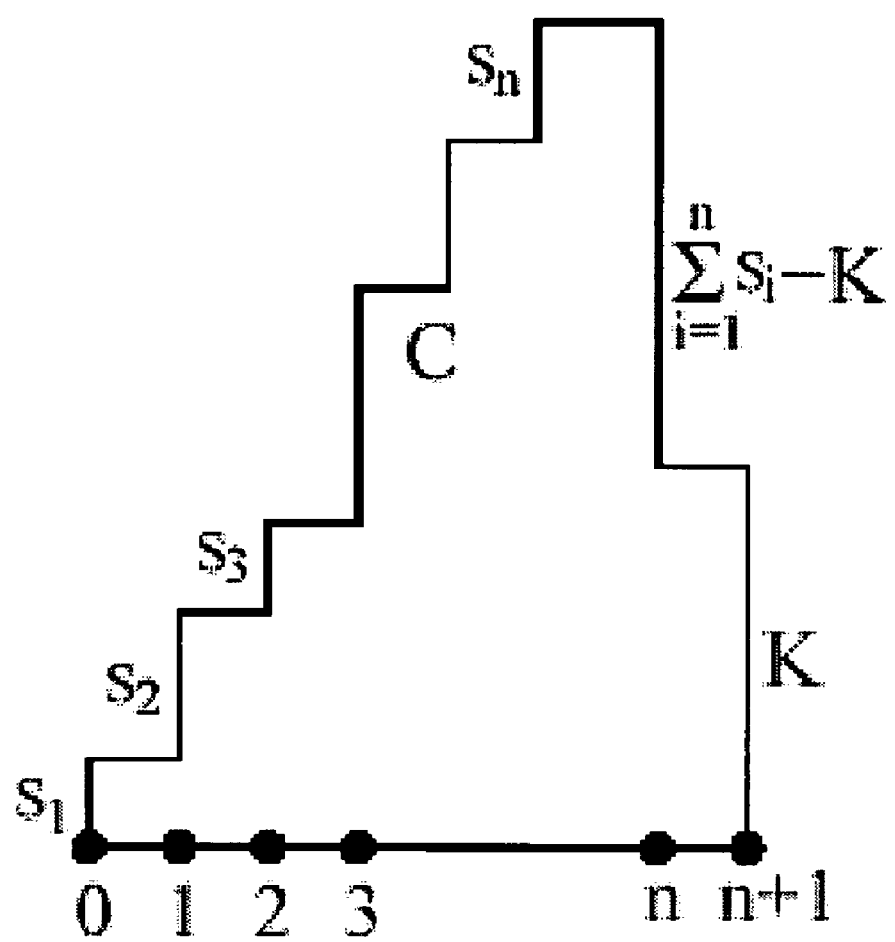
FIG. 19 is a 2-D IM curve C constructed from a knapsack problem instance.

For any instance of the knapsack problem, construct an IM curve $C=(s_1, s_1+s_2, \ldots, s_1+s_2+\ldots+s_n, K)$, in which the i-th value specifies the height of the IM curve on the interval |i−1, i| on the x-axis, for each i=1, 2, ..., n+1 (see FIG. 19). Clearly, the height of C at every x=a a is an integer. For any value a∈R, let $L_a$ (resp., $R_a$) denote the set containing all possible blocks for C whose left (resp., right) endpoint is defined by x=a. Suppose the points on the upper boundary of C are in the left-to-right order. It is easy to prove the following lemma:

Lemma 1. For any decomposition D of the 2-D IM curve C, the following holds: (1) If there is a height increase of C at x=a, then $D \cap L_a \ne \emptyset$, (2) If there is a height decrease of C at x=a, then $D \cap R_a \ne \emptyset$ (3) If there is no height change of C at x=a, then $D \cap L_a = \emptyset \Leftrightarrow D \cap R_a = \emptyset$.

For the IM curve C constructed above, there are n height increases along the left-to-right order of its upper boundary. By Lemma 1, for any decomposition D of C, $|D \cap L_a| \ge 1$ for each value a=0, 1 ... n−1. Since $$L_{a_1} \cap L_{a2} = \emptyset \text{ if } a_1 \ne a_2,$$

$$|D| \ge \left|D \cap \bigcup_{a=0}^{n-1} L_a\right| = \sum_{a=0}^{n-1} |D \cap L_a| \ge \sum_{a=0}^{n-1} 1 = n$$

implying that the size of any decomposition of C has a lower bound of n.

Let $B=|l,r|\times h$ denote a block B defined by a height h and an interval |l,r| on the x-axis.

Lemma 2. Let D* be an optimal decomposition of the 2-D IM curve C constructed above. Then |D|=n if and only if the answer to the corresponding knapsack problem is "yes".

Proof. (I) If the answer to the corresponding knapsack problem is "yes," then there is a subset of I of $\{1, 2\ldots, n\}$ such that $\Sigma_{i \in I} s_i = K$. It is easy to verify that $D=\{B_1, B_2, \ldots, B_n\}$ with $B_i=|i-1,n|\times s_i i \notin I$ or $B_i=|i-1,n+1|\times s_i i \in I$ for $I=1, 2, \ldots, n,$ is indeed a decomposition of C. Since D* is optimal, then $|D^*| \le |D| = n$. Combined with the lower bound result stated above, then $|D^*|=n$.

(II) In the other direction, suppose $|D^*|=n$. Let $D^*=\{B_1, B_2, \ldots B_n\}$ and $B_i=|l_i,r_i|\times h$ for each i=1, 2, ..., n. Further, assuming that $\{l_1, l_2, \ldots, l_n\}$ is in increasing order. By Lemma 1, it is easy to show that $L_i=i-1$, for each i=1, 2 ... n and $D^* \cap L_a \ne \emptyset \Leftrightarrow a \in \{0, 1, \ldots, n-1\}$.

First it can be shown that $r_i \in \{0, 1, \ldots, n+1\}$ for each i=1, 2, ..., n by contradiction. If not, suppose $r_j \notin \{0, 1, \ldots, n+1\}$ for some j∈{1, 2, ..., n}. Obviously, $D^* \cap L_{r_j} = \emptyset$. Since the IM curve C has no height change at $x=r_j$, by Lemma 1, then $D^* \cap R_{r_j} = \emptyset$. But this is a contradiction to the fact that $B_j=[l_j, r_j] \times h_j \in D^* \cap R_{r_j}$.

Next, transform D* is transformed to a special optimal decomposition D' of C (i.e., |D*|=|D'|=n) such that $r_i \ne l_j$ for any i,j∈{1, 2, ..., n}. D' enables a solution to be obtained for the knapsack problem.

Suppose there are p, q∈{1, 2, ..., n} such that $r_p=l_q$. Then there are three possible cases.

Case (1): $h_p=h_q$. Then $B_p=[l_p, r_p] \times h_p$ and $B_q=[l_q, r_q] \times h_q$ can be replaced by a single block $[l_p, r_q] \times h_p$, which will result in a new decomposition of a size smaller than the optimal one, a contradiction.

Case (2): $h_p > h_q$. According to the construction of the IM curve C, at $x=l_q$, there is a height increase of $s_q$. Imagine "building" C using blocks in a decomposition of C. Then any block $B \in L_{l_q}$ causes a height increase at $x=l_q$, and any block $B \in R_{l_q}$ corresponds to a height decrease at $x=l_q$; the other blocks do not contribute to the height change at $x=l_q$. $B_q$ is the only block in $D^* \cap L_{l_q}$ (which causes a height increase of $h_q$ at l). Note that $B_p$ is a block in $D^* \cap R_{r_p} = D^* \cap R_{l_q}$ which corresponds to a height decrease of $h_p$ at $l_q$. Since hp>hq, the net effect would be a height decrease at $x=l_q$, contradicting to the fact that C is increasing at $l_q$.

Case (3): hp<hq. The two blocks $B_p=[l_p, r_p] \times h_p$ and $B_q=[l_q, r_q] \times h_q$ can be replaced by $B'_p=[l_p, r_q] \times h_p$ and $B'_q=[l_q, r_q] \times (h_q - h_p)$. The resulting decomposition of C is clearly optimal. Moreover, since $r_q > l_q = r_p$ and $r_p, r_q \in \{0, 1, \ldots, n+1\}$, the new decomposition has actually "moved" the right endpoint of a block in the decomposition D* further to the right by at least one unit distance. In the resulting decomposition of C, it still holds that every $r_i \in \{1, 2, \ldots, n+1\}$ (the $r_i$'s are labeled based on the corresponding left endpoints $l_i$'s of their blocks).

From the above discussions, only Case (3) is actually possible. By repeatedly applying the above transformation operation for Case (3) until the operation is no longer applicable, and based on the fact that Li=i−1 for each i=1, 2, ..., n, it can be concluded that in the resulting optimal decomposition D' of C, $r_i \in \{n, n+1\}$ for each i=1, 2, ..., n.

Considering the height of the IM curve C at x=i−1, then in D'

$$s_1 + s_2 + \ldots + s_i = \sum_{j: i-\frac{1}{2} \in |l_j \cdot r_j|} h_j = \sum_{j=1}^{i} h_j \text{ for } i = 1, 2, \ldots, n.$$

Therefore, $s_i = h_i$ in D' for every i=1, 2, ..., n. Now, considering the height of C at x=n+½, in D'

$$K = \sum_{j: n+\frac{1}{2} \in |l_j \cdot r_j|} h_j = \sum_{j: r_j=n+1} h_j = \sum_{j: r_j=n+1} s_j$$

Thus, a subset $I=\{j\ r_j=n+1 \text{ in D'of} \{1, 2, \ldots, n\}$ is found that satisfies $\Sigma_{i \in I} s_i = K$.

Lemma 2 can be used in developing the following theorem.

Theorem 1. The SLS problem is NP-hard even when the input IM has only one column of cells.

Proof. Lemma 2 shows that the knapsack problem can be transformed to the 2-D IM curve decomposition problem (i.e., the SLS problem with an input IM of only one column of cells). It is obvious that the transformation can be done in polynomial time (the transformation operation for Case (3) above can be repeated only a polynomial number of times since each $r_i$ can be "moved" to the right no more than n times until it reaches n or n+1, and since there are at most n such $r_i$'s). Since the knapsack problem is NP-complete, the theorem follows.

Note that all relevant versions of the 3-D SLS problem, namely, under each MLC model and with or without error control, become the same problem when the given IM consists of only one column of cells. Hence, the above theorem implies that all these versions of the 3-D SLS problem are NP-hard.

Algorithms, in accordance with one embodiment of the present invention, for the 3-D SLS problem with error control on the Elekta™ model, which has the most constraints among the three MLC systems. The extensions of these algorithms to the Siemens™ and Varian™ models will also be described below.

For the basic 3-D SLS problem without error control, the goal is to simply partition a given IM into a minimum set of B-segments of a unit height. The algorithm described in the "Chen et al. I" paper, for the Elekta™ model is based on the following idea and structures.

Figure 22:
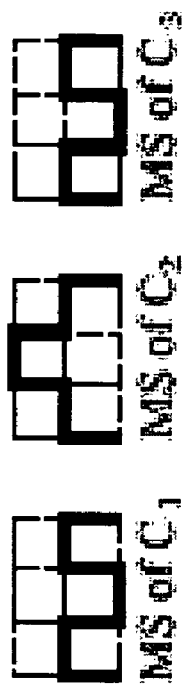
FIG. 22 is a schematic diagram showing the mountain slices (MS) of the three columns of the IM of FIG. 20.
Figure 23:
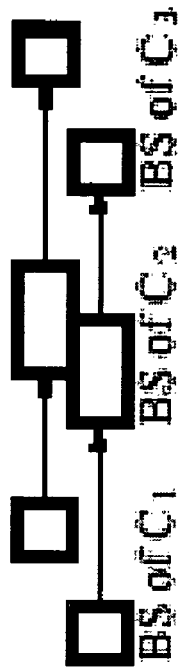
FIG. 23 is a schematic diagram showing the block-sets (BS) of the three mountain slices of FIG. 22 and a stitching of their blocks (indicated by arrows.
Figure 20:
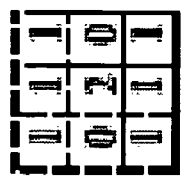
FIG. 20 is a simple IM.
Figure 21:
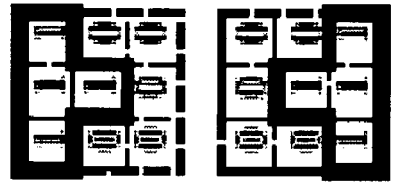
FIG. 21 is a schematic diagram showing the IM of FIG. 20 partitioned into two B-segments of a unit height.

FIG. 20 is a simple IM. FIG. 21 shows the IM of FIG. 20 partitioned into two B-segments of a unit height. FIG. 22 shows the mountain slices (MS) of the three columns of the IM of FIG. 20. FIG. 23 shows the block-sets (BS) of the three mountain slices of FIG. 22 and a stitching of their blocks (indicated by arrows); each path following the arrows corresponds to a B-segment in FIG. 21.

Geometrically, it is possible to view a 3-D IM mountain as consisting of a series of IM "mountain slices", each of which is a 2-D object defined on one column of an IM grid (see FIG. 22 for examples of IM "mountain slices"). Let $S=\{S_i|i\in I\}$ be a set of B-segments that "builds" a 3-D IM mountain, where I is an index set. For the basic 3-D SLS problem, since each B-segment $S_i$ has a unit height and an x-monotone rectilinear simple polygonal shape (for the Elekta™ model), $S_i$ actually builds a continuous block of a unit height on every IM column $C_j$ that intersects the projection of $S_i$ on the IM grid. Such a continuous block is denoted by an interval $B_{i,j}$ on the column $C_j$. (Interchangeably, such an interval $B_{i,j}$ is called a block.) Note that when delivering a B-segment Si, each of its blocks $B_{i,j}$ is delivered by a corresponding pair of MLC leaves that is aligned with $C_j$.

Suppose the blocks created by all B-segments in S on an IM column $C_j$ are "collected." Then this collection of blocks, denoted by $BS(C_j)$, actually "builds" the IM mountain slice defined on $C_j$. This collection of blocks which builds an IM mountain slice is called a block-set. FIG. 23 shows three block-sets whose blocks are represented by the dark rectangles.

The basic 3-D SLS problem without error control can be solved as follows: First select a "good" block-set for building each IM mountain slice, and then somehow "stitch" together the blocks along consecutive IM columns to form B-segments. Here, "stitching" means which of the selected blocks for column $C_{j+1}$ should follow which block for column $C_j$ in a B-segment (see FIG. 23 for an illustration). Note that if no "stitching" occurs, then a given 3-D IM mountain can be "built" by letting each selected block be an individual B-segment. For example, the IM in FIG. 20 may be delivered using six B-segments, each of which is one of the blocks (dark rectangles) in FIG. 23. However, every time two blocks are stitched together (without violating the MLC constraints), the number of B-segments used is reduced by 1. In FIG. 23, 4 stitches may be done and hence reducing the number of B-segments to 2.

It has been shown that it is sufficient to locally stitch together the blocks of the two selected block-sets for any two consecutive IM columns, by computing a maximum cardinality matching between the two corresponding sets of intervals. The number of B-segments thus resulted is guaranteed to be minimum with respect to the selected block-sets (with one block-set for each IM column). Every B-segment consists of a sequence of blocks thus stitched together, with one block from each of the selected block-sets for a list of consecutive IM columns.

To compute a minimum set of B-segments for an IM, a graph G is built as follows:

(1) Generate all distinct block-sets for each IM mountain slice, and let every vertex of G correspond to exactly one such block-set.

(2) For any two vertices of G corresponding to two block-sets for two consecutive IM columns, put a left-to-right directed edge, and assign a weight to that edge based on a maximum cardinality matching between the two corresponding interval sets.

A shortest path in G then specifies a minimum set of B-segments for the given IM with respect to the block-sets used for each IM column.

The algorithm described in the "Chen et al. I" paper, solves the basic 3-D SLS problem without error control. To handle this problem with error control, the error needs to be related to the number of B-segments used.

Let S be a solution for the basic 3-D SLS problem with tongue-or-groove error control, i.e., $S=\{S_i=\{S_i|i\in I\}$ is a set of B-segments of height 1 for the given IM with I being an index set. Consider a B-segment $S_i \in S$. As mentioned above, each B-segment Si actually consists of a sequence of blocks of a unit height on every IM column $C_j$ that intersects the projection of Si on the IM grid. Let $B(S_i)=\{B_{i,j}|B_{i,j}=S_i \cap C_j, j=e_i, e_i+1, \ldots, k_i\}$ be the set of such blocks that form $S_i$, where $S_i$ "runs" consecutively from the IM columns $C_{e_i}$ to $C_{k_i}$.

As discussed above, the tongue-or-groove error of $S_i$ occurs along every vertical boundary edge of the polygonal region of $S_i$. Let $|B_{i,j} \oplus B_{i,j+1}|$ denote the length of the symmetric difference between the two intervals of $B_{i,j}$ and $B_{i,j+1}$, where $j=e_i-1, e_i, \ldots, k_i$ and $B_{i,e_i-1}=\phi$ and $B_{i,k_i+1}=\phi$. Thus, the total tongue-or-groove error $TorG(S_i)$ of $S_i$ is the sum of a set of 3-D error volumes, i.e., $$TorG(S_i) = \sum_{j=e_i-1}^{k_i} w \cdot l_{i,j} \cdot h_i,$$

where w is the (fixed) width of the tongue or groove side of an MLC leaf, $l_{i,j}=|B_{i,j} \oplus B_{i,j+1}|$ is the length of the leaf portion that is actually used for blocking radiation and causes the j-th error volume between blocks $B_{i,j}$ and $B_{i,j}+1$, and $h_i=\alpha \cdot r_i$ is the amount of radiation leakage associated with $S_i$, with $r_i$ being the "height" of $S_i$ and $\alpha$ being the (fixed) leakage ratio. Since for the basic 3-D SLS problem, the B-segments are all of a unit height (i.e., $r_i=1, \forall i \in I$), the tongue-or-groove error of S in this case becomes $$TorG(S_i) = w \cdot \alpha \sum_{i \in I} \sum_{j=e_i-1}^{k_i} l_i, j.$$

Observe that $$\sum_{j=e_i-1}^{k_i} l_{i,j}$$

is the sum of the lengths of all vertical edges of the B-segment $S_i$ (e.g., see FIG. 12).

Thus, there is the following geometric version of the basic 3-D SLS problem with tongue-or-groove error control: Given an IM and an error bound E*, find a set S={S|i∈I} of B-segments of a unit height, such that the value $$C(S) = \sum_{i \in I} \sum_{j=e_i-1}^{k_i} l_{i,j} \leq E^*$$

and the size of |S| is minimized. Note that here, $E^*=E/(w \cdot \alpha)$ for the error bound E in the definition of the SLS problems above.

Since $$C(S) = \sum_{i \in I} \sum_{j=e_i-1}^{k_i} l_{i,j} \leq E^*,$$

by switching the order of the summation and letting n denote the number of columns of the given IM, the result is $$C(S) = \sum_{j=0}^{n} \sum_{i \in I} |B_{i,j} \oplus B_{i,j+1}|.$$

Note that for each j=0, 1, ..., n, the value $$C(S) = \sum_{j=0}^{n} \sum_{i \in I} |B_{i,j} \oplus B_{i,j+1}|$$

is actually the tongue-or-groove error for "stitching" the two block-sets $BS(C_j)$ and $BS(C_{j+1})$ for the IM columns $C_j$ and $C_{j+1}$ defined by S. Suppose g pairs of blocks are stitched together by S between $BS(C_j)$ and $BS(C_{j+1})$. To minimize the error of S, the error incurred for such a stitching configuration (i.e., $\Sigma_{i \in I}|B_{i,j} \oplus B_{i,j+1}|$) must be the smallest among all possible stitching configurations with exactly g stitched block pairs between $BS(C_j)$ and $BS(C_{j+1})$ defined by S.

Now the tongue-or-groove error can be related to the number of B-segments, by associating an error to each stitching configuration between the block-sets for any two consecutive IM columns. Specifically, for any two block-sets $BS(C_j)$ and $BS(C_{j+1})$ for columns $C_j$ and $C_{j+1}$ and each g=1, 2, ..., $|M_j|$, where $M_j$ is a maximum cardinality matching between $BS(C_j)$ and $BS(C_{j+1})$, exactly g pairs of blocks are stitched together with the minimum total error. Note that every stitching configuration of exactly g block pairs between $BS(C_j)$ and $BS(C_{j+1})$ with the minimum error corresponds to a matching of exactly g pairs of intervals with the minimum total weight between the two interval sets of $BS(C_j)$ and $BS(C_{j+1})$. Such a bipartite matching of intervals (subject to the MLC constraints) are called an optimal g-matching. Hence, an optimal solution for the basic 3-D SLS problem with error control is specified by a list of block-sets (one for each IM column) and an optimal g-matching between two such block-sets $BS(C_j)$ and $BS(C_{j+1})$ for any consecutive columns $C_j$ and $C_{j+1}$ (for some value $g_j$).

To find the sought block-sets and $g_j$-matchings, the following directed acyclic graph G* is constructed:

(1) Generate all distinct block-sets for each IM column, and let every vertex of G* correspond to exactly one such block-set.

(2) For any two vertices of G* corresponding to two block-sets $BS(C_j)$ and $BS(C_{j+1})$ for two consecutive IM columns $C_j$ and $C_{j+1}$, compute a minimum weight g-matching for each g=1, 2, ..., $|M_j|$, where $M_j$ is a maximum cardinality matching between $BS(C_j)$ and $BS(C_{j+1})$. For each such g-matching, put a left-to-right edge between the two vertices in G*, and assign the edge a weight of $|BS(C_{j+1})|-g$ and a cost equal to the minimum weight of the g-matching. (Note that this assignment scheme of edge weights, i.e., $|BS(C_{j+1})|-g$, is the same as in the "Chen et al. I" paper.

(3) Add a source vertex s to G* and connect s to all block-sets for the first IM column; add a sink t and connect all block-sets for the last IM column to t (all edges added here have weight zero and cost zero).

The following lemma is a key to one algorithm of the present invention. In fact, it is a generalization of similar but more primitive observations in the "Chen et al. I" paper, (for the problem versions without error control), and its correctness proof is also similar to the proofs of those observations in the "Chen et al. I" paper.

Lemma 3. An s-to-t path in the graph G* with a weight k and a cost C specifies a set of k B-segments of a unit height for the given IM whose total tongue-or-groove error is C.

Lemma 3 implies that for the basic 3-D SLS problem with a given error bound E*, it is possible to obtain a minimum B-segment set for the given IM subject to this error bound, by finding a minimum weight s-to-t path in G* with a total cost≤E*. This is called the constrained shortest path problem.

To compute such a set of B-segments, several issues must be resolved: (1) How to generate all distinct block-sets for each IM mountain slice? (2) How to compute an optimal g-matching between two block-sets? (3) How to find a minimum weight s-to-t path in G* with a total cost≤E*?

To generate all distinct block-sets for an IM column, an algorithm in the paper Luan et al., "An Optimal Algorithm for Computing Configuration Options of One-dimensional Intensity Modulated Beams" in *Phys. Med. Biol*, 48(15): 2321-2338, 2003 is used whose running time is linear in terms of the size of the output block-sets. To find a desired k-weight shortest s-to-t path in G*, Lawler's dynamic programming algorithm is used for constrained shortest paths. The sought path can be easily obtained from the dynamic programming table once it becomes available.

Now it will be shown how to compute the optimal g-matchings. Given two block-sets $BS_r$ and $BS_b$ for any two consecutive IM columns, a bipartite graph $|G=(R \cup B,E)|$ is constructed as follows: Each block in $BS_r$ (resp., $BS_b$) corresponds to a red (resp., blue) vertex in G, and every stitchable block pair corresponds to an edge between the corresponding red and blue vertices. Here, a red block and a blue block are stitchable if they satisfy the (machine model specific) MLC constraints. For each edge e(u, v) in G, let their corresponding intervals be $I_u=[l_u, r_u]$ and $I_v=[l_v, r_v]$; then the cost of e(u, v) is assigned as $|l_u-l_v|+|r_u-r_v|$, i.e., the length of the symmetric difference between $I_u$ and $I_v$.

To compute an optimal g-matching in the bipartite graph G for each g=1, 2, . . . , |M|, where M is the maximum cardinality matching of G, G is transformed into a unit-capacity flow network and formulate the task as a minimum cost flow problem with a flow value g. The |M| optimal g-matchings can be computed efficiently by the successive shortest path algorithm, i.e., at the end of the g-th stage of the algorithm ($1 \leq g \leq |M|$), a desired optimal g-matching is produced. Since the single source shortest paths in G at each stage can be computed in O(m+n log n) time, the total time for computing all the |M| optimal g-matchings ($1 \leq g \leq |M|$) is O(|M|(m+n log n)), where m=|E| and n=|R∪B|.

Theorem 2. The basic 3-D SLS problem with tongue-or-groove error control is solvable in $$O\left(\sum_{j=0}^{n} \prod_{j} \cdot \prod_{j+1} \cdot \Gamma + K\right)$$

time, where n is the number of columns of the input IM, Πj is the number of block-sets used for column Cj, Γ is the time for computing all optimal g-matchings between two block-sets, and K is the time for computing the minimum cost k-weight s-to-t paths in G*.

Recall that the 2-D SLS problem on the Elekta™ model (defined above) is to partition a given polygonal domain P (possibly with holes) embedded on a uniform planar grid into a minimum set of x-monotone rectilinear simple polygons (i.e., B-segments) whose total tongue-or-groove error is subject to a given error bound E. Like the basic 3-D case, all B-segments for the 2-D SLS problem also have the same height; hence it suffices to use the sum of the lengths of all vertical edges of the B-segments to capture the associated tongue-or-groove error. Thus, the 2-D SLS problem essentially is to partition the given polygonal domain P into a minimum set of x-monotone rectilinear simple polygons subject to an error bound E* on the total sum of the lengths of the newly inserted vertical edges in all the resulting monotone polygons. (Specifically, E*=E/(w·h)h), where w is the (fixed) width of the tongue or groove side of an MLC leaf, h=α·r is the amount of radiation leakage associated with each segment, with r being the "height" of the segment and α being the leakage ratio.) For example, if the given length sum of the newly inserted vertical edges is zero, then only horizontal edges can be used in the partition.

Figure 24:
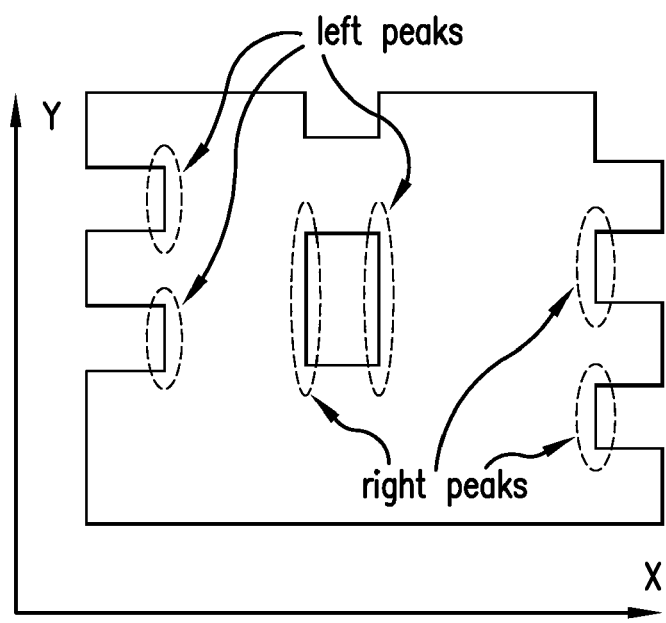
FIG. 24 is a diagram showing the left and right peaks of a polygon
Figure 25:
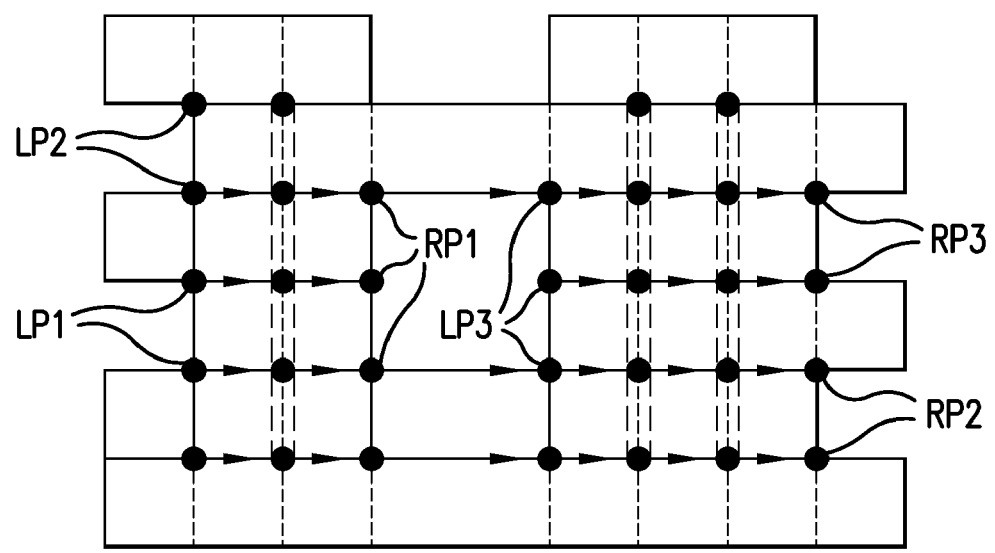
FIG. 25 is a directed grid graph modeling the 2-D SLS problem with error control for the polygon of FIG. 24.

FIG. 24 shows the left and right peaks of a polygon. FIG. 25 shows the directed grid graph modeling the 2-D SLS problem with error control for the polygon of FIG. 24; the thick edges indicate a minimum cost flow.

Chen et al., as described in the "Chen et al. I" paper, developed an algorithm for partitioning a polygonal domain into the minimum number of x-monotone simple polygons on a uniform grid. Their algorithm is based on the idea of peak eliminations. Specifically, a vertical boundary edge e of a rectilinear polygon P is a left peak if the two horizontal edges of P adjacent to e are both to the left of e (e.g., see FIG. 24). Similarly, a right peak is a vertical edge of P whose two adjacent horizontal edges are both to its right. Each time a left peak is connected to a right peak, the number of x-monotone simple polygons is reduced by 1. Hence to obtain a minimum partition, one needs to connect as many left peaks to right peaks as possible, which becomes a problem of computing a maximum bipartite matching between the two sets of left and right peaks of P. In the "Chen et al. I" paper the sought bipartite matching is computed by finding a maximum flow on the grid graph induced by the IM grid (see FIG. 25), where the flow value directly controls the number of x-monotone polygons in the resulting partition.

To solve 2-D SLS problem with error control, according to one embodiment of the present invention, the same grid graph model as in the "Chen et al. I" paper is used, except that a minimum cost flow is now computed in this graph (instead of a maximum flow as in paper 13). The cost of the flow indicates the amount of tongue-or-groove error, and the amount of flow indicates the number of the resulting x-monotone polygons (i.e., B-segments). One key to this construction is to associate with each vertical edge in the grid graph a cost that is equal to its geometric length. (In this construction, all horizontal edges have a zero cost.)

Lemma 4. Each flow with a flow value F and a cost C in the grid graph thus constructed corresponds to a desired partition of the polygonal domain P (possibly with holes) such that the size of the resulting partition is a function of F and the tongue-or-groove error of the partition is a function of C.

Proof. In the "Chen et al. I" paper it was shown that each flow of a value F in the grid graph corresponds to an x-monotone partition of the polygonal domain P with a size $C_1$-F for some fixed value $C_1$ ($C_1$ is related to the number of the left/right peaks of P). Actually, the flow partitions the polygonal domain into a set of sub-polygons, and each such sub-polygon can be partitioned into x-monotone polygons by using only horizontal edges. Hence, the only vertical edges that are used in the partition are either (1) the vertical edges on the boundary of the input polygonal domain, whose length sum is a fixed value (say $C_2$), or (2) the vertical edges that are selected by the flow, whose length sum is 2C. This gives a total error of $2C+C_2$ for the x-monotone partition.

Now it is possible to relate the error (the flow cost) to the number of the resulting x-monotone polygons (the flow value). Note that in Lemma 4, when the value of F increases, the value of C decreases, and vice versa. Of course, for each flow value, it is possible to find a flow with the minimum cost (to minimize its error). Thus, there is a minimum cost flow problem. It is clear that by varying the flow values and computing their corresponding minimum cost flows in the grid graph, one obtains the sought tradeoff between the number of B-segments and the tongue-or-groove error for the 2-D SLS problem.

Theorem 3. The 2-D SLS problem with tongue-or-groove error control on any IM grid of size $\sqrt{\Lambda} \times \sqrt{\Lambda}$ can be solved in $O(\Lambda^2 \log \Lambda$ time).

Note that, the O(log Λ) factor in the running time is due to the fact that in the minimum cost flow algorithm, a shortest path algorithm is used instead of a depth-first search algorithm.

A heuristic algorithm for the general 3-D SLS problem with error control will now be described. This algorithm is based on the 3-D SLS and 2-D SLS algorithms described above, and its spirit is somewhat similar to the heuristic 3-D SLS algorithm without error control in "Chen et al. I" paper. The input 3-D IM "Mountain" is partitioned into a set of sub-IMs, such that each such sub-IM can be handled optimally by one of these two algorithms (i.e., to use the 2-D SLS algorithm, such a sub-IM must have a uniform height; to use the 3-D SLS algorithm, of one embodiment of the present invention, the maximum height of such a sub-IM should be reasonably small, say, ≦5). The difference here is when combining the solutions obtained from the sub-IMs, dynamic programming is used to determine the tradeoff between the number of B-segments and the tongue-or-groove error for the entire 3-D IM mountain.

The main steps of the 3-D SLS algorithm, of one embodiment of the present invention, with tongue-or-groove error control are:
(1) Partition the given 3-D IM into sub-IMs using the dynamic level-choosing method in the "Chen et al. I" paper.
(2) Compute a tradeoff table between the error and the number of B-segments for each sub-IM by using either the basic 3-D SLS algorithm or the 2-D SLS algorithm described above.
(3) Use dynamic programming to compute a tradeoff table for the entire 3-D IM mountain.

As discussed above, the tongue-and-groove error of an IMRT plan is the intersection $|V_T \cap V_G|$, while the tongue-or-groove error is the sum $|V_T|+|V_G|$, where $V_T$ (resp., $V_G$) is the error set (i.e., a set of 3-D axis-parallel boxes) caused by the tongue sides (resp., groove sides) of the MLC leaves. At first sight, due to the nonlinearity, it might appear that the tongue-and-groove error is much harder to handle than the tongue-or-groove error. Interestingly, it is possible to show that handling the tongue-and-groove error is in fact equivalent to handling the tongue-or-groove error. A key to the solution in one embodiment of the present invention is set forth in Lemma 5 below which implies that the SLS algorithms for tongue-or-groove error control of the present invention are also applicable to the case of tongue-and-groove error control.

Lemma 5. Let M be the input IM and S be a B-segment set that builds M. Then the difference between the values of the tongue-or-groove error and tongue-and-groove error of S is merely a value F(M) that depends only on the input IM M.

Observe that, Lemma 5 immediately implies that minimizing the tongue-and-groove error is equivalent to minimizing the tongue-or-groove error. Therefore, the 3-D SLS algorithms for tongue-or-groove error control are also applicable to the case of tongue-and-groove error control. Below is a proof of Lemma 5 which introduces the concepts of tongue error function $f_T$ and groove error function $f_G$. The reason for introducing such mathematical formulations of errors is that it appears quite difficult to deal with the tongue-and-groove error directly based on its definition, due to its non-linear nature. However, with the help of these mathematical formulations, the tongue-or-groove error and the tongue-and-groove error are simply the integrals of some mathematical combinations of these functions. Specifically, the tongue-or-groove error is equal to $$\int_{-\infty}^{+\infty}(f_T+f_G),$$

and the tongue-and-groove error is equal to $$\int_{-\infty}^{+\infty}\min\{f_T, f_G\}.$$

It will also be shown below that the difference between the tongue-and-groove error and tongue-or-groove error depends only on the given IM M by using a series of manipulations of their corresponding integrals.

Figure 26:
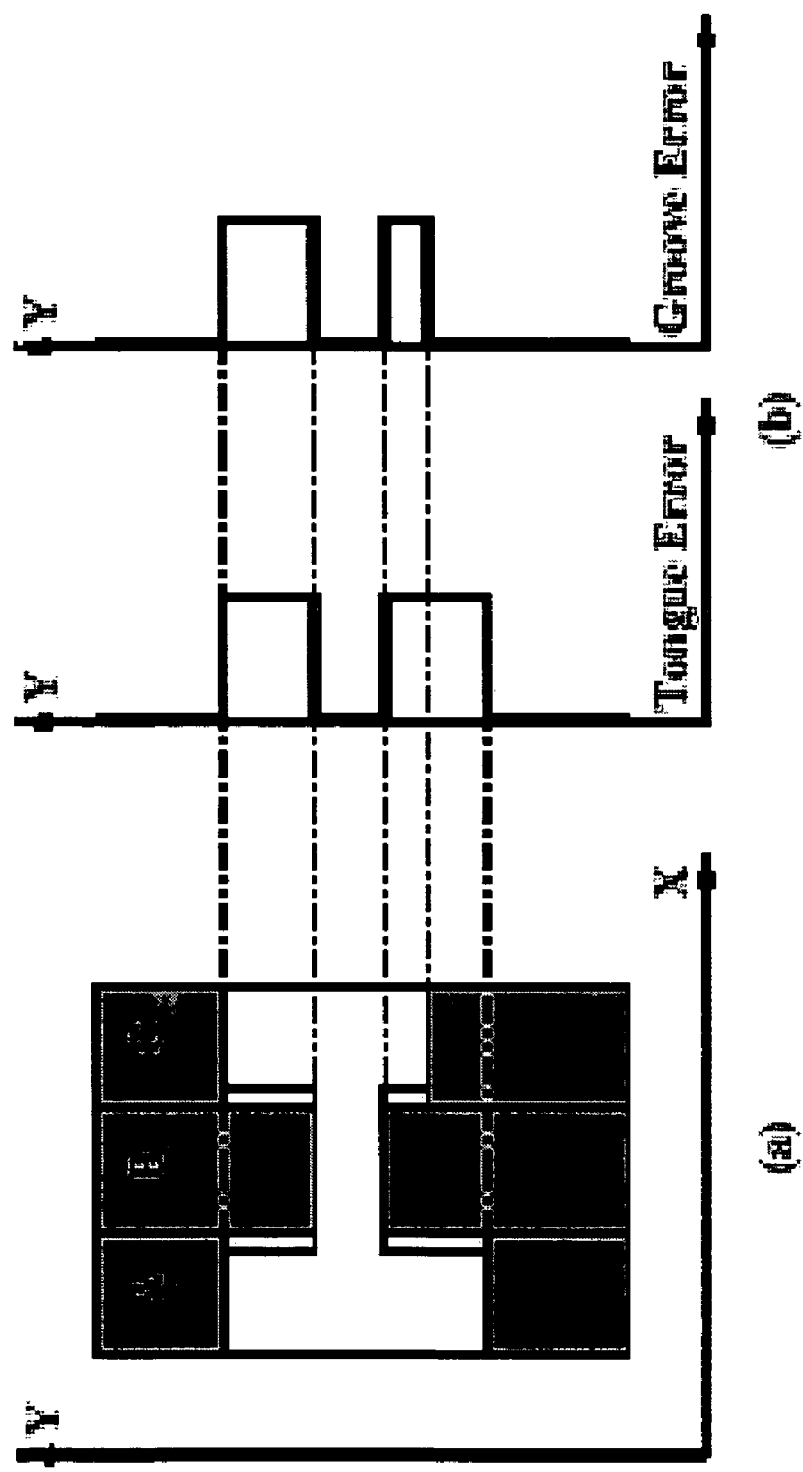
FIG. 26 is an illustration of the tongue error and groove error as functions defined on the y-axis for (a) A B-segment and (b) the tongue error and groove error of the MLC leaf pair B caused by the delivery of the B-segment in (a).

FIG. 26 is an illustration of the tongue error and groove error as functions defined on the y-axis for (a) A B-segment and (b) the tongue error and groove error of the MLC leaf pair B caused by the delivery of the B-segment in (a).

The error caused by using the tongue side of an MLC leaf for blocking radiation for the purposes of the present invention is called the tongue error, and the error caused by using the groove side for blocking radiation for the purposes of the present invention is called the groove error. Observe that, if one ignores the width w of the tongue or groove side of an MLC leaf, then the tongue error and groove error caused by the j-th MLC leaf pair with respect to a B-segment $S_i$ of height $r_i$ (i.e., the number of radiation units delivered by Si) can actually be viewed as functions that are defined on the y-axis and also depend on $r_i$ (see FIG. 26). These functions are denoted by $f_T(j, S_i)$ and $f_G(j, S_i)$, and, for the purpose of the present invention, are called the tongue error and groove error functions, respectively.

To determine the amount of tongue error, $TE(j, S_i)$, or the amount of groove error, $GE(j, S_i)$, of a B-segment $S_i$ caused by the j-th MLC leaf pair, it is possible to integrate its tongue error or groove error function. That is, $$TE(j, S_i) \int_{-\infty}^{+\infty} f_T(j, S_i) \text{ and}$$

$$GE(j, S_i) \int_{-\infty}^{+\infty} f_G(j, S_i)$$

(To be exact, these errors should be $w \cdot GE(j, S_i)$; the fixed value w is simply dropped.) Suppose that the B-segment $S_i$ involves the leaf pairs $e_i, e_i+1, \ldots, k_i$. Then the total tongue error $TE(S_i)$ and the total groove error $GE(S_i)$ for $S_i$ are $$TE(S_i) = \sum_{j=e_i}^{k_i} TE(j, S_i) \text{ and } GE(S_i) = \sum_{j=e_i}^{k_i} GE(j, S_i).$$

Let $S=\{S_i|i\in I\}$ be a set of B-segments for an IM, where I is an index set. Then the tongue error TE(s) and groove error GE(s) of S can be computed as the sums of all tongue errors and groove errors of its individual B-segments. Thus, $$TE(S_i) = \sum_{i\in I}^{k_i} TE(S_i) \text{ and } GE(S_i) = \sum_{i\in I}^{k_i} GE(S_i).$$

Note that $$TE(S) = \sum_{i\in I} TE(S_i)$$

$$= \sum_{i\in I}\sum_{j=e_i}^{k_i} TE(j, S_i)$$

-continued $$= \sum_{i \in I} \sum_{j=e_i}^{k_i} \int_{-\infty}^{+\infty} f_T(j, S_i) TE(Si)$$

By changing the order of the summations and assuming that there are n MLC leaf pairs, the result is $$TE(S) = \sum_{j=1}^{n} \int_{-\infty}^{+\infty} \left( \sum_{i \in I} f_T(j, S_i) \right)$$

For the purposes of the present invention, the term $\Sigma_{i \in I} f_T(j,S_i)$ is referred to as the tongue error function of the j-th leaf pair with respect to the B-segment set S, and denote it by $f_T(j, S)$. Similarly, for the purposes of present invention, the term $\Sigma_{i \in I} f_G(j,S_i)$ is referred to as the tongue error function of the j-th leaf pair with respect to the B-segment set S, and denote it by $f_G(j, S)$. Note that the integral $$\int_{-\infty}^{+\infty} f_T(j, S)$$

is the amount of error caused by using the tongue side of the j-th MLC leaf pair in the B-segment set S, and the integral $$\int_{-\infty}^{+\infty} f_G(j, S)$$

is the amount of error caused by using the groove side of the j-th MLC leaf pair.

As described above, the tongue-or-groove error, TorG(s), of a B-segment set S is the sum of its tongue error TE(s) and groove error GE(s). Thus, $$TorG(S) = TE(S) + GE(S)$$

$$= \sum_{j=1}^{n} \int_{-\infty}^{+\infty} f_T(j, S) + \sum_{j=1}^{n} \int_{-\infty}^{+\infty} f_G(j, S)$$

By changing the order of the summations and integrations, the result is $$TorG(S) = \int_{-\infty}^{+\infty} \sum_{j=1}^{n} (f_T(j, S) + f_G(j, S))$$

The function $$TorG(S) = \sum_{j=1}^{n} (f_T(j, S) + f_G(j, S))$$

is called the tongue-or-groove function of the B-segment set S.

Figure 27:
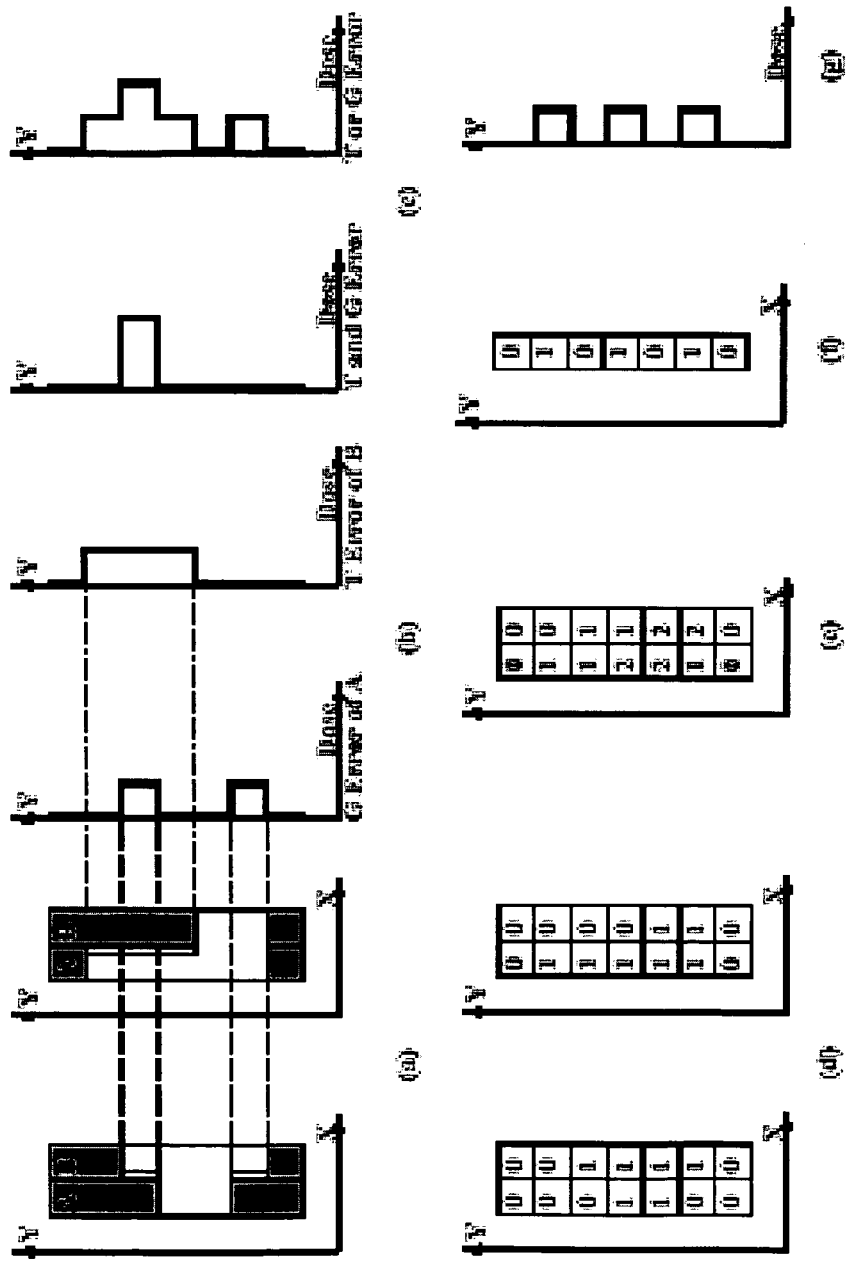
FIG. 27 is a series of graphs the relation between the tongue-and-groove and tongue-or-groove errors, where (a) shows a set S of two B-segments, (b) shows groove error $f_G(A, S)$ of the leaf pair A and the tongue error $f_T(B, S)$ of the leaf pair B, (c) shows the tongue-and-groove error function $f_{TandG}(s)$ and tongue-or-groove error function $f_{TorG}(s)$ of the two B-segments in (a) (the tongue-and-groove error is twice the size of the intersection of the tongue error and groove error, as shown above, (d) shows the matrices of the two B-segments in (a) (assuming that the B-segments are both of a height 1), (e) shows the dose distribution created by the B-segments in (a), (f) shows the absolute difference between the two columns of the dose distribution in (e), and (g) shows $f_{TorG}(s)-f_{TandG}(s)$, which is the function corresponding to the absolute difference in (f)

FIG. 27 illustrates the relation between the tongue-and-groove and tongue-or-groove errors, where (a) shows a set S of two B-segments, (b) shows groove error $f_G(A, S)$ of the leaf pair A and the tongue error $f_T(B, S)$ of the leaf pair B, (c) shows the tongue-and-groove error function $f_{TandG}(s)$ and tongue-or-groove error function $f_{TorG}(s)$ of the two B-segments in (a) (the tongue-and-groove error is twice the size of the intersection of the tongue error and groove error, as shown above, (d) shows the matrices of the two B-segments in (a) (assuming that the B-segments are both of a height 1), (e) shows the dose distribution created by the B-segments in (a), (f) shows the absolute difference between the two columns of the dose distribution in (e), and (g) shows $f_{TorG}(s) - f_{TandG}(s)$, which is the function corresponding to the absolute difference in (f).

As shown above, the tongue-and-groove error occurs when the tongue side of an MLC leaf and the corresponding groove side of its neighboring leaf are both used for blocking radiation. Thus, the tongue-and-groove error is related to the groove error of a leaf pair and the tongue error of a neighboring leaf pair. Consider the j-th and (j+1)-th MLC leaf pairs. Let $f_G(j, S)$ be the groove error function of the j-th leaf pair, and $f_T(j+1, S)$ be the tongue error function of the (j+1)-th leaf pair. Then it is clear that the tongue-and-groove error on these two leaf pairs occurs if and only if the function min $\{g(j, S), fT(j+1, S)\}$ is not always zero. (See FIG. 27 for an illustration of the function min $\{(j, S), fT(j+1, S)\}$.)

Geometrically, if the two functions $f_G(j, S)$ and $f_T(j+1, S)$ are viewed as the polygonal regions enclosed by the y-axis and their functional curves (see FIG. 27(b)), then the tongue-and-groove error is actually twice the area of the intersection between these two types of regions (see FIG. 11 (c)). A non-empty intersection of such regions (i.e., min $\{g(j, S), f_T(j+1, S)\}$ is not always zero) occurs in an area where the groove side of the j-th leaf pair and the tongue side of the (j+1)-th leaf pair both block radiation in different B-segments of the B-segment set S.

Hence, if $f_{TandG}(j,j+1, S)$ is used to denote the tongue-and-groove error function between the j-th and (j+1)-th leaf pairs with respect to the B-segment set S, then $$f_{TandG}(j,j+1,S) = 2 \cdot \min\{(j,S), f_T(j+1,S)\}.$$

The tongue-and-groove error for the B-segment set S, TandG(s), is the following sum of integrals:

$$\sum_{j=1}^{n-1} \int_{-\infty}^{+\infty} f_{TandG}(j, j+1, S),$$

where n is the number of MLC leaf pairs used (or the number of columns of the input IM). Rearranging the order of the summation and integration, results in:

$$TandG(S) = \int_{-\infty}^{+\infty} \sum_{j=1}^{n-1} f_{TandG}(j, j+1, S).$$

For the purposes of the present invention, the function $$\sum_{j=1}^{n-1} f_{TandG}(j, j+1, S)$$

is called the tongue-and-groove error function of the B-segment set S.

Let M be an input IM of m rows and n columns of cells. Consider two cells c(k,j) and c(k,j+1) of M. (Note that the cell c(k,j) is aligned to the j-th MLC leaf pair and c(k,j+1) is aligned to the (j+1)-th leaf pair.) Let $f_G(j, S)$ be the groove error of the j-th leaf pair with respect to a B-segment set S, and $f_T(j+1, S)$ be the tongue error of the (j+1)-th leaf pair. Observe that the geometric meaning of the value $f_G(j, S)(k)$ is that $f_G(j, S)(k)/a$ more units of radiation are delivered to c(k, j+1) than c(k, j), where a is the fixed leakage ratio of the tongue and groove side of an MLC leaf. This is because whenever the groove side of the j-th leaf pair is used for blocking radiation, the cell c(k,j) is hidden under the j-th leaf pair while the cell c(k, j+1) is exposed. Similarly, the geometric meaning of the value $f_T(j+1, S)(k)$ is that $f_T(j+1, S)(k)=\_$ more units of radiation are delivered to c(k,j) than c(k,j+1). Hence, the absolute difference between the two values, $|f_G(j,S)(k)-f_T(j+1,S)(k)|$, is equal to $\alpha \cdot |h(k,j)-h(k,+1)|$ where h(k,j) and h(k, j+1) are the heights of the two cells c(k,j) and c(k, j+1) in M, respectively. (See FIG. 27 for an illustration). Hence:

$$|f_G(j,S)(k) - f_G(j+1,S)(k)| = \alpha \cdot |h(k,j) - h(k,+1)|$$

Observe that $$(f_G(j,S)(k) + f_T(j+1,S)(k)) - 2 \cdot \min\{f_G(j,S)(k), f_T(j+1,S)(k)\} = |f_G(j,S)(k) - f_T(j+1,S)(k)|.$$

Let $f_{TorG}(j, j+1, S) = f_G(j,S) + f_T(j+1,S)$. Then:

$$f_{TorG}(j, j+1, S)(k) - f_{TandG}(j, j+1, S)(k) = \alpha \cdot |h(k,j) - h(k,j+1)|.$$

Recall that the tongue-or-groove error function $f_{TorG}(s)$ is of the following form $$f_{TorG}(S) = \sum_{j=2}^{n}(f_T(j, S) + f_G(j, S))$$

$$= f_T(1, S) + \sum_{j=1}^{n-1}(f_G(j, S) + f_T(j+1, S)) + f_G(n, S)$$

Hence, the tongue-or-groove error TorG(s) is:

$$TorG(S) = \int_{-\infty}^{+\infty} f_{TorG}(S) = \int_{-\infty}^{+\infty} f_T(1, S) +$$

$$\sum_{j=1}^{n-1} \int_{-\infty}^{+\infty}(f_G(j, S) + f_T(j+1, S)) + \int_{-\infty}^{+\infty} f_G(n, S)$$

$$= \sum_{k=1}^{m} f_T(1, S)(k) + \sum_{j=1}^{n-1}\sum_{k=1}^{m}(f_G(j, S)(k) +$$

$$f_T(j+1, S)(k)) + \sum_{k=1}^{m} f_G(n, S)(k)$$

Thus:

$$TorG(S) = \sum_{k=1}^{m} f_T(1, S)(k) + \sum_{j=1}^{n-1}\sum_{k=1}^{m}(f_G(j, S)(k) + \qquad (2)$$

$$f_T(j+1, S)(k)) + \sum_{k=1}^{M} f_G(n, S)(k).$$

Recall that the tongue-and-groove error is of the following form $$f_{TandG}(S) = \int_{-\infty}^{+\infty} \sum_{j=1}^{n-1} 2 \cdot \min\{f_G(j, S), f_T(j+1, S)\}.$$

Hence the tongue-and-groove error TandG(s) of S is $$TandG(S) = \int_{-\infty}^{+\infty} f_{TandG}(S) = \sum_{j=1}^{n-1} \int_{-\infty}^{+\infty} 2 \cdot \min\{f_G(j, S), f_T(J+1, S)\} =$$

$$\sum_{j=1}^{n-1}\sum_{k=1}^{m} 2 \cdot \min\{f_G(j, S)(k), f_T(j+1, S)(k)\}.$$

which can be reduced to following equation:

$$TandG(S) = \sum_{j=1}^{n-1}\sum_{k=1}^{m} 2 \cdot \min\{f_G(j, S)(k), f_T(j+1, S)(k)\} \qquad (3)$$

From Equations (2) and (3), it follows:

$$TorG(s) - TandG(S) = \sum_{k=1}^{m} f_T(1, S)(k) + \sum_{k=1}^{m} f_G(n, S)(k) +$$

$$\sum_{j=1}^{n-1}\sum_{k=1}^{m}\{f_G(j, S)(k) + f_T(j+1, S)(k)\} -$$

$$2 \cdot \min\{f_G(j, S)(k), f_T(j+1, S)(k)\})$$

$$= \sum_{k=1}^{m} f_T(1, S)(k) + \sum_{k=1}^{m} f_G(n, S)(k) +$$

$$\sum_{j=1}^{n-1}\sum_{k=1}^{m}\{f_{TorG}(j, j+1, S)(k) -$$

$$f_{TandG}(j, j+1, S)(k).$$

Substituting $$\sum_{k=1}^{m} f_T(1, S)(k) = \alpha \cdot \sum_{k=1}^{m} h(k, 1), \sum_{k=1}^{m} f_G(n, S)(k)$$

$$= \alpha \cdot \sum_{k=1}^{m} h(k, n),$$

and applying Equation (1) results in equation 4

$$TorG(s) - TandG(S) = \alpha \cdot \left( \sum_{k=1}^{m} h(k+1) + \sum_{j=1}^{n-1} \sum_{k=1}^{m} |h(k, j) - h(k, j+1)| + \left| \sum_{k=1}^{m} h(k, n) \right| \right) \quad (4)$$

Finally, observe that the value of $$\sum_{k=1}^{m} h(k, 1) + \sum_{j=1}^{n-1} \sum_{k=1}^{m} |h(k, j) - h(k, j+1)| + \sum_{k=1}^{m} h(k, n)$$

depends only on the input IM M. Thus Lemma 5 follows.

In embodiments of the present invention, 3-D SLS algorithms for the Elekta™ MLC may be extended to the Siemens™ and Varian™ MLC models. A description will be provided below that extends the 2-D and 3-D SLS algorithms for the Elekta™ MLC to the Siemens™ and Varian™ MLC models. A post-processing procedure to enable the extended algorithms to take full advantage of the more flexible constraints of the Siemens™ and Varian™ MLCs will also be described below.

Recall that in one embodiment basic 3-D SLS algorithm for the Elekta™ MLC described above that the MLC constraints are implemented when computing the "stitching" configurations (i.e., the optimal g-matchings) between any two block-sets for consecutive IM columns. Specifically, on the Elekta™ model, two blocks may be stitched together if and only if their corresponding intervals have an intersection of a length no shorter than the minimum separation value δ, due to the no-interleaf motion and minimum leaf separation constraints.

To extend one basic 3-D SLS algorithm of the present invention to the Siemens™ and Varian™ MLC models, the way in which two intervals are stitched together in the computation of the optimal g-matchings may be determined, to reflect the constraints of the Siemens™ or Varian™ MLC. Specifically, on the Siemens™ model which has the no-interleaf motion constraint, two blocks are stitched together if and only if their corresponding intervals have a non-empty common intersection. On the Varian™ model, since the interleaf motion is allowed, any two blocks can be stitched together.

In one 2-D SLS algorithm of the present invention for the Elekta™ MLC, the MLC constraints are modeled by properly setting the flow capacities of the edges and vertices in the grid graph used. Hence, to extend this algorithm to the Siemens™ and Varian™ MLCs, the capacity assignments of the grid graph are modified. Specifically, for the Siemens™ MLC, a flow capacity is assigned of 1 to all vertical edges (to enforce the no-interleaf motion constraint), and an unlimited capacity to all horizontal edges. For the Varian™ MLC, an unlimited capacity is assigned to all vertices and edges. It is clear that these capacity assignments model the 2-D SLS problem well for the Siemens™ and Varian™ MLCs. (Note that on the Siemens™ and Varian™ models, the sought x-monotone polygons are stored implicitly in the flow graph. To output the actual B-segments, the resulting flows may be used to guide the extraction of these x-monotone polygons as in the "Chen et al. I" paper.

Using the heuristic scheme described above and the above extensions of the basic 3-D SLS and 2-D SLS algorithms, it is possible to obtain a similar general 3-D SLS algorithm for the Siemens™ and Varian™ MLCs. But, this version of the 3-D SLS algorithm actually generates a set of B-segments whose blocks are from consecutive IM columns. As described above, know that both the Siemens™ and Varian™ models allow B-segments of a degenerate polygonal shape (i.e., the blocks of a B-segment need not be from consecutive IM columns). Hence, to take full advantage of this feature of the Siemens™ and Varian™ MLCs, multiple disjoint B-segments are "linked" into one B-segment (whenever possible) to reduce the number of B-segments used, as long as the x-monotonicity of the resulting B-segments is not violated.

Let H be a graph in which each vertex corresponds to exactly one of the B-segments computed by the above heuristic 3-D SLS algorithm. For any two vertices in H, a left-to-right directed edge is put if their corresponding B-segments can be delivered together as a single MLC-aperture (on a Siemens™ or Varian™ MLC); the cost of this edge is the machine delivery error incurred when the two B-segments are combined into one. Then, it is easy to see that a g-path cover with a cost C in the graph H corresponds to a set of g B-segments with a machine delivery error C for the Siemens™ or Varian™ model.

Since H is a directed acyclic graph, it is possible to apply the path covering technique in Boesch et al., "Covering the Points of a Digraph with Point-Disjoint" Paths and Its Application to Code Optimization. Journal of ACM, 24(3):192{198, 1977, the entire contents and disclosure of which is hereby incorporated by reference and transform the minimum cost g-path cover problem on H into a minimum cost g'-cardinality matching problem on a bipartite graph, which can be solved by the optimal g-matching algorithm described above.

The treatment time and machine delivery error are two crucial factors of a solution (i.e., a treatment plan) for the SLS problem. The 3-D SLS problem is NP-hard In one embodiment, the 3-D SLS error correction method of the present invention employs an algorithm for solving the 3-D SLS problem based on a tradeoff between the treatment time and machine delivery error (also called the "tongue-and-groove" error in medical literature). In one embodiment, the 3-D SLS error correction method of the present invention gives the users (e.g., physicians) the flexibility of specifying a machine delivery error bound, and subject to the specified error bound, the algorithm computes a treatment plan with the minimum treatment time. In one embodiment, the 3-D SLS error correction method of the present invention employs an algorithm that is based on the k-weight shortest path, minimum g-matching, and minimum cost flow algorithms. In other embodiments, the 3-D SLS error correction method of the present invention uses a 3-D SLS algorithm in popular radiotherapy machine models with various constraints, such as the Siemens™ and Varian™ systems. In one embodiment, the 3-D SLS error correction method of the present invention is based on computing a minimum g-path cover on a directed acyclic graph.

In one embodiment, the present invention a new geometric algorithm for the 3-D static leaf sequencing (SLS) problem arising in intensity-modulated radiation therapy (IMRT), a modern cancer treatment technique. The treatment time and machine delivery error are two crucial factors for measuring the quality of a solution (i.e., a treatment plan) for the SLS problem. In the current clinical practice, physicians prefer to use treatment plans with the lowest possible amount of delivery error, and are also very concerned about the treatment time. Previous SLS methods in both the literature and commercial treatment planning systems either cannot minimize the error or achieve that only by treatment plans which require a prolonged treatment time. In comparison, in one embodiment geometric algorithm is computationally efficient; more importantly, it guarantees that the output treatment plans have the lowest possible amount of delivery error, and the treatment time for the plans is significantly shorter. One solution of the present invention is based on a number of schemes and ideas (e.g., mountain reduction, block matching, profile-preserving cutting, etc) which may be of interest in their own right. Experimental results based on real medical data showed that one algorithm in accordance to one embodiment of the present invention runs fast and produces much better quality treatment plans than current commercial planning systems and well-known algorithms in medical literature.

One popular IMRT delivery technique is called the static leaf sequencing (SLS) or step-and-shoot" approach In delivering a beam shaped by an MLC-aperture, all cells inside the region of the MLC-aperture receive the same integral amount of radiation dose (say, one unit), i.e., the numbers for all such cells are decreased by the same integer value. The IM is done when all cells have a value zero.

Intuitively, an IM is a 3-D "mountain" made of unit cubes (see FIG. 6) and each MLC-aperture is an x-monotone polygonal "plateau" with a height. The goal is to "build" this mountain by stacking up a set of such plateaus (see FIGS. 4, 5 and 6). Note that each plateau, like the 3-D IM mountain, is not one whole "rigid" object, i.e., the mountain is made of unit cubes as well. Thus, when two plateaus are "stacked" together, some of the cubes may fall to lower levels as if they were pulled down by gravity. Geometrically, the SLS problem is to partition a 3-D IM mountain into a set of such plateaus.

A treatment plan for an input IM consists of a set of MLC-apertures (with their heights) for delivering the IM. Two key criteria are used to measure the quality of an IMRT treatment plan:

(1) Treatment time (efficiency): Minimizing the treatment time is crucial since it not only lowers the treatment cost of each patient but also increases the patient throughput. The overhead associated with repositioning the MLC leaves to form a different MLC-aperture dominates the total treatment time. Thus in one embodiment, the method of the present invention seeks to minimize the number of MLC-apertures for delivering each IM.

(2) Delivery error (accuracy): Due to the special geometric shapes of the MLC leaves (i.e., the "tongue-and-groove" interlock feature), an MLC-aperture cannot be delivered perfectly. Instead, there is a delivery error between the planned dose and actual delivered dose (also called the "tongue-and-groove" error in medical literature. Minimizing the delivery error is important because according to a recent study, the maximum delivery error can be as much as 10%, creating underdose/overdose spots in the target region. As described in detail below, any IM has a lowest amount of delivery error that is always achievable by choosing appropriate MLC-apertures.

The 3-D SLS problem has received a great deal of attention in medical physics, operations research, and computational geometry. However, most of the work has focused on minimizing the treatment time (closely related to minimizing the set of MLC-apertures while ignoring the issue on reducing the delivery error.

Theoretically, it has been shown by Chen et al, "Generalized Geometric Approaches for Leaf Sequencing Problems in Radiation Therapy. In 15th Annual International Symp. on Algorithms and Computation," December 2004 (hereinafter referred to as the "Chen et al. III" paper), the entire contents and disclosure of which is hereby incorporated by reference, that the 3-D SLS problem in general is NP-hard, and the combinatorial explosion of its structure crucially depends on the height of the input IM (i.e., largest value). The "Chen et al. III" paper gives an algorithm for the 3-D SLS problem with delivery error reduction, whose focus is on the trade-off between the error and number of MLC-apertures used. For example, subject to a given error bound, it finds an MLC-aperture set S such that |S| is minimized. The algorithm first partitions the given IM mountain into sub-IMs (i.e., 3-D mountains of a sufficiently small height), and then solves the problem separately on each sub-IM. A key case, called the basic case, is to deal with sub-IMs of a non-uniform height. The algorithm in the "Chen et al. III" paper for the basic case works as follows. Each 3-D IM mountain is viewed as consisting of a set of "mountain slices," one slice per column of the IM. Each mountain slice is delivered by an MLC leaf pair which forms a set of 3-D blocks, one by one. Such a set of blocks for delivering a mountain slice is called a delivery pattern. To compute an optimal set of MLC-apertures for the IM, the basic algorithm builds a graph G: (1) Generate all distinct patterns for each mountain slice, and let every vertex of G correspond to exactly one such pattern; (2) for any two patterns for two consecutive mountain slices, put left-to-right directed edges whose weights and costs are determined by the optimal weighted matchings between the blocks of the two patterns. The basic problem is then solved by finding a minimum cost k-weight shortest path in the graph G of the "Chen et al. III" paper.

Figure 28:
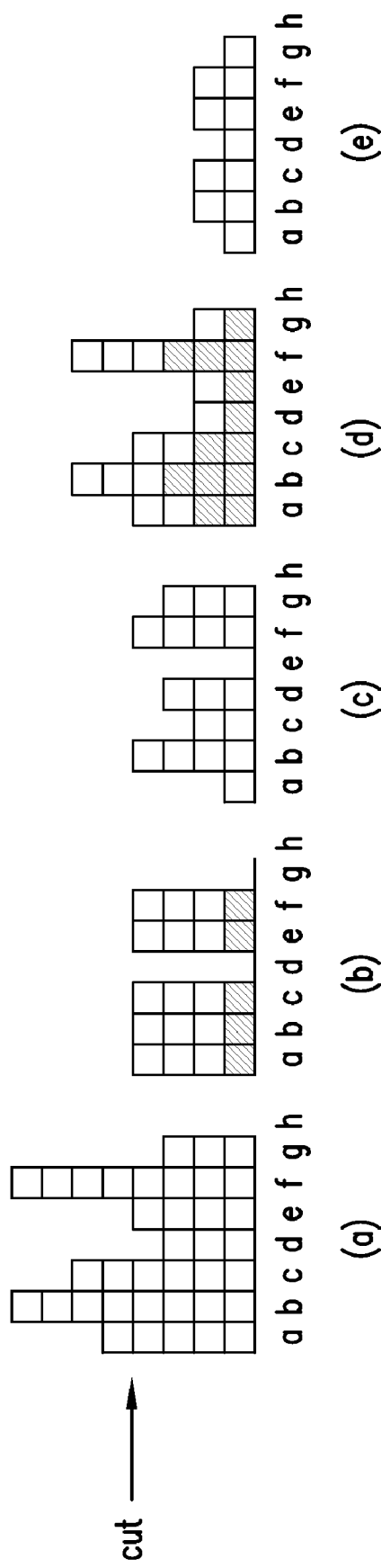
FIG. 28 shows (a) the dose profile curve (a wall) on an IM row, (b) and (c) two walls resulted from (a) by various cutting methods, where the one in (b) is a plateau and can be "shrunk" to a wall of height 1 (the shaded area), and where (d) and (e) are walls produced by the profile-preserving cutting method, of one embodiment of the present invention, without any new error. The wall in (d) can be shrunk to a wall of height 3 (the shaded area)

FIG. 28 shows: (a) the dose profile curve (a wall) on an IM row, (b) and (c) two walls resulted from (a) by the cutting methods described in the "Chen et al. I" paper and in the "Chen et al. III" paper and in, where the one in (b) is a plateau and can be "shrunk" to a wall of height 1 (the shaded area), and where (d) and (e) are walls produced by a profile-preserving cutting method, of one embodiment of the present invention, without any new error. The wall in (d) can be shrunk to a wall of height 3 (the shaded area). The height differences at location e in (a)-(e) are 1, 4, 3, 0, and 1, respectively.

Although the 3-D SLS algorithm in the "Chen et al. III" paper produces fairly good results, it is not suitable for computing a set of segments without machine delivery error:

(1) When dealing with IMs of large heights, the cutting schemes for partitioning an IM into sub-IMs of small heights may never achieve the lowest possible amount of delivery error. For example, cutting the dose profile curve, called a wall, of an IM row in FIG. 28 (a) at level 4 as in the "Chen et al. III" paper produces the two walls in FIG. 28(b) and FIG. 28(c). As shown below, the delivery error of an IM M may occur on the common boundary between any two adjacent cells $M_{i,j}$ and $M_{i,j}+1$, and the amount of error associated with this pair of cells is proportional to their absolute height difference, $|M_{i,j}-M_{i,j+1}|$. Note that by using the cutting schemes in the "Chen et al. III" paper, the sum of absolute height differences at position e in FIG. 28(b) and FIG. 28(c) is 7, while that at position e in FIG. 28(a) is only 1; thus, the cutting adds more error to position e in FIG. 28(b) and FIG. 28(c).

(2) The number of distinct patterns for delivering each mountain slice of an IM is a factorial function of its height. Thus, the size of the graph G used can be very large, which may significantly impact the running time of the 3-D SLS algorithm in the "Chen et al. III" paper. Hence, it is highly desirable to reduce the size of G by discarding unnecessary patterns without sacrificing the optimality of the solution.

(3) Computing optimal bipartite matchings between the blocks of two patterns for two consecutive mountain slices is a very frequent operation in [8] (performed for each edge of G). In the "Chen et al. III" paper such matchings are computed by the successive shortest path method for a general bipartite graph. It would be beneficial to develop a more efficient matching algorithm using the geometry of the pattern blocks.

Clinically, physicians may prefer to use MLC-apertures for IMs with the lowest possible error. As described below, when partitioning an IM into sub-IMs and MLC-apertures, any new error introduced will result in a treatment plan with an error larger than the lowest possible amount of delivery error. Hence, a key here is to develop a new IM partition algorithm that incurs no new error.

In one embodiment, the present invention provides a 3-D static leaf sequencing without new error (SLSWNE) method. Given an IM, the method finds a set S of MLC-apertures for delivering the IM such that (1) no new error is introduced by using S, and (2) |S| is minimized. A key special case of the 3-D SLSWNE problem, called the basic 3-D SLSWNE problem, is also important. This case is similar to the general 3-D SLSWNE problem, except that the height of each of its MLC-apertures is 1. Note that for the general 3-D SLSWNE problem, the height of each MLC-aperture can be any integer $\geq 1$. It is helpful to note that for the 3-D SLSWNE problem, two IM mountains A and B are computationally equivalent if $A = q \cdot B$ for some integer $q \geq 2$. This property, called the shrinkability, is due to the fact that two such IMs can be delivered by the same set of MLC-apertures with different heights. In one embodiment, the method of the present invention employs an algorithm for the 3-D SLSWNE problem, based on a number of novel ideas. First, in one embodiment the present invention provides a new scheme, called mountain reduction, for reducing a tall 3-D IM mountain to a small set of "low" sub-IM mountains that incur no new error. The mountain reduction scheme has two important operations: cutting and shrinking. In one embodiment, the cutting of the present invention is profile-preserving: An IM M is cut into two IMs qB and C (i.e., $M = q \cdot B + C$, where $q \geq 2$ is a chosen integer), such that qB and C have the same profile as M. For the purposes of the present invention, two IMs M' and M" have the same profile if for all $i, j, M'_{i,j} \geq M'_{i,j+1} \Leftrightarrow M''_{i,j} \geq M''_{i,j+1}$ and $M''_{i,j} \leq M'_{i,j+1} \Leftrightarrow M''_{i,j} \leq M''_{i,j+1}$ The profile-preserving cutting adds no new error to the resulting IMs qB and C since they keep the same sum of absolute height differences. Instead of cutting an IM mountain into a plateau and a mountain (and "shrinking" the plateau) as in the "Chen et al. III" paper the cutting produces qB and C so that qB can be shrunk into B (i.e., an algorithm of the present invention works on B instead of qB), see FIG. 28(d) and FIG. 28(e). Also, in one embodiment of the present invention C has a small height, so that the basic 3-D SLSWNE problem may be solved on C. The cutting method hinges on an optimal linear time algorithm for this profile-preserving mountain cutting problem, described below, which can be formulated as a bottleneck shortest path (BSP) problem on a DAG G' of a pseudo-polynomial size. By exploiting interesting properties of this DAG, it is possible to compute the BSP by searching only a small (linear size) portion of G'. For the basic 3-D SLSWNE problem, it is possible to make two major improvements. First, based on new geometric observations, it is possible to prove that only a small subset of patterns needs to be considered for delivering each mountain slice. More precisely, all blocks of a pattern should satisfy the so-called canonical condition, i.e., no block is contained in the interior of another block. This significantly decreases the number of patterns used for each mountain slice (and hence the size of the graph G). Second, a much better bipartite block matching algorithm is achieved. The minimum weight bipartite matching problem on blocks of canonical patterns, modeled by a bipartite graph of n vertices and m edges, may be formulated as a shortest path problem in a special weighted grid graph $G_g$. By exploiting the properties of this grid graph, it is possible to compute a shortest path in $G_g$ without explicitly building and searching the whole graph $G_g$, in $O(m+n)$ time, improving the previous $O(n(m+n \log n))$ time matching algorithm in the "Chen et al. III" paper. For the special case when the blocks can be matched without any new error, it is possible to give an optimal $O(n)$ time matching algorithm on such bipartite graphs.

By combining efficient solutions for the mountain reduction scheme and the basic 3-D SLSWNE problem, in one embodiment, the method of the present invention obtains an effective heuristic 3-D SLSWNE algorithm. Experiments and comparisons based on real medical data show that the algorithm is efficient and produces good quality treatment plans.

A mountain reduction scheme used in one embodiment of the present invention will now be described. The objective of the mountain reduction is to reduce a 3-D IM mountain of an arbitrary height into a small number of 3-D sub-IM mountains of sufficiently small heights without incurring any new error in the process. Each sub-IM thus resulted may then be handled by the basic 3-D SLSWNE algorithm, as described in more detail below.

The given IM is first "cut" into two IMs of smaller heights without incurring any new error. The new IMs are then recursively cut until all resulting IMs are of a sufficiently small height (say, $\leq 5$). At the heart of this recursive partition procedure is the following profile-preserving mountain cutting problem: Given an IM A and an integer $q \geq 2$, partition A into two IMs qB and C (i.e., $A = q \cdot B + C$) in a profile-preserving manner, such that the height of C is minimized. Since qB is shrinkable to B, the resulting IMs (B and C) have much smaller heights than the original IM A.

Some useful properties of the delivery error will now be described. For any two vectors $a = (a_1; a_2, \ldots, a_n)$ and $b = (b_1, b_2, \ldots, b_n)$ in $R^n$, the binary relation is define as "$\leq$" as $a \leq b$ if and only if $a_i \leq b_i$ for every $i = 1, 2, \ldots, n$. Similarly, $a \geq b$ if and only if $a_i \geq b_i$ for every $i = 1, 2, \ldots, n$.

The error-norm $\|A\|_E$ of an IM $A = (a_{hd\ i,j})_{m \times n}$ may be define as shown below in equation (I):

$$\|A\|_E = \sum_{t=1}^{m} \left( |a_{i,1}| + \sum_{j=1}^{n-1} |a_{i,j} - a_{i,j+1}| + |a_{i,n}| \right) \quad (I)$$

In one embodiment of the present invention, the delivery error of an IM is closely related to its error-norm. For example, when an IM A can be delivered as a single MLC-aperture (i.e., when no new error is added by the delivery of A), the delivery error for A is precisely $\alpha \|A\|_E$, where $\alpha > 0$ is a machine-dependent constant.

In fact, it can be proved that the error-norm $\|\cdot\|_E$ has the following properties:

(i) $\|kA\|_E = k\|A\|_E$, for any $k \geq 0$.

(ii) If $A = B + C$, then $\|A\|_E \leq \|B\|_E + \|C\|_E$ (iii) If $A = B + C$, then $\|A\|_E = \|B\|_E + \|C\|_E$
$\Leftrightarrow |a_{i,j} - a_{i,j+1}| = |b_{i,j} - b_{i,j+1}| + |c_{i,j} - c_{i,j+1}|$ for every $i = 1, 2, \ldots, n-1$
$\Leftrightarrow |(a_{i,j}, b_{i,j}, c_{i,j}) \leq (a_{i,j+1}, b_{i,j+1}, c_{i,j+1})$ or $\Leftrightarrow (a_{i,j}, b_{i,j}, c_{i,j}) \geq (a_{i,j+1}, b_{i,j+1}, c_{i,j+1})$ For every $i = 1, 2, \ldots, m$ and $j = 1, 2, \ldots, n-1$.

(iv) The minimum amount of error for delivering any IM A is $\alpha \|A\|_E$.

Property (iv) implies that an IM A is best delivered with an error of $\alpha \|A\|_E$. It is possible to say that an MLC-aperture set S for delivering A incurs additional error if the delivery error of S, $$\sum_{X \in S} \alpha \|X\|_E,$$

is larger than $\alpha \|A\|_E$. Let an IM A be partitioned into two IMs B and C. Then B and C are best delivered with an error of $\alpha(\|B\|_E + \|C\|_E)$. By Property (ii), unless the condition $\|A\|_E = \|B\|_E + \|C\|_E$ holds, the partition A=B+C will incur additional error. Property (iii) has two geometric interpretations: (1) The error is mainly associated with the absolute height difference of every two adjacent cells on an IM row, and the partition incurs no additional error if and only if the sum of the corresponding absolute height differences in the resulting IMs remains the same as the original absolute height difference; (2) a partition A=B+C incurs no new error if and only if it is profile-preserving, i.e., A, B, and C have the same profile. Intuitively, this means that the height increase/decrease occurred at any two adjacent cells $A_{i,j}$ and $A_{i,j+1}$ in A is preserved in both B and C accordingly.

The profile-preserving mountain cutting (PPMC) problem is: Given an m×n IM $$A = (a_{i,j}) \in Z_+^{m \times n}$$

and an integer $q \geq 2$, solve the following optimization problem:

$$\min_{B,C} \max_{i,j} c_{i,j}$$

subject to $B=(b_{i,j})$, $C=(c_{i,j}) \in Z_+^{m \times n}$ and an integer $q \geq 2$ solve the following optimization problem:

$$\min_{B,C} \max_{i,j} c_{i,j}$$

subject to: (1) $B=(b_{i,j})$, $C=(c_{i,j}) \in Z_+^{m \times n}$, (2) A=qB+C and (3) $(a_{i,j}, b_{i,j}, c_{i,j}) \leq (a_{i,j+1}, b_{i,j+1}, c_{i,j+1})$ or $(a_{i,j}, b_{i,j}, c_{i,j}) \geq (a_{i,j+1}, b_{i,j+1}, c_{i,j+1})$ for every i=1, 2, ..., m and j=1, 2, ..., n−1.

Constraint (3) means that A, B, and C are all of the same profile. Thus geometrically, the PPMC problem aims to cut a 3-D IM mountain A into two 3-D IM mountains qB and C in a profile-preserving manner, such that the height of C is minimized.

Observe that in the PPMC problem, the rows of the IMs (i.e., the walls) are completely independent to each other. Hence, the PPMC problem can be reduced to the following optimization problem, called the profile-preserving wall cutting (PPWC) problem: Given a row vector $a=(a_1; a_2, \ldots, a_n) \in Z_+^n$ of an IM mountain, which for the purposes of the present invention is called a wall, and an integer $q \geq 2$, seek $$\min_{B,C} \max_{i,j} c_i$$

subject to: (1) $b=(b_1, b_2, \ldots, b_n)$, $c=(c_1, c_2, \ldots, c_n) \in Z_+^n$, (2) a=qB+c, and (3) $(a_i, b_i, c_j) \leq (a_{i+1}, b_{i+1}, c_{i+1})$ or $(a_i, b_i, c_j) \geq (a_{i+1}, b_{i+1}, c_{i+1})$ for every I=1, 2, ..., n−1.

The PPWC problem may be formulated as a bottleneck shortest path (BSP) problem in a DAG G=(V,E) of a pseudo-polynomial size, and then present a simple optimal O(n) time PPWC algorithm by exploiting a number of special properties of the DAG G. FIG. 29(a) is an example of G and FIG. 29(a), (b), (c) and (d) illustrate (1a), (1b), (1c) and 1(d) of Lemma 6 described below.

Given an instance of the PPWC problem, $a(a_1, a_2, \ldots, a^n) \in Z_+^n$ and an integer $q \geq 2$, a directed graph G=(V,E) is defined for a and q, as follows. FIG. 29(a) gives an example of such a graph G.

The vertices of G are defined as $V = \{s,t\} \cup \{v_{i,j} | 1 \leq i \leq n, 0 \leq j \leq \lfloor a_i/q \rfloor\}$. Let $L_i$ denote the list of all vertices in the i-th layer of the graph G, i.e., $L_i = \{v_{i,j} \in V | 0 \leq j \leq \lfloor a_i/q \rfloor\}$. Then besides s and t, G has n layers of vertices. For each vertex $v_{i,j}$, the vertex is associated with an integer pair $$(b(vi, j), c(vi, j)) \triangleq (j, a_i - j_q).$$

For convenience, (b(s), c(s))=(b(t), c(t))=(0,0) is defined. The term b(u) (or c(u)) is called the b-index (or c-cost) of the vertex u. Note that for any i, the pairs $(b(v_i,j), c(v_i,j))$, $0 \leq j \leq \lfloor a_i/q \rfloor$, correspond to all possible solutions $(b_i, c_i)$ for the equation $a_i = q_i + c_i$, where $b_i = b(v_i,j)$, $c_i = c(v_i,j)$, and $b_i$, $c_i \in Z_+$. Hence, the vertices in Li correspond to all distinct ways to partition $a_i$ into $b_i$ and $c_i$. Also, observe that for each $L_i$, the sequence $b(vi,0), b(vi,1), \ldots, b(v_{i,\lfloor a_i/q \rfloor})$ is in increasing order, while the sequence $c(vi,0), \ldots, c(v_{i,\lfloor a_i/q \rfloor})$ is in decreasing order.

The edges of G are $\{(s,v_{a,j}) | 0 \leq j \leq \lfloor a_i/q \rfloor\} \cup \{\cup (v_{n,j},t) | 0 \leq j \leq \lfloor a_n/q \rfloor\} \cup \{(v_{i,j}, v_{i+1,k}) | (a_i, b(v_{i,j}), c(v_{i,j})) \leq (a_{i+1}, b(v_{i+1,k}), c(v_{i+1,k})$ or $(a_i, b(v_{i,j}), c(v_{i,j})) \geq (a_{i+1}, b(v_{i+1,k}), c(v_{i+1,k}))\}$ Obviously, G=(V,E) is a DAG with vertex weights. Each s-to-t path p in G is of the form of $p = s \to v_{1,j_1} \to v_{2,j_2} \to \ldots \to v_{n,j_n} \to t$, further, p corresponds to a feasible solution $b = (j_1, j_2, \ldots, j_n)$ and $c = (a_1 - j_1 q, a_2 - j_2 q, \ldots, a_n - j_n q)$ for the PPWC problem, and vice versa. For any s-to-t path p, the weight of p is defined as $w(p) = \max \{c(u) | u \in V, u$ is on $p\}$. Then an optimal solution for the PPWC problem corresponds to an s-to-t path p* in G such that w(p*) is minimized. Thus, the PPWC problem can be formulated as a bottleneck shortest path problem on the DAG G.

The DAG G thus defined has $O(n(\lfloor h/q \rfloor + 1))$ vertices and $O(n(\lfloor h/q \rfloor + 1)^2)$ edges, where $h = \max_i^n a_i$. An s-to-t bottleneck shortest path in G can be computed in $O(|V|+|E|) = O(n(\lfloor h/q \rfloor + 1)^2)$ time in a topological sort fashion. It should be noted that this algorithm, though straightforward, takes a pseudo-polynomial time and can be quite inefficient when h is much larger than q.

For any vertex $v \in V$, define $In(v) = \{w | (w, v) \in E\}$ and $Out(v) = \{w | (v, w) \in E\}$. For a subset $U \subseteq V$, denote by Max(U) the vertex in U that has the largest b-index. Let $V_s = \{v \in V |$ there is a path from s to v in G$\}$ and $V_t = \{v \in V |$ there is a path from v to t in $G_g\}$.

The PPWC algorithm hinges on a set of interesting observations on the DAG G defined above, as stated in Lemma 6 below.

Lemma 6: (6a) For any vertex $v_{i,j}$ in layer $L_i$ of G, the vertex set Out(vi,j) (or In(vi,j)), if non-empty, consists of vertices with consecutive b-indices (i.e., forming an interval) in layer $L_i+1$ (or $L_{i-1}$) of G. Moreover, a description of Out(vi,j) (or In(vi,j)) can be computed in O(1) time. (6b) For any vertices $v_{i-1,j_1}$, $v_{i-1,j_2}$, $v_i,k_1$, and $v_i,k_2$ of G, $j_1<j_2$ and $k_1<k_2$, if $(v_{i-1,j_1},v_{i,k_2}) \in E$ and $(v_{i-1,j_2},v_{i,k_1}) \in E$, then $(v_{i-1,j_2},v_{i,k_2}) \in E$. (6c) For any vertex $v_{i,j}$, if $v_{i,j} \in V_s$, then $v_{i,j'} \in V_s$ Vs for any $j' \leq j$ (6d) For any vertex $v_{i,j}$, if Out($v_{i-1,j}$)=Ø, then there exists a $j'<j$ such that $$\left( v_{i-1,j'} \cdot v_{i, \lfloor a_i/q \rfloor} \right) \in E.$$

Figure 29:
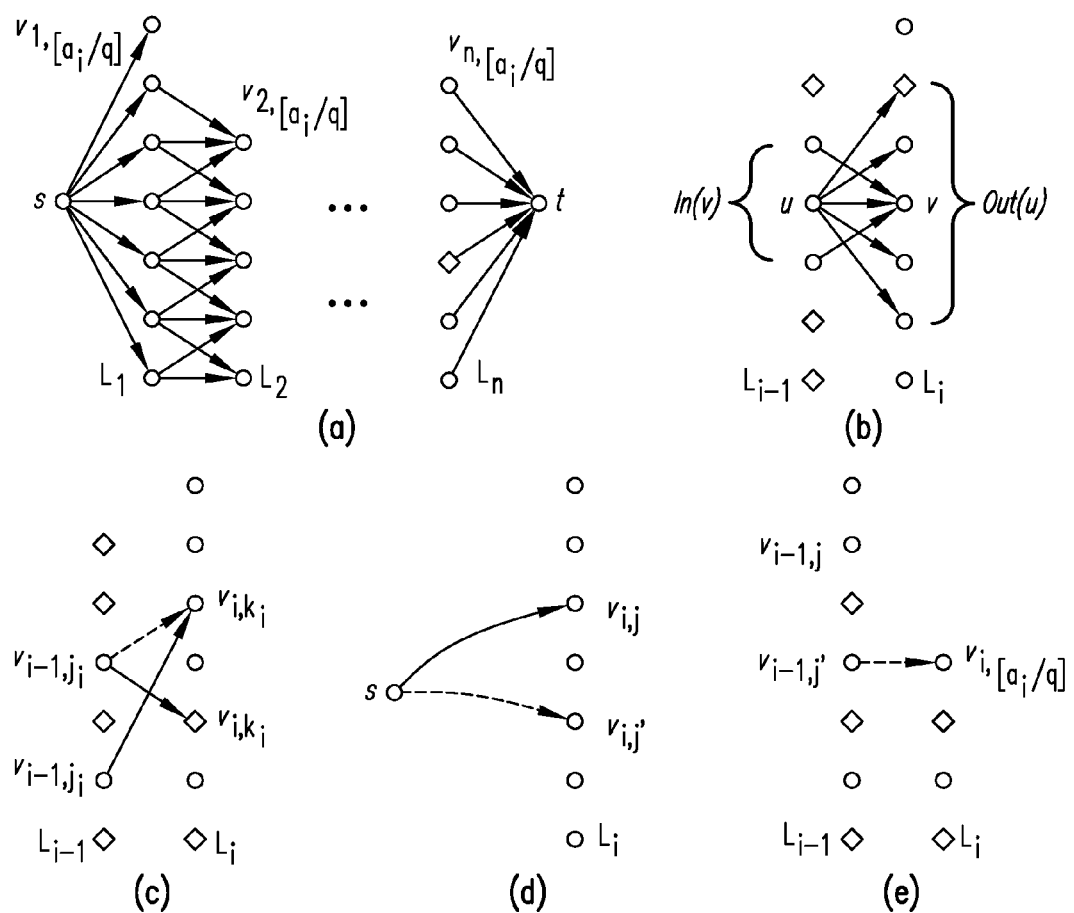
FIG. 29 is a directed graph and a lemma explained using the directed graph.

FIGS. 29 (b), (c), (d), and (e) illustrate the statements of Lemma 6. (6a) means that the edges leaving (or entering) a vertex always go to (or come from) vertices with consecutive b-indices. (6b) states the existence of a third edge whenever two edges "cross" each other. (6c) says that if a vertex $v \in L_i$ is reachable by the source s, then any vertex in Li with a smaller b-index than v is also reachable by s.

The PPWC algorithm computes two sets of vertices $u_i$ and $w_i$ in G, i=1, 2, ..., n, where $u_i$=Max($L_i \cap V_s$) is the vertex in layer $L_i$ with the largest b-index that is reachable by s, and $w_i$=Max($L_{in} \cap V_s V_t$) is the vertex in layer $L_i$ with the largest b-index that lies on some s-to-t path in G. It is shown below that the sought s-to-t bottleneck shortest path is $p^* = s \to w_1 \to w_2 \to \ldots \to w_n \to t$.

Figure 30:
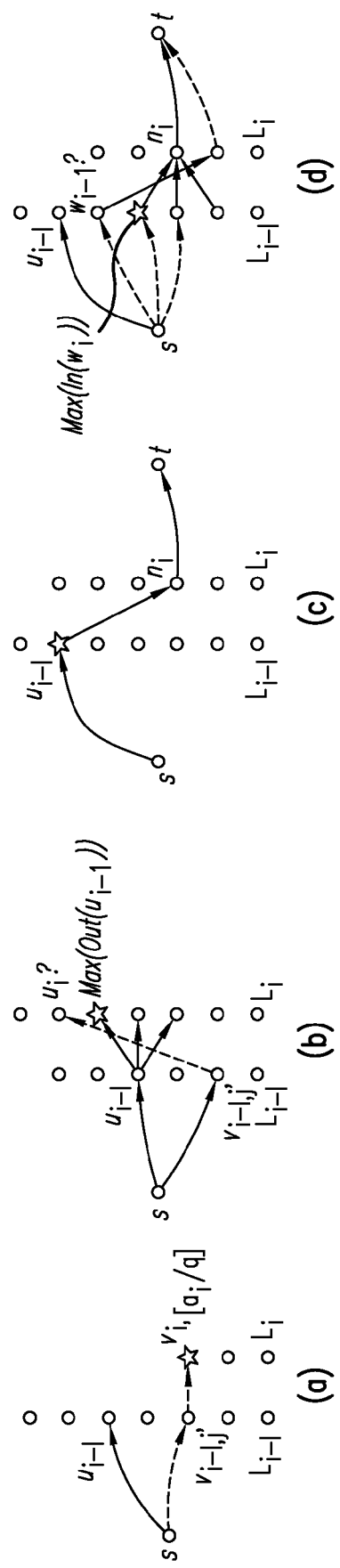
FIG. 30 is a series of diagrams illustrates the Profile Preserving Wall Cutting (PPWC) algorithm according to one embodiment of the present invention.

FIG. 30 is a series of diagrams illustrates the PPWC algorithm according to one embodiment of the present invention. FIGS. 30(a) and (b) illustrate the two possible cases when determining $u_i$ (marked by a star) from $u_{i-1}$ in the first phase of the PPWC algorithm. FIGS. 30(c) and (d) illustrate the two possible cases when determining $w_{i-1}$ (marked by a star) from $w_i$ in the second phase of the PPWC algorithm.

In one embodiment of the present invention, the optimal PPWC Algorithm consists of two phases. The first phase goes from $L_1$ to $L_n$, and determines $u_1, u_2, \ldots, u_n$, one by one. Since s is connected to each vertex in $L_1$, it is possible to start at $u_1 = v_{1, \lfloor a/q \rfloor}$. To determine ui from $u_{i-1}$, consider two possible cases. Case (1) Vertex $u_{i-1}$ has no outgoing edge, i.e., Out($u_{i-1}$)=Ø then $u_i=v_{i,\lfloor a_i/q \rfloor}$ (see FIG. 30(a)). This is because there is a $j'<j$ such that $v_{i-1,j'}, v_{i,\lfloor a/q \rfloor}) \in E$ (by (6d) of Lemma 6) and there is a path from s to $v_{i-1,j'}$ (by (6c) of Lemma 6). Case (2) Vertex $u_{i-1}$ has some outgoing edges, then $u_i$=Max(Out ($u_{i-1}$)) (see FIG. 30(b)). Clearly, Max(Out($u_{i-1}$)) is reachable by s. If $u_i \neq$Max(Out($u_{i-1}$)), then $u_i$ must have a b-index bigger than Max(Out($u_{i-1}$)) and $u_i \notin$Out($u_{i-1}$). But then a path from s to $u_i$ would "cross" the edge ($u_{i-1}$,Max(Out($u_{i-1}$))), making $u_i \in$Out($u_{i-1}$) (by (6b) of Lemma 6), a contradiction.

The second phase goes from $L_n$ to $L_1$, and determines $w_n$, $w_{n-1}, \ldots, w_1$, one by one. Since there is an edge from each vertex in layer $L_n$ to $t$, let $w_n=u_n$. To determine $w_{i-1}$ from $w_{i-1}$, consider two possible cases. Case (1) There is an edge connecting $u_{i-1}$ and $w_i$, then clearly $w_{i-1}=u_{i=1}$ (see FIG. (c)). Case (2) No edge connects $u_{i-1}$ and $w_i$, then $w_{i-1}$=Max(In(wi)) (see FIG. 30(d)). Note that in this case, $u_{i-1}$ must have a bigger b-index than some vertex in In(wi) since $w_i$ is reachable by s. By (6a) of Lemma 6, $u_{i-1}$ must have a bigger b-index than Max(In($w_i$)). Hence there is a path from s to Max(In($w_i$)) (by (6c) of Lemma 6). If $w_{i-1} \neq$Max(In($w_i$)), then $w_{i-1}$ must have a bigger b-index than Max(In($w_i$)) and $w_{i-1} \notin$In($w_i$). But then an s-to-t path passing through $w_{i-1}$ would "cross" the edge (Max(In($w_i$)),$w_i$), making $w_{i-1} \in$In($w_i$) (by (6b) of Lemma 6), a contradiction.

Therefore, $p^* = s \to w_1 \to w_2 \to \ldots \to w_n \to t$ is the sought s-to-t bottleneck shortest path. Note that $(w_{i-1},w_i) \in E$ holds for both Cases (1) and (2) of the second phase. Thus $p^*$ is indeed an s-to-t path in G. Since $w_i$=Max($L_i \cap V_s \cap V_t$), for any path $p=s \to v_{1,j_1} \to v_{2,j_2} \to \ldots \to v_{n,j_n} \to t$ in G, $b(w_i) \geq b(v_{i,j_i})$, or equivalently $c(w_i) \leq c(v_{i,j_i})$, holds for each i=1, 2, ..., n. Hence $w(p^*) \leq w(p)$.

Note that although it is possible to formulate the PPWC problem as a bottleneck shortest path problem on the DAG G, G–G is not explicitly constructed and is merely a conceptual structure to help with the description of the of the algorithm. It is easy to show that the two phases take totally O(n) time.

Theorem 4. Given a vector (wall) $a=(a_1, a_2, \ldots, a_n) \in Z_+^n$ and an integer $q \geq 2$, the PPWC problem on the vector a can be solved in an optimal O(n) time.

The relation between the PPMC and PPWC problems implies the following.

Theorem 5. Given an m×n 3-D IM mountain $A=(a_{i,j}) \in Z_+^{m \times n}$ and an integer $q \geq 2$, the PPMC problem on A can be solved in an optimal O(n) time.

In one embodiment of the present invention, the mountain reduction scheme is based on the PPMC algorithm described above. Given a 3-D IM A of an arbitrary height, one chooses an integer $q \geq 2$ as the divisor, and apply the PPMC algorithm to cut A into two IMs qB and C (i.e., A=qB+C). After shrinking qB to B, the result is two IMs B and C of smaller heights. The resulting IMs are then recursively cut and shrink, until they are all of a sufficiently small height (say, $\leq 5$). Since the cutting and shrinking are profile-preserving, the input IM A is reduced to a set of IMs of small heights (called sub-IMs) without incurring any new error.

Now the procedure for choosing a divisor q for each cut will be described. Note that in some embodiments of the present invention, it is desirable to keep the number of sub-IMs produced by the mountain reduction small. For each cut in the above recursive process, several integers are tried as the candidates for q, and a set of values for q is chosen that together yield the smallest number of sub-IMs at the end of the recursive process, based on dynamic programming.

The algorithm for the basic 3-D SLSWNE problem, i.e., partitioning a given 3-D IM of a small height (say, $\leq 5$) into a minimum set of MLC-apertures of a unit height each, such that no new error is added. Such an IM may be produced by the mountain reduction scheme previously described, will now be described.

In one embodiment of the present invention, the 3-D SLSWNE algorithm follows the same framework as described in the "Chen et al. III" paper, but with several key changes. (1) Only a small subset of patterns are considered for each mountain slice, such that all blocks of a pattern to satisfy the so-called canonical condition, such patterns are sufficient to guarantee the optimality (see below). (2) New algorithms are given for the block matching problem by exploiting the canonical condition (see below). (3) Instead of computing a minimum cost k-weight shortest path as in the "Chen et al. III" paper, an optimal MLC-aperture set is obtained by computing a shortest path in a graph.

Let $P=\{I_i | 1 \leq i \leq k\}$ be a delivery pattern of size k for an IM column of length m, in which the i-th block (of a unit height) is specified by a close interval $I_i=[a_i, b_i]$, $a_i, b_i, \in \{0, 1, \ldots, m\}$ (i.e., P can be used to deliver the mountain slice of the IM column). P is called a canonical pattern if it satisfies the canonical condition: For any two $I_i$ and $I_j$ in P, i≠j, neither $[a_i, b_i] \subset (a_j, b_j)$ nor $[a_j, b_j] \subset (a_i, b_i)$ (no interval is contained in the interior of the other interval). Clearly, the endpoints of the blocks of a canonical pattern P can be ordered such that $a_1 \leq a_2 \leq \ldots \leq a_k$ and $b_1 \leq b_2 \leq \ldots \leq b_k$. Moreover, this ordering can be easily obtained in linear time from the corresponding mountain slice description.

Lemma 7 below states the optimality of any basic SLSWNE solution using only canonical patterns.

Figure 31:
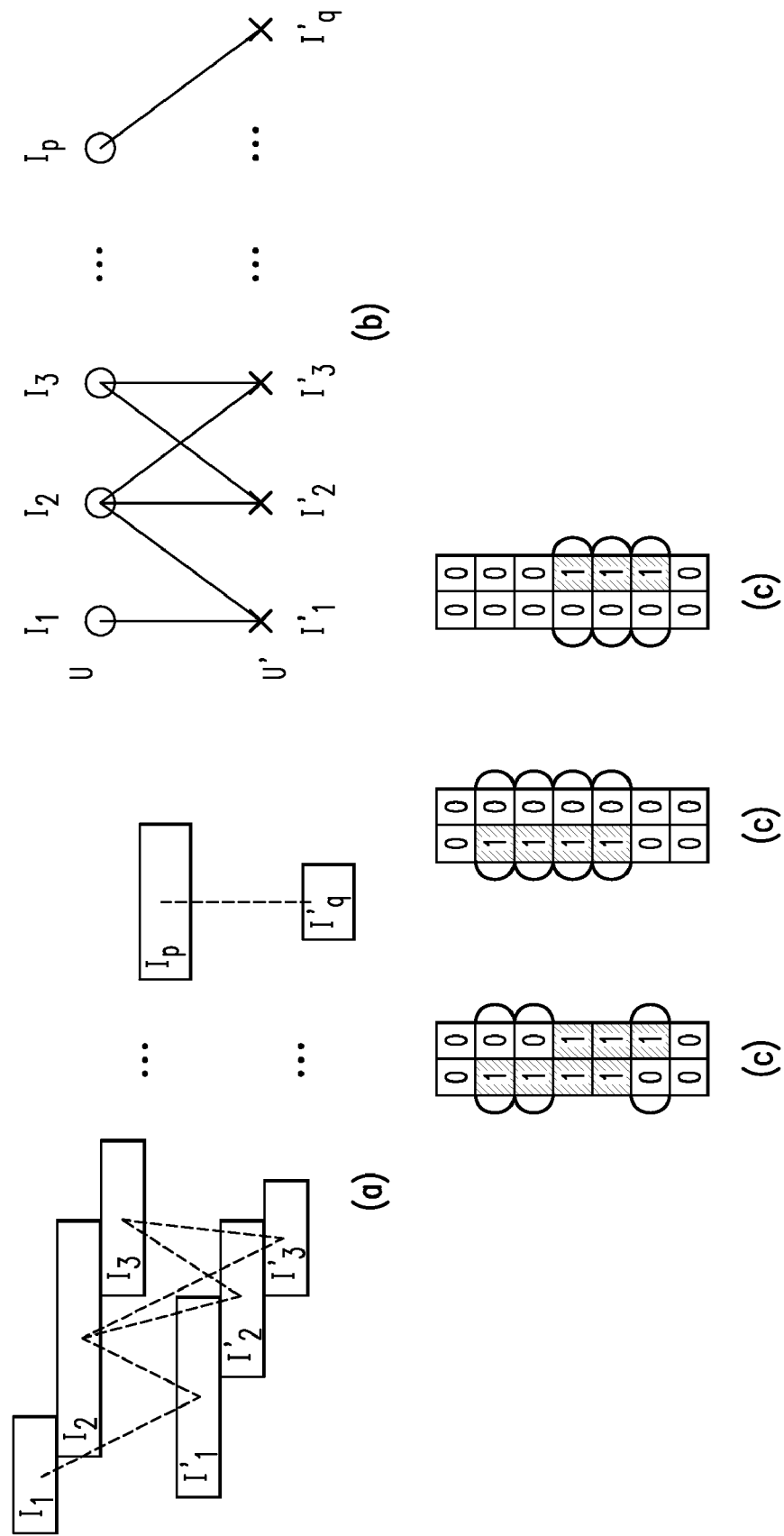
FIG. 31 is a diagram of two canonical patterns, their bipartite graph, a diagram of the error for a matched block pair, and two diagrams of error for unmatched block pairs in accordance with one embodiment of the present invention.

FIG. 31 is a diagram of two canonical patterns, their bipartite graph, a diagram of the error for a matched block pair, and two diagrams of error for unmatched block pairs in accordance with one embodiment of the present invention. FIGS. 31(a) and (b) show two canonical patterns and their bipartite graph. FIG. 31(c) shows the error of a matched block pair (occurring at the circled cell pairs). FIGS. 31(d) and (e) each show the error of an unmatched block. The error in FIGS. 31(c), (d), and (e) is 3, 4, and 3, respectively.

Lemma 7. For the basic 3-D SLSWNE problem, it is sufficient to use only the canonical patterns for each column $C_j$ of the input IM M to compute an optimal MLC-aperture set for M.

By Lemma 7, it is possible to use only canonical patterns in computing an optimal basic 3-D SLSWNE solution. Note that canonical patterns can be defined by adding Steiner points onto each IM column as described in the "Chen et al. I" and the "Chen et al. III" papers. Experiments indicate that only O(1) Steiner points are practically sufficient for each IM column. Thus, in one embodiment of the present invention, the 3-D SLSWNE algorithm uses only a polynomial number of canonical patterns.

The modeling of the block matching problems will now be described, followed by the algorithms for the block matching problems, First, the definition of the block matching problem and its meaning will be described. Let $U=\{I_1, I_2, \ldots, I_p\}$ ($U'=\{I'_1, I'_2, \ldots, I'_q\}$ be sorted canonical pattern for the j-th ((j+1)-th) column of an IM T, an interval $I_k=|a_k,b_k|$ ($I_l=|a'_l, b'_l|$) specifies a unit height block of U, (U'). Let $G_b=U \cup U'$, E be a bipartite graph (FIGS. 31(a) and (b)), with $E=\{(I_k,I'_l)|(a_k, b_k) \cup (a'_l, b'_l) \neq \emptyset\}$. Define the weight of a vertex $v=[a, b] \in U \cup U'$ as $w_V(v)=|a-b|$, and the weight of an edge $e=I_k,I'_l \in E$ as $w_E(e)=|a_k-a'_l|+|b_k-b'_l|$. For a matching M in $G_b$, let its weight $$w(M) \triangleq \sum_{e \in U \cup U'},$$

$_{v \text{ is unmatched}} w_V(v)$. The block matching (BM) problem seeks a matching M* in Gb, such that $(w(M^*),-|M^*|)$ is minimized. Tuples are compared in the lexicographical manner.

Note that in general, $G_b$ is not a complete bipartite graph due to the MLC constraints, i.e., only blocks with non-empty interior overlapping can be matched. Recall that the error associated with a pair of horizontally consecutive IM cells is proportional to the absolute height difference of the cells. Hence $w_V(v)$ (or $w_E(e)$) thus defined captures the error incurred by an unmatched block (or a pair of matched blocks) (see FIGS. 31 (c), (d) and (e)), and w(M) represents the total error incurred by the matching M. The block matching problem seeks, among all matchings that incur the minimum error, the one with the maximum cardinality. Of course, the embodiment of the present invention be currently described, the SLSWNE problem desires zero new error.

The error incurred by a matching depends on the patterns U and U' involved. For any two patterns that deliver for the j-th and (j+1)-th columns of the IM T respectively, a matching between the blocks of the two patterns must incur an error whose lower bound is $$\sum_{i=1}^{m} |T_{i,j} - T_{i,j+1}|.$$

Such a matching M is without new error if $$w(M) = \sum_{i=1}^{m} |T_{i,j} - T_{i,j+1}|.$$

Further, the block matching without new error (BMWNE) problem is defined as one of finding a maximum cardinality matching M' in the bipartite graph $G_b$ such that M' is without new error.

The BMWNE problem is closely related to the BM problem. Let M be a solution for the BM problem on the graph $G_b$. If M* is without new error, then it is also a solution for the BMWNE problem; otherwise, no solution exists for the BMVWNE problem on $G_b$.

Below is described an algorithm for the BM problem in accordance with one embodiment of the present invention. One key observation is that because both the sets of blocks involved are canonical, the BM problem has an optimal substructure, which leads to a formulation of the BM problem as a shortest path problem on a special weighted grid graph. The BM problem on $G_b$ is in fact a minimum-cost matching problem. Simply assign each vertex v a cost of $C_V(v)=(w_V(v), 1)$, assign each edge e a cost of $C_E(e)=(w_E(e), 1)$, and define the cost of a matching M as $C(M)=C(M)=\Sigma_{e \in M} C_E(e) + \Sigma_{e \in U \cup U', v \text{ is unmatched}} C_V(v)$. The, $(C(M)=(w(M), |M|+p+q)$, and the BM problem becomes that of finding a matching M* such that C(M*) is minimized. The graph $G_b$ defined above has useful properties.

FIG. 32 is a grid graph and diagrams illustrating the edges of the grid graph; FIG. 32 (a) is the grid graph $G_g$ (all edges of $G_g$ are directed upwards, rightwards, or both). FIG. 32 (b) illustrates the edges and their lengths in $G_g$. FIG. 32(c) illustrates the edges and their lengths in $G'_g$.

Lemma 8. (8a) $G_b$ is a convex bipartite graph, i.e., for any k (or l), the set $N(k)=\{l|(I_k, I'_l) \in E\}$ or $N'(l)=\{k|(I_k,I'_l) \in E$ if non-empty, consists of consecutive indices, say, from $c_k$ (or $c'_l$) to $d_k$ (or $d'_l$). Further, the sequences $\{c_k\}_{k=1}^P$, $\{d_k\}_{k=1}^P$, $\{c'_k\}_{k=1}^P$, and $\{d'_k\}_{k=1}^P$, are all increasing. (8b) Given $I_1, I_2, \ldots, I_p$ and $I'_1, I'_2, \ldots, I'_q$ the description of all the sets $N(1)$, $N(2), \ldots, N(p)$ and $N'_1, N'_2, \ldots, N'_p$ can be computed in $O(p+q)$ time. (8c) For any $k_1<k_2$ and $l_1<l_2$, if $e_1=(I_{k_1},I'_{l_2}) \in E$ and $e_2=(I_{k_2},I'_{l_1}) \in E$ then $e'_1=(I_{k_1},I'_{l_1}) \in E$ and $e'_2=(I_{k_2},I'_{l_2}) \in E$. Moreover, $C_E(e'_1)+C_E(e'_2) \leq C_E(e_1)+C_E(e_2)$.

By (8c) of Lemma 8, it is sufficient to consider matchings that have no "crossing" edges. This implies the following optimal substructure of the BM problem.

Lemma 9. Let $H_{k,l}$ be the subgraph of $G_b$ induced by the vertex sets $\{I_1, I_2, \ldots, I_k\}$ and $\{I'_1, I'_2, \ldots, I'_l\}$, for $k \in \{1, 2, \ldots, p\}$ and $l \in \{1, 2, \ldots, q\}$, Let $M_{k,l}$ be a minimum-cost matching in $H_{k,l}$ and $e=(I_{k_j},I'_l)$. 1. If $e \in M_{k,l}$, then $M_{k,l}-\{e\}$ is a minimum-cost matching in $H_{k-1,l-1}$. 2. If $e \notin M_{k,l}$, then $I_k$ (or $I'_l$) is unmatched, then $M_{k,l}$ is a minimum-cost matching in $H_{k-1,l}$ (or $H_{k,l-1}$).

Let $c_{k,l}$ denote the cost of $M_{k,l}$. Then Lemma 9 implies the following recursive formula: $c_{k,l}=$ (0,0), if $k=l=0$, $c_{k-1,l}+C_V(I_k)$, if $k>0$ and $l=0$, $c_{k,l-1}+C_V(I'_l)$, if $l>0$ and $k=0$, $\min\{c_{k-1,l}+C_V(I_k), c_{k,l-1}+C_V(I'_l)\}$, if $k, l>0$ and $(I_k,I'_l) \notin E$, or $\min\{c_{k-1,l}+C_V(I_k), c_{k,l-1}+C_V(I'_l), c_{k-1,l-1}+C_E((I_k,I'_l))\}$, if $k, l>0$ and $(I_k, I'_l) \in E$.

Hence, it is possible to transform the BM problem to a shortest path problem on a directed grid graph $G_g$ (see FIGS. 32(a) and (b)). Each vertex $g_{k,l}$ in $G_g$ corresponds to the BM problem on $H_{k,l}$. The length of a horizontal (or vertical) edge $(g_{k,l-1}, g_{k,l})$ (or $(g_{k,l-1}, g_{k,l})$) is $C_V(I_k)$ (or $C_V(I'_l)$); the length of a diagonal edge $(g_{k-1,l-1}, g_{k,l})$ is $C_E((I_k,I'_l))$. Note that a diagonal edge $(g_{k-1,l-1}, g_{k,l})$ is in $G_g$ if and only if $(I_k,I'_l) \in E(G_b)$. Let $SP_{k,l}$ be a shortest $g_{0,0}$-to-$g_{k,l}$ path in $G_g$. Clearly, $c_{k,l}=$length $(SP_{k,l})$; each diagonal edge $(g_{k_1-l,l_1-1}, g_{k_1,l_1})$ on $SP_{k,l}$ corresponds to the edge $(I_k,I'_l)$ in the matching $M_{k,l}$.

It will now be shown how to compute $SP_{p,q}$ in $G_g$. Observe that if every grid cell of $G_g$ is "colored" that contains a diagonal edge, then by Lemma 8, the colored region consists of a set of x(y)-monotone rectilinear polygons, which can be connected by line segments on the grid to form a single (degenerate) x(y)-monotone rectilinear polygon R (see FIG. 32(a)). In one embodiment of the present invention, It is sufficient to compute $SP_p$,q in R. This is because it is possible to always "push" the portion of an optimal $g_{0,0}$-to-$g_{p,q}$ path that lies outside R towards R until it coincides with R's boundary, without changing the length of the path.

Determining the region R in the $G_g$ grid is essentially done by computing the sets $N(1), N(2), \ldots, N(p)$ as defined in Lemma 8, which takes $O(p+q)$ time. The subgraph of $G_g$ induced by R is a DAG of size $O(p+q+|E(G_b)|)$. Thus, it follows that $SP_{p,q}$ can be computed in $O(p+q+|E(G_b)|)$ time.

Theorem 6. The BM problem on the bipartite graph $G_b=(U \cup U',E)$ induced by two canonical patterns U and U' for any two IM columns can be solved in $O(|U|+|U'|+|E|)$ time.

Note that in one embodiment of the present invention, the 3-D SLSWNE algorithm clearly relies on the BMWNE solution, while the BM algorithm is useful to the SLS algorithm described in the "Chen et al. III" paper (for a tradeoff between the MLC-aperture number and error). Although the BMWNE problem can be solved by the BM algorithm, described above, due to the relation between these two problems, a faster BMWNE algorithm is possible.

Recall that an MLC-aperture set incurs no new error if and only if each of its MLC-apertures is profile-preserving. A matched block pair (or an unmatched block) may be viewed as an MLC-aperture. Hence, the BMWNE problem is to seek a maximum cardinality matching such that all matched block pairs and unmatched blocks are profile-preserving. A matched block pair (or an unmatched block) is admissible if the corresponding MLC-aperture is profile-preserving. A new bipartite graph $G_b$ is defined where $G_b=(U \cup U',E)$, where $E'=\{(I_k,I'_l) \in E | (I_k,I'_k)$ is admissible$\}$, and let the cost $C_V(v)=1$ (or $+\infty$) for each admissible (or inadmissible) vertex v, and $C_E(e)=1$ for each edge $e \in E'$. Then, the BMWNE problem can be viewed as a minimum-cost matching problem on $G'_b$.

It can be can proven that $G'_b$ has all the properties stated in Lemmas 8 and 9 and some additional properties on its edge structures; also, the same recursive formula for computing $c_{k,l}$ applies. Thus, the BMWNE problem can be solved in the same spirit as the BM algorithm, i.e., it is possible to transform the BMWNE problem on $G'_b$ to computing a shortest path $SP_{p,q}$ in a directed grid graph $G'_g$ (see FIG. 32). A shortest path $SP_{p,q}$ in $G'_g$ can be computed in $O(p+q)$ time.

Theorem 7. The BMWNE problem on the bipartite graph $G_b=(U \cup U',E)$ induced by two canonical patterns U and U' for any two IM columns of size m each can be solved in $O(|U|+|U'|+m)$ time.

The error control method of the present invention, may be used with various segmentation and partition methods, including the partition and segmentation methods described in concurrently filed U.S. patent application, Attorney Docket No. UNND-0064-UT1, entitled "Segmentation Algorithmic Approach to Step-and-Shoot Intensity Modulated Radiation Therapy," the entire contents and disclosure of which are hereby incorporated by reference.

In one embodiment, the present invention provides a method comprising the following steps: (a) partitioning an intensity modulated beam into a set of sub-IMBs; and (b) partitioning the sub-IMBs into segments, wherein steps (a) and (b) introduce no machine delivery error. In one embodiment of the present invention, step (a) further comprises the following steps: (c) choosing a divisor q; (d) splitting an intensity modulated beam A into two sub-IMBs B and C, such that A=qB+C, where the splitting does not introduce machine delivery error; and (e) recursively partitioning the two sub-IMBs B and C until there is no sub-IMB whose maximum height is more than 5.

In one embodiment of the present invention, the divisor q further satisfies the following relationship: $2 \leq q \leq I_{max}/2$, where $I_{max}$ is the maximum entry in the intensity modulated beam. In one embodiment of the present invention, step (d) further comprises the following steps: (f) splitting every row of intensity modulated beam A into two sub-rows; and (g) extracting the two sub-IMBs B and C from the sub rows generated. In one embodiment of the present invention, step (f) comprises of the following steps: (h) constructing a directed graph based on each row of intensity modulated beam A; (i) determining a bottleneck shortest path in the directed graph; (0) extracting the sub rows from the directed graph based on the bottleneck shortest path determined in step (i) to thereby split the row. In one embodiment of the present invention, step (h) further comprises the following steps: (k) constructing an empty directed graph; (l) for each grid cell in the row, adding a layer of $1+\lfloor k/q \rfloor$ first vertices to the directed graph, where k is the intensity level at the grid cell; (j) assigning each vertex of said vertices with two integers, a weight and an index; (k) adding a source vertex and a sink vertex to the directed graph; (l) adding edges to the directed graph from the source vertex to every vertex of said first vertices in the first layer, and from every vertex of said first vertices in the last layer to the sink vertex; and (m) adding edges between any two vertices in the directed graph if the vertices respectively lie in adjacent layers and if the associated integers of one vertex are all larger than or equal to the corresponding integers of the other vertex.

In one embodiment of the present invention, step (b) comprises the following steps: (c) generating a canonical delivery option for each set of field opening endpoints for a plurality of intensity modulated beam columns of the sub-IMB; (d) for every two consecutive intensity modulated beam columns, determining a maximum matching with no machine delivery error between the canonical delivery options of the intensity modulated beam columns; and (e) extracting the segments for the sub-IMB based on the matched field openings of the canonical delivery options in an increasing order of consecutive intensity modulated beam columns to thereby partition the sub-IMB. In one embodiment of the present invention, in step (c) only one set of left and right field opening endpoints is generated for each intensity beam column. In one embodiment of the present invention, in step (c) more than one set of left and right field opening endpoints is generated for each intensity beam column. In one embodiment of the present invention, the matched field openings have no interdigitation. In one embodiment of the present invention, the method further comprises choosing a number m of Steiner points for forming the sets of field opening endpoints, and wherein each unique canonical delivery option contains at most m Steiner points for each set of field opening endpoints. In one embodiment of the present invention, step (d) further comprises the following steps: (f) constructing a directed graph based on the canonical delivery options of the intensity modulated beam columns; (g) determining a shortest path in the directed graph constructed in step (c); and (h) extracting the optimal matching between the canonical delivery options from the shortest path determined in step (d). In one embodiment of the present invention, step (c) further comprises: (f) constructing a directed graph of a grid of p+1 rows and q+1 columns of vertices, wherein p and q are the numbers of leaf openings in the left and right canonical delivery options respectively; (g) for any vertex pair u and v, wherein u lies in the i-th row and j-th column, and v lies in the i-th row and (j+1)-th column in the directed graph constructed in step (f), adding an edge to the directed graph from u to v, and assigning a weight (x,1) to the edge, wherein x is the length of the j-th leaf opening in the right canonical delivery option; (h) for any vertex pair u and v, wherein u lies in the i-th row and j-th column, and v lies in the (i+1)-th row and j-th column in the directed graph constructed in step (f), adding an edge to the directed graph from u to v and assigning a weight (y,1) to the edge, wherein y is the length of the i-th leaf opening in the left canonical delivery option; and (i) for any vertex pair u and v, wherein u lies in the i-th row and j-th column, and v lies in the (i+1)-th row and (j+1)-th column in the directed graph constructed in step (f), if the i-th leaf opening in the left canonical delivery option and the j-th leaf opening in the right canonical delivery option have non-empty interior overlapping, adding an edge to the directed graph from u to v and assigning a weight (z,1) to the edge, wherein z is the symmetric difference between the two leaf openings.

In one embodiment, the present invention provides a method comprising the following steps: (a) recursively partitioning an intensity modulated beam into plateaus; and (b) partitioning the plateaus into segments, wherein step (a) comprises determining a tradeoff between machine delivery error and the number of segments into which the plateaus will be partitioned in step (b). In one embodiment of the present invention, step (b) comprises the following the steps: (c) constructing a directed graph based on the plateaus; (d) determining a series of minimum cost flows in the directed graph; (e) determining a tradeoff between the number of segments and machine delivery errors based on the determined minimum cost flows, and (f) extracting the segments from the directed graph based on the tradeoff determined in step (e) to thereby partition the plateaus. In one embodiment of the present invention, step (c) comprises the following steps: (g) constructing a directed graph based on intensity modulated beam grids of the plateaus of an intensity modulated beam, wherein vertices of the directed graph include all intersection points of the intensity modulated beam grids of the plateaus that are either part of a peak or an interior of a polygon corresponding to the intensity modulated beam, and wherein the edges of the directed graph include those edges of the plateaus whose end points are graph vertices in the directed graph; (h) for all graph vertices corresponding to the same peak direction, adding either a source vertex or sink vertex to the directed graph; (i) adding edges to the directed graph from the source vertex or sink vertex to respective peak vertices; (j) assigning a unit flow capacity to each graph vertex and edge of the directed graph; and (k) to each edge that is vertical assigning a cost that is equal to the geometric length of the vertical edge, and to each edge that is horizontal a cost of zero. In one embodiment of the present invention, step (g) comprises the following steps: (l) extracting connections between a left peak and a right peak of the polygon based on the minimum cost flow; (k) eliminating any remaining unconnected peaks using only horizontal edges; and (l) extracting resulting segments from the directed graph to thereby partition the plateaus. In one embodiment of the present invention, for an edge involving a left peak vertex, the direction of the edge is away from the left peak wherein for an edge involving a right peak vertex, the direction of the edge is toward the right peak. In one embodiment of the present invention, the direction of a horizontal edge that does not involve any peak vertex is from left to right. In one embodiment of the present invention, the direction of a vertical edge that does not involve a peak vertex is bidirectional In one embodiment of the present invention, for all left peak vertices, a source vertex is added to the directed graph. In one embodiment of the present invention, for all right peak vertices, a sink vertex is added to the directed graph. In one embodiment of the present invention, the minimum cost flow in the directed graph yields a maximum set of mutually disjoint paths. In one embodiment of the present invention, the intensity modulated beam comprises a plurality of z-posts, and wherein step (a) comprises the following steps: (c) choosing an intensity level d wherein, $1 \leq \leq I_{max}$, wherein $I_{max}$ is the maximum intensity level of the intensity modulated beam; (d) selecting all z-posts having a height of at least d to form a set of selected z-posts; (e) cutting each selected z-post whose height is $\geq d$ at level d to form a plateau of z-posts of height d; (f) removing the plateau of z-posts from the intensity modulated beam; and (g) recursively partitioning any remaining portion of the intensity modulated beam until there is no remaining portion of the intensity modulated beam. In one embodiment of the present invention, step (g) comprises repeating steps (c), (d), (e) and (f) on any remaining portion of the intensity modulated beam until there is no remaining portion of the intensity modulated beam.

In one embodiment of the present invention, d is a function of the maximum intensity level $I_{max}$. In one embodiment of the present invention, $$d = \left\lceil \frac{I_{max}}{2} \right\rceil.$$

In one embodiment of the present invention, d is based on the volume of the plateau of z-posts. In one embodiment of the present invention, $d=2^i$, where $i=\text{Int}(\log_2(I_{max}))-1$. In one embodiment of the present invention, d has a value such that the volume of the plateau of z-posts is maximized. In one embodiment of the present invention, d is determined by the slice method. In one embodiment of the present invention, step (a) further comprises: partitioning the intensity modulated beam into a sub-IMB, and wherein the method further comprises the following step: (c) determining the tradeoff curve between the number of segments and error for the sub-IMB.

In one embodiment of the present invention, step (c) comprises the following steps: (d) generating a canonical delivery option for each set of field opening endpoints for a plurality of intensity modulated beam columns of the sub-IMB; (e) for every two consecutive intensity modulated beam columns, determining a series of minimum cost g-matchings between the canonical delivery options of the intensity modulated beam columns; (f) determining the tradeoff curves based on the g-matchings; and (g) extracting the segments for the sub-IMB based on the matched field openings of the canonical delivery options from the determined g-matchings in an increasing order of consecutive intensity modulated beam columns to thereby partition the sub-IMB. In one embodiment of the present invention, in step (d) only one set of left and right field opening endpoints is generated for each intensity beam column. In one embodiment of the present invention, in step (d) more than one set of left and right field opening endpoints is generated for each intensity beam column. In one embodiment of the present invention, the matched field openings have no interdigitation and minimum leaf separation. In one embodiment of the present invention, the matched field openings have no minimum leaf separation and no interdigitation. In one embodiment of the present invention, the matched field openings have interdigitation. In one embodiment of the present invention, the method further comprises choosing a number m of Steiner points for forming the sets of field opening endpoints, and wherein each unique canonical delivery option contains at most m Steiner points for each set of field opening endpoints.

In one embodiment, the present invention provides a method comprising the following steps: (a) recursively partitioning an intensity modulated beam into plateaus; (b) partitioning the plateaus into segments, wherein step (a) comprises determining a tradeoff between machine delivery error and the number of segments into which the plateaus will be partitioned in step (b); and (c) linking the segments to thereby reduce the number of segments. In one embodiment of the present invention, step (a) further comprises the following steps: (d) recursively partitioning an intensity modulated beam into plateaus; and (e) partitioning the plateaus into segments, wherein step (a) comprises determining a tradeoff between machine delivery error and the number of segments into which the plateaus will be partitioned in step (b). In one embodiment of the present invention, step (d) further comprises: partitioning the intensity modulated beam into a sub-IMB, and wherein the method further comprises the following step: (f) determining the tradeoff curve between the number of segments and error for the sub-IMB. In one embodiment of the present invention, step (c) further comprises the following steps: (d) constructing a directed graph H based on the segments extracted; (e) determining a minimum cost g-path cover on the directed graph H; (f) extracting the final segments based on the g-path cover on H therefore segmenting the entire intensity modulated beam. In one embodiment of the present invention, step (d) further comprises the following steps: (g) introducing a vertex for each segment; (h) introducing an edge between any two segments that can be delivered together; and (i) assigning a cost to each edge that is the equal to the amount of machine delivery error introduced when delivering the two segments together. In one embodiment of the present invention, in step (h), the two segments have no minimum leaf separation and no interdigitation if for Siemens MLC. In one embodiment of the present invention, in step (h), the two segments have interdigitation.

In one embodiment, the present invention provides a method comprising the following steps: (a) partitioning an intensity modulated beam into a set of sub-IMBs; (b) partitioning the sub-IMBs into segments, wherein steps (a) and (b) introduce no machine delivery error; and (c) linking the segments to thereby reduce the number of segments. In one embodiment of the present invention, step (b) further comprises the following steps: (d) constructing a directed graph H based on the segments extracted; (e) determining a minimum cardinality g'-path cover on the directed graph H; and (f) extracting the final segments based on the g'-path cover on H therefore segmenting the entire intensity modulated beam. In one embodiment of the present invention, step (d) further comprises the following steps: (g) introducing a vertex for each segment; and (h) introducing an edge between any two segments that can be delivered together for any two segment that can be delivered together. In one embodiment of the present invention, in step (h), the two segments have no minimum leaf separation and no interdigitation. In one embodiment of the present invention, in step (h) the two segments have interdigitation.

In one embodiment, the present invention provides a method comprising the following steps: (a) generating a canonical delivery option for each set of field opening endpoints for a an intensity modulated beam; (b) for every two consecutive intensity modulated beam columns of the intensity modulated beam, determining a series of minimum cost g-matchings between the canonical delivery options of the intensity modulated beam columns; (c) determining the tradeoff curves based on the g-matchings; and (d) extracting the segments for the intensity modulated beam based on the matched field openings of the canonical delivery options from the determined g-matchings in an increasing order of consecutive intensity modulated beam columns to thereby partition the intensity modulate beam.

In one embodiment, the present invention provides a method comprising the following steps: (a) generating a canonical delivery option for each set of field opening endpoints for a an intensity modulated beam; (b) for every two consecutive intensity modulated beam columns of the intensity modulated beam, determining maximum matchings with no machine delivery error between the canonical delivery options of the intensity modulated beam columns; and (c) extracting the segments for the intensity modulated beam based on the matched field openings of the canonical delivery options from the determined matchings in an increasing order of consecutive intensity modulated beam columns to thereby partition the sub-IMB.

EXAMPLES

Example 1

To examine the behavior and performance of several 3-D SLS algorithms of the present invention, the algorithms were implemented them using C on the Linux systems and conducted extensive experimental studies using real medical data obtained from the Department of Radiation Oncology, University of Maryland School of Medicine.

Figures 33, 34:
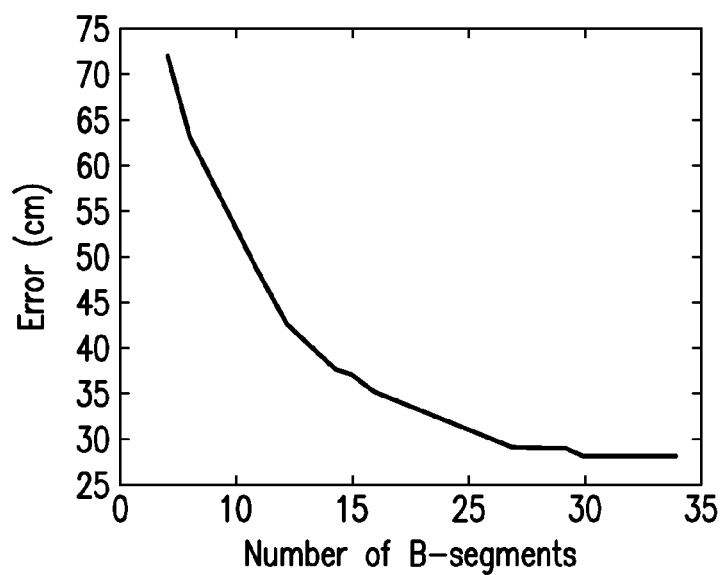
FIG. 33 is a table showing the output results of a basic 3-D SLS program according to one embodiment of the present invention with tongue-or-groove error control on some clinical intensity maps.
FIG. 34 is a graph of the tradeoff curve between the number of B-segments and tongue-or-groove error of an IM of size 10×10 for a pancreatic cancer case.

For example, a basic 3-D SLS algorithm with error control was implemented for the Elekta™ model, and experimented with the program using about 120 clinical IMs. Note that most of the IMs used in current cancer patient treatments on the Elekta™ system have a maximum height around 5, and on such IMs, the basic 3-D SLS algorithm usually produces solutions that are very close to the optimal ones for the general 3-D SLS problem. Moreover, the 3-D SLS algorithm, according to one embodiment of the present invention, runs reasonably fast. Table 1 of FIG. 33 shows the output results of a basic 3-D SLS program according to one embodiment of the present invention with tongue-or-groove error control on some clinical intensity maps. In Table 1, # denotes the number of B-segments, denotes the tongue-or-groove error (in cm), and t denotes the estimated total treatment time (in minutes) for delivering the corresponding SLS plan on an Elekta™ SL20 series linear accelerator (the estimations are based on a typical machine setup time on an Elekta™ SL20 MLC system). All execution times are collected on a laptop computer equipped with a 1.7 GHz Mobile Pentium 4 CPU, 512 MB memory, and 266 MHz frontside bus.

FIG. 34 is a graph of the tradeoff curve between the number of B-segments and tongue-or-groove error of an IM of size 10×10 for a pancreatic cancer case. The execution time of the program on this IM is 25 minutes on a laptop computer equipped with a 1.7 GHz Mobile Pentium 4 CPU and 266 MHz frontside bus. (Note that the execution time will be significantly faster on a treatment planning computer which is usually equipped with the fastest CPU and system bus.) Since the majority of the IMRT treatment plans are computed in an off-line fashion, the program is actually practical for clinical applications. Monte Carlo simulations were also performed to create the dose distributions of the treatment plans corresponding to the tradeoff curve in FIG. 34.

Figure 35:
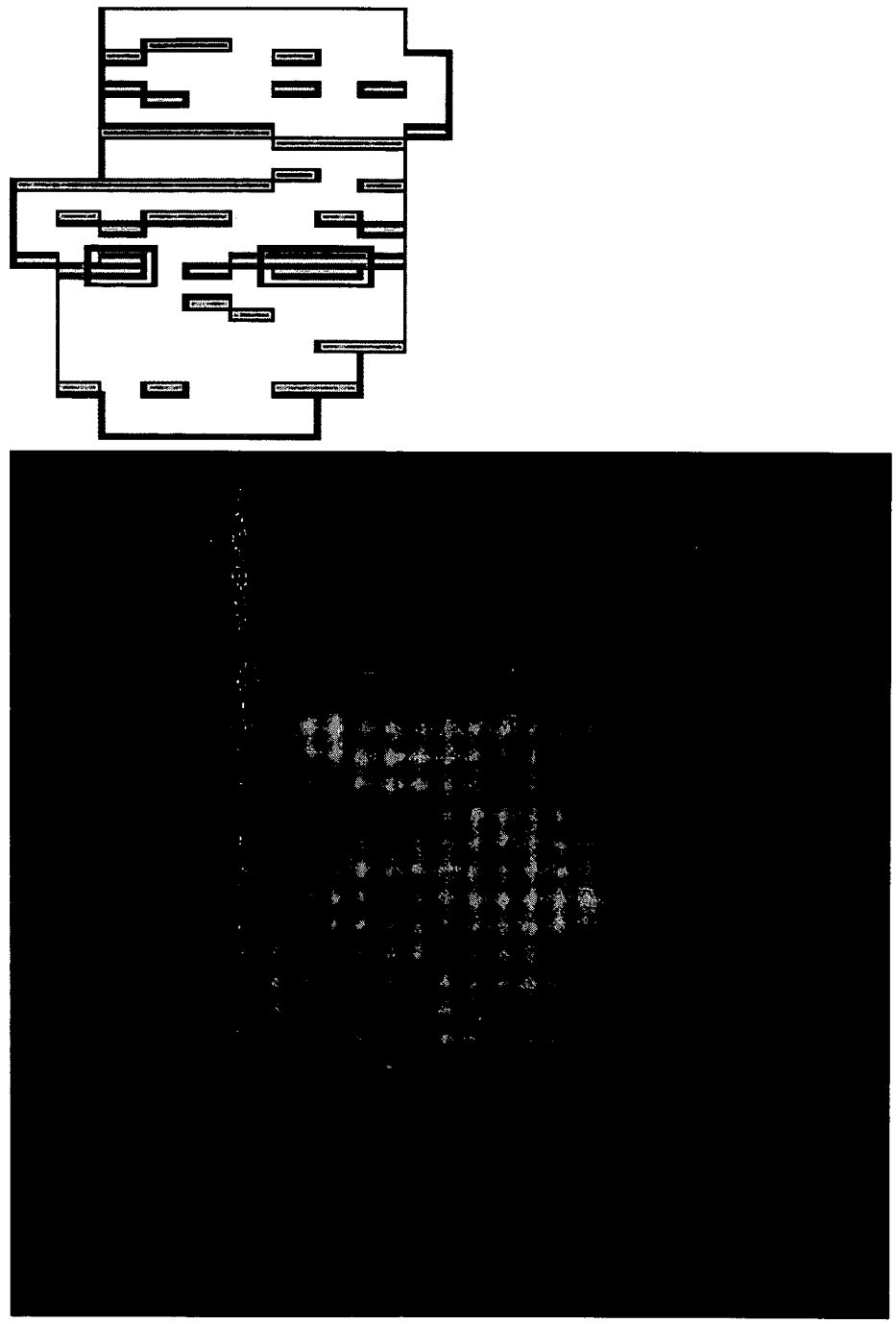
FIG. 35 is a pair of images showing one set of dose distributions for the IM of FIG. 34.

FIG. 35 is a pair of images showing one set of dose distributions for the IM of FIG. 34. The plan as shown is selected from the tradeoff curve in FIG. 34 and has 7 B-segments and 72 cm error. The one on the left was created by Monte Carlo simulations and the one on the right highlights the tongue-or-groove error regions (the shaded rectangles) on the simulated dose distributions. The two tongue-and-groove error regions are also indicated by the unshaded rectangles. Note that, the tongue-and-groove errors arise whenever two shaded rectangles are abut along the vertical direction (leaf moving direction), which indicates an intersection between the tongue error regions and the groove error regions.

Figure 36:
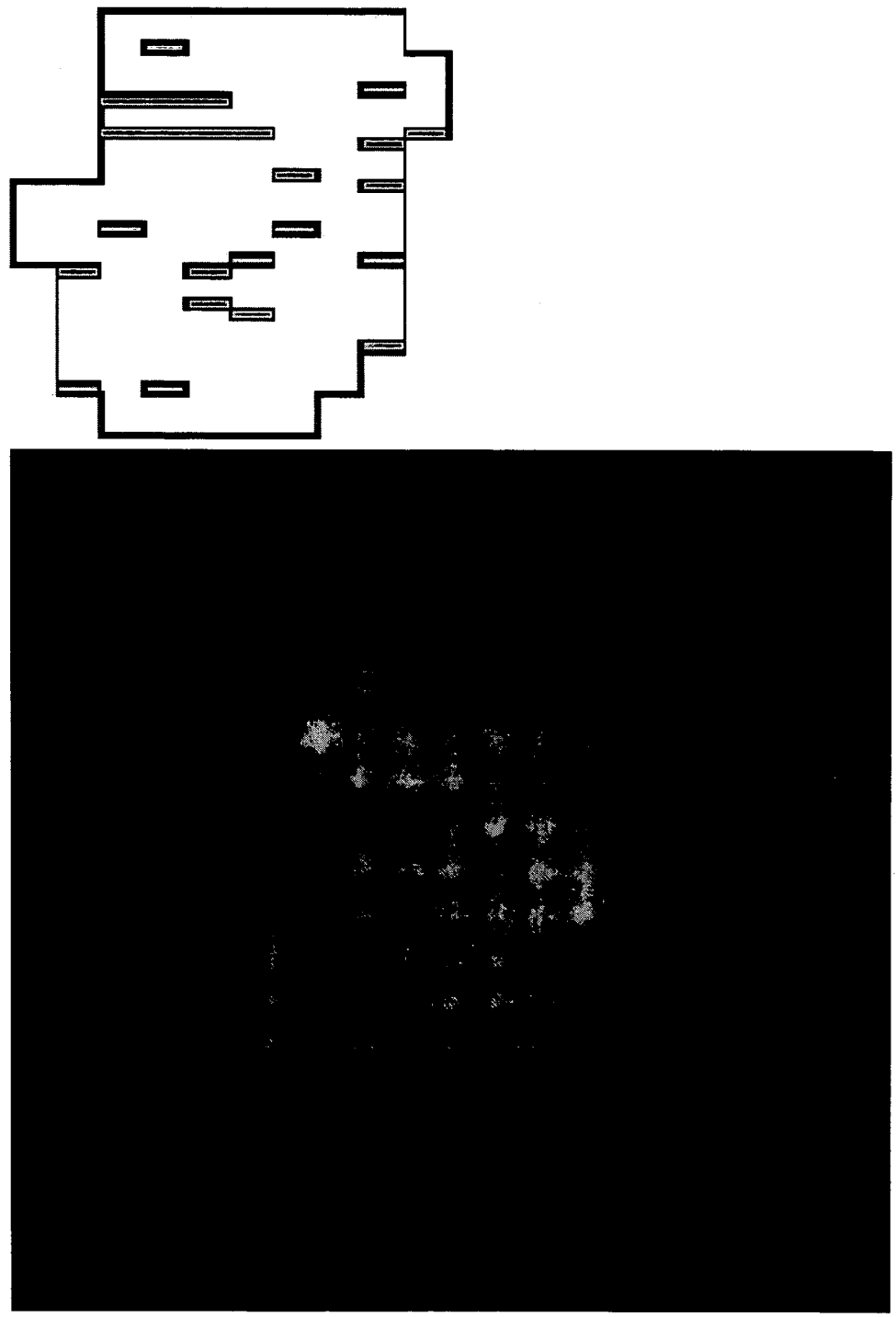
FIG. 36 is a pair of images showing one set of dose distributions for the IM of FIG. 34.

FIG. 36 is a pair of images showing one set of dose distributions for the IM of FIG. 34 The plan as shown is selected from the tradeoff curve in FIG. 34 and has 14 B-segments and 38 cm error. The one on the left was created by Monte Carlo simulations and the one on the right highlights the tongue-or-groove error regions (the shaded rectangles) on the simulated dose distributions. The plan as shown does not have any tongue-and-groove error.

FIGS. 35 and 36 show the dose distributions of two treatment plans selected based on the tradeoff curve: The one in FIG. 35 has 7 B-segments and 72 cm error and the one in FIG. 36 has 14 B-segments and 38 cm error. As shown by these dose distributions, the underdose and leakage areas in FIG. 36 are much less than those in FIG. 35 (see the two images to the right in FIGS. 35 and 36, where the shaded regions highlight the underdose and leakage areas). This confirms that the basic 3-D SLS algorithm indeed determines the desired tradeoff between the number of B-segments and the machine delivery error.

Figure 37:
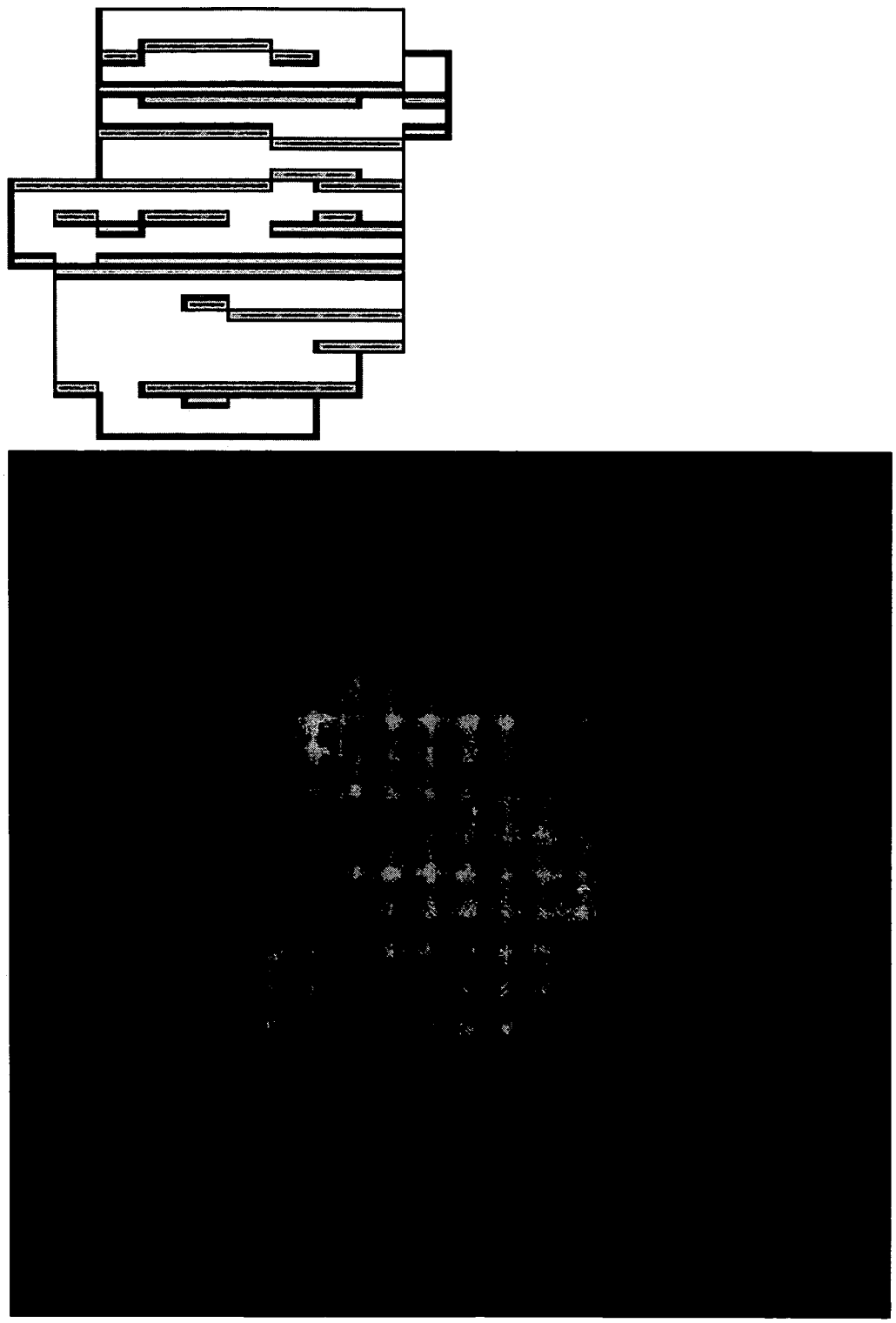
FIG. 37 is a pair of images showing the dose distribution of a treatment plan computed by the SLS algorithm without error control for the IM of FIG. 34.

FIG. 37 is a pair of images showing the dose distribution of a treatment plan computed by the SLS algorithm without error control as described in the "Chen et al. I" paper for the IM of FIG. 34. Like the plan for FIG. 35 this plan (without error control) also has 7 B-segments but with an error of 112 cm (almost 60% more error than the plan for FIG. 12(b)). Comparisons of FIGS. 35 and 37 demonstrate the advantage of the 3-D SLS algorithms, in accordance with several embodiments of the present invention, over the previous ones in the "Chen et al. I" paper. As shown by these figures, the dose distributions of the SLS plans are may be much smoother and contain much fewer "slices" of "dips" (error areas) in the transitions between adjacent columns of the dose distributions.

3-D SLS algorithms of the present invention were also compared with the current most popular commercial planning system CORVUS™, which also showed significant improvements. For instance, on the same IM for FIG. 34, to produce a plan with the same error as the one for FIG. 36, CORVUS™ would need 52 B-segments, in contrast to the 14 B-segments computed by the SLS program, in accordance with one embodiment of the present invention, (an almost 4-fold improvement).

As another example, the performance of the 3-D SLS algorithms of one embodiment of the present invention without error control for the Siemens™ and Varian™ MLCs were compared with the well-known benchmark leaf sequencing algorithm by Xia and Verhey41 (which does not consider error control). The results are given in Tables 2 and 3 of FIGS. 38 and 39, respectively. Table 2 shows SLS vs. Xia and Verhey's algorithm on a Siemens™ model, and Table 3 shows SLS vs. Xia and Verhey's algorithm on a Varian™ model. For this comparison, the SLS algorithms of the present invention outperform Xia and Verhey's algorithm 41 by a factor of about 8% on the Siemens™ model, and a factor of about 7% on the Varian™ model.

Example 2

An SLSWNE algorithm of the present invention was implemented using C on Linux systems, and experimented with it on about 80 IM sets obtained from the Dept. of Radiation Oncology of the Univ. of Maryland Medical School. Comparisons were conducted with CORVUS™ 5.0, one of the most popular commercial leaf sequencing systems, a well-known algorithm by Xia and Verhey, described in Xia et al., "MLC Leaf Sequencing Algorithm for Intensity Modulated Beams with Multiple Static Segments. Med. Phys., 25:1424{1434, 1998, the entire contents and disclosure of which is hereby incorporated by reference, and the previous SLS algorithms described in the "Chen et al. I" and "Chen et al. III" papers.

Specifically, the following aspects of these algorithms were examined: (1) the number of MLC-apertures, (2) the execution time, and (3) the amount of delivery error. Experimental results showed that the SLSWNE algorithm/software, in accordance with one embodiment of the present invention, compares very favorably with the previous approaches. In one embodiment of the present invention, the SLSWNE algorithm/software can reduce the number of MLC-apertures by about 50% when comparing with the CORVUS™ 5.0 system, and about 30% when comparing with Xia and Verhey's algorithm. Note that the algorithm as presented in Xia et al. does not do error reduction, and hence its treatment plans may incur additional delivery error. Table 4 of FIG. 40 gives some comparison results on the number of MLC-apertures, execution time, and error of these algorithms.

Table 4 provides comparison results on a head and neck cancer prescription. The dose prescription has 7 IMs; the size of each IM is 25×40, and the maximum height is 5. The listed numbers are the numbers of the MLC-apertures computed by the algorithms/software for each IM. The error is the amount of new error introduced by the set of MLC-apertures computed by the error volume percentage formula given in the "Chen et al. III" paper, and is the average percentage error over the 7 IMs. Note that SLS[1] described the "Chen et al. I" paper only minimizes the number of MLC-apertures but does not reduce error; SLS[2] described in the "Chen et al. III" paper, computes a tradeoff between the number of MLC-apertures and amount of error (in Table 4, the number of MLC-apertures shown for $SLS^2$ on each IM of a height $\leq 5$ is when the error is driven to zero by $SLS^2$).

Comparing with the SLS algorithm without error reduction in the "Chen et al. I" paper (SLS1 in Table 4), the SLSWNE algorithm computes about the same number of MLC-apertures. Comparing with the SLS algorithm with error reduction in the "Chen et al. III" paper (SLS2 in Table 4), the SLSWNE algorithm produces about the same number of MLC-apertures in a significantly faster execution time. As mentioned above, previous IM partition methods may add new delivery error. The SLSWNE algorithm, according to one embodiment of the present invention, uses the mountain reduction scheme that incurs no new error; thus the MLC-apertures that it is possible to obtain are always "error-free". To demonstrate this advantage of the SLSWNE algorithm, experiments were conducted on IMs of height 20. Table 5 of FIG. 41 in shows some comparison results, in which the number of MLC-apertures is computed by the SLSWNE algorithm, in accordance with one embodiment of the present invention. The error is taken from the tradeoff curve computed by the SLS algorithm in the "Chen et al. III" paper when setting the number of MLC-apertures exactly the same as what the SLSWNE algorithm, according to one embodiment of the present invention, outputs. Clearly, the MLC-apertures computed by the SLS algorithm in the "Chen et al. III" paper are not "error-free" for IMs with large heights.

Table 5 provides comparison results on a head and neck cancer prescription: The dose prescription has 7 intensity maps; the size of each IM is 25×40, and the maximum height is 20. The number of MLC-apertures produced by the SLS algorithm in the "Chen et al. III" paper for each IM is chosen to be exactly the same as the corresponding number of MLC-apertures output by SLSWNE algorithm, according to one embodiment of the present invention, in order to show the additional error percentage incurred by the SLS algorithm in the "Chen et al. III" paper.

Proofs of various algorithms, lemmas, theorems, etc. may be found in the article, Chen et al. "Generalized Geometric Approaches for Leaf Sequencing Problems in Radiation Therapy" (2004) and in Chen et al. "Mountain Reduction, Block Matching, and Medical Applications" (2005), the entire contents and disclosures of which are hereby incorporated by reference.

All documents, patents, journal articles and other materials cited in the present application are hereby incorporated by reference.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

The invention claimed is:

1. A method comprising the following steps:
   (a) recursively partitioning an intensity modulated beam into plateaus; and
   (b) partitioning the plateaus into segments; and
   (c) storing in a storage medium a treatment plan based on the segments of step (b), wherein step (a) comprises determining a tradeoff between machine delivery error and the number of segments into which the plateaus will be partitioned in step (b).

2. The method of claim 1, where step (a) further comprises: partitioning the intensity modulated beam (IMB) into a sub-IMB, and wherein the method further comprises the following step:
   (d) determining the tradeoff curve between the number of segments and error for the sub-IMB.

3. A method comprising the following steps:
   (a) recursively partitioning an intensity modulated beam into plateaus;
   (b) partitioning the plateaus into segments; and
   (c) storing in a storage medium a treatment plan based on the segments of step (b), wherein step (a) comprises determining a tradeoff between machine delivery error and the number of segments into which the plateaus will be partitioned in step (b) and wherein step (b) comprises the following the steps:
   (d) constructing a directed graph based on the plateaus;
   (e) determining a series of minimum cost flows in the directed graph;
   (f) determining a tradeoff between the number of segments and machine delivery errors based on the determined minimum cost flows, and
   (g) extracting the segments from the directed graph based on the tradeoff determined in step (f) to thereby partition the plateaus.

4. The method of claim 3, wherein step (d) comprises the following steps:
   (h) constructing a directed graph based on intensity modulated beam grids of the plateaus of an intensity modulated beam, wherein vertices of the directed graph include all intersection points of the intensity modulated beam grids of the plateaus that are either part of a peak or an interior of a polygon corresponding to the intensity modulated beam, and wherein the edges of the directed graph include those edges of the plateaus whose end points are graph vertices in the directed graph;
   (i) for all graph vertices corresponding to the same peak direction, adding either a source vertex or sink vertex to the directed graph;
   (j) adding edges to the directed graph from the source vertex or sink vertex to respective peak vertices;
   (k) assigning a unit flow capacity to each graph vertex and edge of the directed graph; and
   (l) to each edge that is vertical assigning a cost that is equal to the geometric length of the vertical edge, and to each edge that is horizontal a cost of zero.

5. The method of claim 4, wherein step (h) comprises the following steps:
   (m) extracting connections between a left peak and a right peak of the polygon based on the minimum cost flow;
   (n) eliminating any remaining unconnected peaks using only horizontal edges; and
   (o) extracting resulting segments from the directed graph to thereby partition the plateaus.

6. The method of claim 5, wherein for an edge involving a left peak vertex, the direction of the edge is away from the left peak.

7. The method of claim 5, wherein for an edge involving a right peak vertex, the direction of the edge is toward the right peak.

8. The method of claim 5, wherein the direction of a horizontal edge that does not involve any peak vertex is from left to right.

9. The method of claim 5, wherein the direction of a vertical edge that does not involve a peak vertex is bidirectional.

10. The method of claim 5, wherein, for all left peak vertices, a source vertex is added to the directed graph.

11. The method of claim 5, wherein, for all right peak vertices, a sink vertex is added to the directed graph.

12. The method of claim 5, wherein the minimum cost flow in the directed graph yields a maximum set of mutually disjoint paths.

13. A method comprising the following steps:
(a) recursively partitioning an intensity modulated beam into plateaus;
(b) partitioning the plateaus into segments; and
(c) storing in a storage medium a treatment plan based on the segments of step (b), wherein step (a) comprises determining a tradeoff between machine delivery error and the number of segments into which the plateaus will be partitioned in step (b), wherein the intensity modulated beam comprises a plurality of z-posts, and wherein step (a) comprises the following steps:
(d) choosing an intensity level d wherein, $1 \leq d \leq I_{max}$, wherein $I_{max}$ is the maximum intensity level of the intensity modulated beam;
(e) selecting all z-posts having a height of at least d to form a set of selected z-posts;
(f) cutting each selected z-post whose height is $\geq d$ at level d to form a plateau of z-posts of height d;
(g) removing the plateau of z-posts from the intensity modulated beam; and
(h) recursively partitioning any remaining portion of the intensity modulated beam until there is no remaining portion of the intensity modulated beam.

14. The method of claim 13, wherein step (h) comprises repeating steps (d), (e), (f) and (g) on any remaining portion of the intensity modulated beam until there is no remaining portion of the intensity modulated beam.

15. The method of claim 13, wherein d is a function of the maximum intensity level $I_{max}$.

16. The method of claim 13, wherein $$d = \left\lceil \frac{I_{max}}{2} \right\rceil.$$

17. The method of claim 13, wherein d is based on the volume of the plateau of z-posts.

18. The method of claim 13 wherein $d=2^i$, where $i=\mathrm{Int}(\log_2(I_{max}))-1$.

19. The method of claim 13, wherein d has a value such that the volume of the plateau of z-posts is maximized.

20. The method of claim 13, wherein d is determined by the slice method.

21. A method comprising the following steps:
(a) recursively partitioning an intensity modulated beam into plateaus;
(b) partitioning the plateaus into segments; and
(c) storing in a storage medium a treatment plan based on the segments of step (b), wherein step (a) comprises partitioning the intensity modulated beam into a sub-IMB and wherein step (a) comprises determining the tradeoff curve between the number of segments and error for the sub-IMB by the following steps:
(d) generating a canonical delivery option for each set of field opening endpoints for a plurality of intensity modulated beam columns of the sub-IMB;
(e) for every two consecutive intensity modulated beam columns, determining a series of minimum cost g-matchings between the canonical delivery options of the intensity modulated beam columns;
(f) determining the tradeoff curves based on the g-matchings; and
(g) extracting the segments for the sub-IMB based on the matched field openings of the canonical delivery options from the determined g-matchings in an increasing order of consecutive intensity modulated beam columns to thereby partition the sub-IMB.

22. The method of claim 21, wherein in step (d) only one set of left and right field opening endpoints is generated for each intensity beam column.

23. The method of claim 21, wherein in step (d) more than one set of left and right field opening endpoints is generated for each intensity beam column.

24. The method of claim 21, wherein the matched field openings have no interdigitation and minimum leaf separation.

25. The method of claim 21, wherein the matched field openings have no minimum leaf separation and no interdigitation.

26. The method of claim 21, wherein the matched field openings have interdigitation.

27. The method of claim 21, wherein the method further comprises choosing a number m of Steiner points for forming the sets of field opening endpoints, and wherein each unique canonical delivery option contains at most m Steiner points for each set of field opening endpoints.

28. A method comprising the following steps:
(a) recursively partitioning an intensity modulated beam into plateaus;
(b) partitioning the plateaus into segments, wherein step (a) comprises determining a tradeoff between machine delivery error and the number of segments into which the plateaus will be partitioned in step (b);
(c) linking the segments to thereby reduce the number of segments; and
(d) storing in a storage medium a treatment plan based on the linked segments of step (c).

29. The method of claim 28, wherein step (a) further comprises: partitioning the intensity modulated beam (IMB) into a sub-IMB, and wherein the method further comprises the following step:
(e) determining the tradeoff curve between the number of segments and error for the sub-IMB.

30. A method comprising the following steps:
(a) recursively partitioning an intensity modulated beam into plateaus;
(b) partitioning the plateaus into segments, wherein step (a) comprises determining a tradeoff between machine delivery error and the number of segments into which the plateaus will be partitioned in step (b);
(c) linking the segments to thereby reduce the number of segments; and
(d) storing in a storage medium a treatment plan based on the linked segments of step (c), wherein step (c) further comprises the following steps:
(e) constructing a directed graph H based on the segments extracted;
(f) determining a minimum cost g-path cover on the directed graph H;
(g) extracting the final segments based on the g-path cover on H therefore segmenting the entire intensity modulated beam.

31. The method of claim 30, wherein step (e) further comprises the following steps:
(h) introducing a vertex for each segment;
(i) introducing an edge between any two segments that can be delivered together; and (j) assigning a cost to each edge that is the equal to the amount of machine delivery error introduced when delivering the two segments together.

32. The method of claim 31, wherein in step (i), the two segments have no minimum leaf separation and no interdigitation when for a multileaf collimator.

33. The method of claim 31, wherein in step (i), the two segments have interdigitation.

34. A method comprises the following steps:
(a) generating a canonical delivery option for each set of field opening endpoints for an intensity modulated beam;
(b) for every two consecutive intensity modulated beam columns of the intensity modulated beam, determining a series of minimum cost g-matchings between the canonical delivery options of the intensity modulated beam columns;
(c) determining the tradeoff curves based on the g-matchings;
(d) extracting the segments for the intensity modulated beam based on the matched field openings of the canonical delivery options from the determined g-matchings in an increasing order of consecutive intensity modulated beam columns to thereby partition the intensity modulate beam; and
(e) storing in a storage medium a treatment plan based on the extracted segments of step (d).

35. A method comprising the following steps:
(a) recursively partitioning an intensity modulated beam into plateaus; and
(b) partitioning the plateaus into segments; and
(c) implementing a treatment plan based on the segments of step (b), wherein step (a) comprises determining a tradeoff between machine delivery error and the number of segments into which the plateaus will be partitioned in step (b).

36. The method of claim 35, wherein step (a) further comprises: partitioning the intensity modulated beam (IMB) into a sub-IMB, and wherein the method further comprises the following step:
(d) determining the tradeoff curve between the number of segments and error for the sub-IMB.

37. A method comprising the following steps:
(a) recursively partitioning an intensity modulated beam into plateaus;
(b) partitioning the plateaus into segments; and
(c) implementing a treatment plan based on the segments of step (b), wherein step (a) comprises determining a tradeoff between machine delivery error and the number of segments into which the plateaus will be partitioned in step (b) and wherein step (b) comprises the following steps:
(d) constructing a directed graph based on the plateaus;
(e) determining a series of minimum cost flows in the directed graph;
(f) determining a tradeoff between the number of segments and machine delivery errors based on the determined minimum cost flows, and
(g) extracting the segments from the directed graph based on the tradeoff determined in step (f) to thereby partition the plateaus.

38. The method of claim 37, wherein step (d) comprises the following steps:
(h) constructing a directed graph based on intensity modulated beam grids of the plateaus of an intensity modulated beam, wherein vertices of the directed graph include all intersection points of the intensity modulated beam grids of the plateaus that are either part of a peak or an interior of a polygon corresponding to the intensity modulated beam, and wherein the edges of the directed graph include those edges of the plateaus whose end points are graph vertices in the directed graph;
(i) for all graph vertices corresponding to the same peak direction, adding either a source vertex or sink vertex to the directed graph;
(j) adding edges to the directed graph from the source vertex or sink vertex to respective peak vertices;
(k) assigning a unit flow capacity to each graph vertex and edge of the directed graph; and
(l) to each edge that is vertical assigning a cost that is equal to the geometric length of the vertical edge, and to each edge that is horizontal a cost of zero.

39. The method of claim 38, wherein step (h) comprises the following steps:
(m) extracting connections between a left peak and a right peak of the polygon based on the minimum cost flow;
(n) eliminating any remaining unconnected peaks using only horizontal edges; and
(o) extracting resulting segments from the directed graph to thereby partition the plateaus.

40. The method of claim 39, wherein for an edge involving a left peak vertex, the direction of the edge is away from the left peak.

41. The method of claim 39, wherein for an edge involving a right peak vertex, the direction of the edge is toward the right peak.

42. The method of claim 39, wherein the direction of a horizontal edge that does not involve any peak vertex is from left to right.

43. The method of claim 39, wherein the direction of a vertical edge that does not involve a peak vertex is bidirectional.

44. The method of claim 39, wherein, for all left peak vertices, a source vertex is added to the directed graph.

45. The method of claim 39, wherein, for all right peak vertices, a sink vertex is added to the directed graph.

46. The method of claim 39, wherein the minimum cost flow in the directed graph yields a maximum set of mutually disjoint paths.

47. A method comprising the following steps:
(a) recursively partitioning an intensity modulated beam into plateaus;
(b) partitioning the plateaus into segments; and
(c) implementing a treatment plan based on the segments of step (b), wherein step (a) comprises determining a tradeoff between machine delivery error and the number of segments into which the plateaus will be partitioned in step (b), wherein the intensity modulated beam comprises a plurality of z-posts, and wherein step (a) comprises the following steps:
(d) choosing an intensity level d wherein, $1 \leq d \leq I_{max}$, wherein $I_{max}$ is the maximum intensity level of the intensity modulated beam;
(e) selecting all z-posts having a height of at least d to form a set of selected z-posts;
(f) cutting each selected z-post whose height is $\geq d$ at level d to form a plateau of z-posts of height d;
(g) removing the plateau of z-posts from the intensity modulated beam; and
(h) recursively partitioning any remaining portion of the intensity modulated beam until there is no remaining portion of the intensity modulated beam.

48. The method of claim 47, wherein step (h) comprises repeating steps (d), (e), (f) and (g) on any remaining portion of the intensity modulated beam until there is no remaining portion of the intensity modulated beam.

49. The method of claim 47, wherein d is a function of the maximum intensity level $I_{max}$.

50. The method of claim 47, wherein $$d = \left\lceil \frac{I_{max}}{2} \right\rceil.$$

51. The method of claim 47, wherein d is based on the volume of the plateau of z-posts.

52. The method of claim 47 wherein $d=2^i$, where $i=\text{Int}(\log_2(I_{max}))-1$).

53. The method of claim 47, wherein d has a value such that the volume of the plateau of z-posts is maximized.

54. The method of claim 47, wherein d is determined by the slice method.

55. A method comprising the following steps:
(a) recursively partitioning an intensity modulated beam into plateaus;
(b) partitioning the plateaus into segments; and
(c) implementing a treatment plan based on the segments of step (b), wherein step (a) comprises partitioning the intensity modulated beam into a sub-IMB and wherein step (a) comprises determining the tradeoff curve between the number of segments and error for the sub-IMB by the following steps:
(d) generating a canonical delivery option for each set of field opening endpoints for a plurality of intensity modulated beam columns of the sub-IMB;
(e) for every two consecutive intensity modulated beam columns, determining a series of minimum cost g-matchings between the canonical delivery options of the intensity modulated beam columns;
(f) determining the tradeoff curves based on the g-matchings; and
(g) extracting the segments for the sub-IMB based on the matched field openings of the canonical delivery options from the determined g-matchings in an increasing order of consecutive intensity modulated beam columns to thereby partition the sub-IMB.

56. The method of claim 55, wherein in step (d) only one set of left and right field opening endpoints is generated for each intensity beam column.

57. The method of claim 55, wherein in step (d) more than one set of left and right field opening endpoints is generated for each intensity beam column.

58. The method of claim 55, wherein the matched field openings have no interdigitation and minimum leaf separation.

59. The method of claim 55, wherein the matched field openings have no minimum leaf separation and no interdigitation.

60. The method of claim 55, wherein the matched field openings have interdigitation.

61. The method of claim 55, wherein the method further comprises choosing a number m of Steiner points for forming the sets of field opening endpoints, and wherein each unique canonical delivery option contains at most m Steiner points for each set of field opening endpoints.

62. A method comprising the following steps:
(a) recursively partitioning an intensity modulated beam into plateaus;
(b) partitioning the plateaus into segments, wherein step (a) comprises determining a tradeoff between machine delivery error and the number of segments into which the plateaus will be partitioned in step (b);
(c) linking the segments to thereby reduce the number of segments; and
(d) implementing a treatment plan based on the linked segments of step (c).

63. The method of claim 62, wherein step (a) further comprises: partitioning the intensity modulated beam (IMB) into a sub-IMB, and wherein the method further comprises the following step:
(f) determining the tradeoff curve between the number of segments and error for the sub-IMB.

64. A method comprising the following steps:
(a) recursively partitioning an intensity modulated beam into plateaus;
(b) partitioning the plateaus into segments, wherein step (a) comprises determining a tradeoff between machine delivery error and the number of segments into which the plateaus will be partitioned in step (b);
(c) linking the segments to thereby reduce the number of segments; and
(d) implementing a treatment plan based on the linked segments of step (c), wherein step (c) further comprises the following steps:
(e) constructing a directed graph H based on the segments extracted;
(f) determining a minimum cost g-path cover on the directed graph H;
(g) extracting the final segments based on the g-path cover on H therefore segmenting the entire intensity modulated beam.

65. The method of claim 64, wherein step (e) further comprises the following steps:
(h) introducing a vertex for each segment;
(i) introducing an edge between any two segments that can be delivered together; and
(j) assigning a cost to each edge that is the equal to the amount of machine delivery error introduced when delivering the two segments together.

66. The method of claim 65, wherein in step (i), the two segments have no minimum leaf separation and no interdigitation when for a multileaf collimator.

67. The method of claim 65, wherein in step (i), the two segments have interdigitation.

68. A method comprises the following steps:
(a) generating a canonical delivery option for each set of field opening endpoints for an intensity modulated beam;
(b) for every two consecutive intensity modulated beam columns of the intensity modulated beam, determining a series of minimum cost g-matchings between the canonical delivery options of the intensity modulated beam columns;
(c) determining the tradeoff curves based on the g-matchings;
(d) extracting the segments for the intensity modulated beam based on the matched field openings of the canonical delivery options from the determined g-matchings in an increasing order of consecutive intensity modulated beam columns to thereby partition the intensity modulate beam; and
(e) implementing a treatment plan based on the extracted segments of step (d).

* * * * *